United States Patent
Salafsky

(10) Patent No.: US 10,672,502 B2
(45) Date of Patent: Jun. 2, 2020

(54) METHODS FOR DETERMINING PROTEIN STRUCTURE USING A SURFACE-SELECTIVE NONLINEAR OPTICAL TECHNIQUE

(71) Applicant: Biodesy, Inc., South San Francisco, CA (US)

(72) Inventor: Joshua Salafsky, San Francisco, CA (US)

(73) Assignee: BIODESY, INC., South San Francisco, CA (US)

(*) Notice: Subject to any disclaimer, the term of this patent is extended or adjusted under 35 U.S.C. 154(b) by 271 days.

(21) Appl. No.: 15/089,013

(22) Filed: Apr. 1, 2016

(65) Prior Publication Data

US 2016/0292354 A1 Oct. 6, 2016

Related U.S. Application Data

(60) Provisional application No. 62/148,649, filed on Apr. 16, 2015, provisional application No. 62/142,314, filed on Apr. 2, 2015.

(51) Int. Cl.
| | |
|---|---|
| *G16B 15/00* | (2019.01) |
| *G01N 33/58* | (2006.01) |
| *G01N 21/63* | (2006.01) |
| *G01N 33/543* | (2006.01) |
| *G01N 33/542* | (2006.01) |
| *G01B 11/14* | (2006.01) |
| *G01N 33/68* | (2006.01) |
| *G01N 21/21* | (2006.01) |

(52) U.S. Cl.
CPC .......... *G16B 15/00* (2019.02); *G01B 11/14* (2013.01); *G01N 21/636* (2013.01); *G01N 33/542* (2013.01); *G01N 33/54373* (2013.01); *G01N 33/582* (2013.01); *G01N 33/6803* (2013.01); *G01N 21/21* (2013.01); *G01N 2201/0683* (2013.01); *G01N 2201/06113* (2013.01)

(58) Field of Classification Search
None
See application file for complete search history.

(56) References Cited

U.S. PATENT DOCUMENTS

| | | |
|---|---|---|
| 5,145,790 A | 9/1992 | Mattingly et al. |
| 5,156,810 A | 10/1992 | Ribi |
| 5,236,826 A | 8/1993 | Marshall |
| 5,376,556 A | 12/1994 | Tarcha et al. |
| 5,633,724 A | 5/1997 | King et al. |
| 5,696,157 A | 12/1997 | Wang et al. |
| 5,800,992 A | 9/1998 | Fodor et al. |
| 5,962,248 A | 10/1999 | Tadano et al. |
| 6,055,051 A | 4/2000 | Eisenthal |
| 6,096,497 A | 8/2000 | Bauer et al. |
| 6,180,415 B1 | 1/2001 | Schultz et al. |
| 6,194,222 B1 | 2/2001 | Buechler et al. |
| 6,204,067 B1 | 3/2001 | Simon et al. |
| 6,228,326 B1 | 5/2001 | Boxer et al. |
| 6,284,197 B1 | 9/2001 | Abbott et al. |
| 6,410,245 B1 | 6/2002 | Northrup et al. |
| 6,455,303 B1 | 9/2002 | Orwar et al. |
| 6,456,423 B1 | 9/2002 | Nayfeh et al. |
| 6,699,719 B2 | 3/2004 | Yamazaki et al. |
| 6,780,584 B1 | 8/2004 | Edman et al. |
| 6,882,420 B2 | 4/2005 | Rassman et al. |
| 6,953,694 B2 | 10/2005 | Salafsky et al. |
| 7,023,547 B2 | 4/2006 | Venkatasubbarao et al. |
| 7,105,310 B1 | 9/2006 | Gray et al. |
| 7,108,970 B2 | 9/2006 | Levinson |
| 7,126,688 B2 | 10/2006 | Rassman et al. |
| 7,193,711 B2 | 3/2007 | Rassman et al. |
| 7,233,391 B2 | 6/2007 | Schermer et al. |
| 7,545,494 B2 | 6/2009 | Haiml et al. |
| 7,545,501 B2 | 6/2009 | Muraishi et al. |
| 7,709,808 B2 | 5/2010 | Reel et al. |
| 8,039,270 B2 | 10/2011 | Dultz et al. |
| 8,062,900 B2 | 11/2011 | Modavis |
| 8,139,288 B2 | 3/2012 | Osborne et al. |
| 8,355,133 B2 | 1/2013 | Dultz et al. |
| 8,497,073 B2 | 7/2013 | Salafsky |
| 8,932,822 B1 | 1/2015 | Salafsky |
| 9,182,406 B2 | 11/2015 | Salafsky |
| 10,451,630 B2 | 10/2019 | Salafsky et al. |
| 2003/0129649 A1 | 7/2003 | Kobilka et al. |
| 2004/0146460 A1 | 7/2004 | Salafsky |
| 2006/0063188 A1 | 3/2006 | Zanni et al. |
| 2008/0038281 A1 | 2/2008 | Altin et al. |

(Continued)

FOREIGN PATENT DOCUMENTS

| | | |
|---|---|---|
| CN | 1864066 A | 11/2006 |
| CN | 1997892 A | 7/2007 |

(Continued)

OTHER PUBLICATIONS

Han et al. J. Phys. Chem. B 2014, 118, 2904-2912.*
Antikainen, et al. Conformation coupled enzyme catalysis: single-molecule and transient kinetics investigation of dihydrofolate reductase. Biochemistry. Dec. 27, 2005;44(51):16835-43.
Ben-Oren, et al. Infrared nonlinear optical measurements of membrane potential in photoreceptor cells. Biophys J. Sep. 1996;71(3):1616-20.
Berkovic, et al. Interference between second-harmonic generation from a substrate and from an adsorbate layer. Journal of the Optical Society of America B—Optical Physics. 1989; 6:205-208.
Bethea. Experimental technique of dc induced SHG in liquids: measurement of the nonlinearity of CH2I2. Applied Optics. 1975; 14:1447-1451.

(Continued)

*Primary Examiner* — Michael L Borin
(74) *Attorney, Agent, or Firm* — Wilson Sonsini Goodrich & Rosati

(57) ABSTRACT

Methods, devices, and systems are disclosed for determining protein structure and dynamics using second harmonic generation (SHG) and related surface-selective nonlinear optical techniques.

21 Claims, 18 Drawing Sheets

(56) References Cited

U.S. PATENT DOCUMENTS

| | | | |
|---|---|---|---|
| 2010/0068144 A1* | 3/2010 | Salafsky | G01N 21/6428 424/9.1 |
| 2012/0202296 A1 | 8/2012 | Eisenthal | |
| 2013/0129628 A1 | 5/2013 | Pantazis et al. | |
| 2013/0288271 A1 | 10/2013 | Salafsky | |
| 2014/0113312 A1 | 4/2014 | Salafsky | |
| 2015/0051110 A1 | 2/2015 | Salafsky et al. | |

FOREIGN PATENT DOCUMENTS

| | | | |
|---|---|---|---|
| EP | 0740156 A1 | 10/1996 | |
| EP | 0740156 B1 | 9/2001 | |
| EP | 0941474 B1 | 3/2006 | |
| EP | 1798555 A1 | 6/2007 | |
| EP | 3161168 A1 | 5/2017 | |
| GB | 2520111 A | 5/2015 | |
| GB | 2538216 A | 11/2016 | |
| JP | 2004521323 A | 7/2004 | |
| JP | 2004530105 A | 9/2004 | |
| JP | 2008515385 A | 5/2008 | |
| WO | WO 02/095070 A2 | 11/2002 | |
| WO | WO 03/055379 A2 | 7/2003 | |
| WO | WO 03/064991 A2 | 8/2003 | |
| WO | WO-2011140030 A2 | 11/2011 | |
| WO | WO 2014/201435 A1 | 12/2014 | |

OTHER PUBLICATIONS

Bieri, et al. Micropatterned immobilization of a G protein-coupled receptor and direct detection of G protein activation. Nature Biotechnology. 1999; 17:1105-1108.

Bouevitch, et al. Probing membrane potential with nonlinear optics. Biophys J. Aug. 1993;65(2):672-9.

Boyd, et al. Local-field enhancement on rough surfaces with the use of optical 2nd-harmonic generation. Phys. Rev. B 1984; 30:519-526.

Brian, et al. Allogeneic Stimulation of Cyto-toxic T-cells by Supported Planar Membranes. PNAS-Biological Sciences. 1984; 81(19): 6159-6163.

Campagnola, et al. High-resolution nonlinear optical imaging of live cells by second harmonic generation. Biophys J. Dec. 1999;77(6):3341-9.

Campagnola, et al. Second-harmonic imaging microscopy for visualizing biomolecular arrays in cells, tissues and organisms. Nat Biotechnol. Nov. 2003;21(11):1356-60.

Campagnola, et al. Three-dimensional high-resolution second-harmonic generation imaging of endogenous structural proteins in biological tissues. Biophysical Journal. 2002; 81:493-508.

Chen, et al. Detection of Molecular Monolayers by Optical Second-Harmonic Generation. Physical Review Letters. 1981; 46:1010-1012.

Clark, et al. Second harmonic generation properties of fluorescent polymer-encapsulated gold nanoparticles. J. Am. Chem. Soc. 2000; 122:10234-10235.

Clarke, et al. Conformational changes of fibrinogen after adsorption. Journal of Physical Chemistry B. 2005; 109:22027-22035.

Clays, et al. Nonlinear optical properties of proteins measured by hyper-rayleigh scattering in solution. Science. Nov. 26, 1993;262(5138):1419-22.

Cohen, et al. A Fluorescent Probe Designed for Studying Protein Conformational Change. PNAS. 2005; 102(4):965-970.

Cohen, et al. Probing protein electrostatics with a synthetic fluorescent amino acid. Science. 2002; 296:1700-1703.

Conboy, et al. Studies of Alkane/water interfaces by total internal reflection second harmonic generation. J. Phys. Chem. 1994; 98:9688-9698.

Delprincipe et al. Two Photo and UV-Laser Flash Photlysis of CA Cage Dimethoynitrophenyl-EGTA-4. Cell Calcium. 1999; 25:85-91.

Ditcham, et al. An immunosensor with potential for the detection of viral antigens in body fluids, based on surface second harmonic generation. Biosens Bioelectron. May 2001;16(3):221-4.

Dworczak, et al. Electric field induced second harmonic generation (EFISH) experiments in the swivel cell: new aspects of an established method. Phys. Chem. Chem. Phys., 2000; 2:5057-5064.

Edelheit, et al. Simple and efficient site-directed mutagenesis using two single-primer reactions in parallel to generate mutants for protein structure-function studies. BMC Biotechnol. Jun. 30, 2009;9:61. doi: 10.1186/1472-6750-9-61.

Eisenthal. Photochemistry and photophysics of liquid interfaces by second harmonic spectroscopy. J. Phys. Chem. 1996; 100:12997-13006.

European search report dated Jan. 24, 2008 for EP Application No. 03736879.2.

European search report dated May 18, 2005 for EP Application No. 01995403.1.

European search report dated Dec. 3, 2004 for EP Application No. 01957166.0.

Fejer, et al. Quasi-Phase-Matched Second Harmonic Generation Tuning and Tolerances. IEEE Journal Of Quantum Electronics. 1992; 28(11):2631-2654.

Felderhof, et al. Optical second-harmonic generation from adsorbate layers in total-reflection geometry. Journal of the Optical Society of America B—Optical Physics. 1993; 10:1824-1833.

Feller, et al. Investigation of surface-induced alignment liquid-crystal molecules by optical second-harmonic generation. Physical Review A. 1991; 43(12), 6778-6792.

Finn, et al. Measurements of hyperpolarizabilities for some halogenated methanes. J. Chem. Phys. 1974; 60:454-458.

Fittinghoff. Collinear type II second-harmonic-generation frequency-resolved optical gating for use with high-numerical-aperature objectives, 1998, Opt Lett, 23(13), 1046-1048.

Galletto, et al. Enhancement of second harmonic response by adsorbates on gold colloids: the effect of aggregation. J. Phys. Chem. B. 1999; 103:8706-8710.

Ghanouni, et al. Agonist-induced conformational changes in the G-protein-coupling domain of the beta 2 adrenergic receptor. Proc Natl Acad Sci U S A. May 22, 2001;98(11):5997-6002. Epub May 15, 2001.

Ghanouni, et al. Functionally Different Agonists Induce Distinct Conformations in the G Protein Coupling Domain of the B2 Adrenergic Receptor. Journal of Biological Chemistry. 2001; 276:24433-24436.

Goh, et al. Absolute Orientation of Water-Molecules at the Neat Water-Surface. Journal of Physical Chemistry. 1988; 92:5074-5075.

Goodey, et al. Allosteric regulation and catalysis emerge via a common route. Nat Chem Biol. Aug. 2008;4(8):474-82. doi: 10.1038/nchembio.98.

Groves, et al. Micropatterning fluid bilayers on solid supports. Science. 1997; 275:651653.

Harrick. Internal reflection spectroscopy. Harrick Scientific Corporation. 2nd printing 1979.

Heinz, et al. Spectroscopy of Molecular Monolayers by Resonant Second-Harmonic Generation. Phys. Rev. Lett. 1982; 48, 478. DOI:http://dx.doi.org/10.1103/PhysRevLett.48.478.

Heinz. Determination of molecular orientation of monlayer adsorbates by optical second-harmonic generation. Physical Review A. 1991; 28(3):1883-1885.

Heinz. Second-Order Nonlinear Optical Effects at Surfaces and Interfaces. Elsevier: Amsterdam. Physical Review A. 1991; 28(3):1883-1885.

Huang, et al. Nonlinear optical properties of potential sensitive styryl dyes. Biophys J. May 1998;53(5):665-70.

Hubbard, et al. Nonlinear optical studies of a fluorinated poled polyimide guest-host system. Applied Physics Letters. 1994; 65(3):265-267.

International search report dated Jan. 22, 2002 for PCT/US2001/022411.

International search report dated Feb. 10, 2006 for PCT/US2003/017807.

International search report dated Mar. 23, 2006 for PCT/US2002/022681.

(56) References Cited

OTHER PUBLICATIONS

International search report dated Apr. 20, 2012 for PCT/US2012/030010.
International search report dated May 1, 2002 for PCT/US2001/046932.
International search report dated Oct. 20, 2001 for PCT/US2001/022412.
Jager, et al. Comparison of quasi-phase-matching geometries for second harmonic generation in poled polymer channel waveguides at 1.5 mm,. Appl. Phys. Lett.1996; 68:1183-1185.
Kajikawa, et al. Second harmonic generation in disperse-red-labeled poly(methyl methacrylate) Langmuir Blodgett film. Appl. Phys. Letters. May 3, 1993; 62(18):2161-2163.
Kalb, et al. Formation of supported planar bilayers by fusion of vesicles to supported phospholipid monolayers. Biochim Biophys Acta. Jan. 31, 1992;1103(2):307-16.
Kemnitz, et al. The Phase of 2nd-Harmonic Light Generated at an Interface and Its Relation to Absolute Molecular-Orientation. Chemical Physics Letters. 1986; 131:285-290.
Khatchatouriants, et al. GFP is a selective non-linear optical sensor of electrophysiological processes in Caenorhabditis elegans. Biophys J. Nov. 2000;79(5):2345-52.
Kriech, et al. Using the intrinsic chirality of a molecule as a label-free probe to detect molecular adsorption to a surface by second harmonic generation. Applied Spectroscopy. 2005; 59:46-753.
Levine, et al. Absolute signs of hyperpolarizabilities in the liquid state. J. Chem. Phys. 1974; 60(10)3856-3858.
Levine, et al. Charge transfer complexes and hyperpolarizabilities. J. Chem. Phys. 1977; 66:1070-1074.
Levine, et al. Molecular hyperpolarizabilities determined from conjugated and nonconjugated organic liquids. Appl. Phys. Lett. 1974; 24:445-447.
Levine, et al. Second and third order hyperpolarizabilities of organic molecules. J. Chem. Phys. 1975; 63(6):2666-2682.
Levine, et al. Second Order Hyperpolarizability of a Polypeptide a-helix: Poly--y-benzyl-L-glutamate. J. Chem. Phys. 1976; 65(5):1989-1993.
Levine, et al. Ultraviolet dispersion of the donor-acceptor charge transfer contribution to the second order hyperpolarizability. J. Chem. Phys. 1978; 69(12): 5240-5245.
Levine. Conjugated electron contributions to the second order hyperpolarizability of substituted benzene molecules J. Chem. Phys. 1975; 63:115-117.
Lewis, et al. Second Harmonic Generation of Biological Interfaces: Probing the Membrane Protein Bacteriorhodopsin and Imaging Membrane Potential Around GFP Molecules at Specific Sites in Neuronal Cells of C. elegans. Chemical Physics. 1999; 245:133-144.
MacBeath, et al. Printing Proteins as Microarrays for High-Throughput Function Determination. Science. 2000; 289:1760-1763.
McConnell, et al. Electronic and optical properties of chemically modified metal nanoparticles and molecularly bridged nanoparticle arrays. J. Phys. Chem. B. 2000; 104:8925-8930.
Millard, et al. Second harmonic imaging microscopy. Methods Enzymol. 2003;361:47-69.
Moreaux, et al. Membrane imaging by second harmonic generation microscopy. Journal of Optical Society of America B: Optical Physics. 2000; 17(10):1685-1694.
Moree, et al. Protein Conformational Changes Are Detected and Resolved Site Specifically by Second-Harmonic Generation. Biophys J. Aug. 18, 2015;109(4):806-15. doi: 10.1016/j.bpj.2015.07.016.
Moree, et al. Small Molecules Detected by Second-Harmonic Generation Modulate the Conformation of Monomeric α-Synuclein and Reduce Its Aggregation in Cells. J Biol Chem. Nov. 13, 2015;290(46):27582-93. doi: 10.1074/jbc.M114.636027. Epub Sep. 22, 2015.
Notice of Allowance dated May 6, 2013 for U.S. Appl. No. 12/571,342, filed Sep. 30, 2009, 9 pages.
Notice of allowance dated Apr. 11, 2016 for U.S. Appl. No. 14/396,494.
Notice of allowance dated Apr. 27, 2016 for U.S. Appl. No. 14/548,804.
Notice of allowance dated May 6, 2016 for U.S. Appl. No. 14/006,302.
Novak, et al. Assembly of Phenylacetylene-Bridged Silver and Gold Nanoparticle Arrays. J. Am. Chem. Soc. 2000; 122:3979-3980.
Novak, et al. Nonlinear Optical Properties of Molecularly Bridged Gold Nanoparticle Arrays. J. Am. Chem. Soc. 2000; 122:12029-12030.
Office action dated Jan. 30, 2015 for U.S. Appl. No. 13/834,521.
Office action dated Feb. 7, 2002 for U.S. Appl. No. 09/731,366.
Office action dated Feb. 16, 2011 for U.S. Appl. No. 12/571,342.
Office action dated Feb. 16, 2012 for U.S. Appl. No. 12/571,342.
Office action dated Feb. 23, 2004 for U.S. Appl. No. 09/731,366.
Office action dated Mar. 24, 2008 for U.S. Appl. No. 11/327,199.
Office action dated Mar. 30, 2009 for U.S. Appl. No. 11/327,199.
Office action dated Apr. 14, 2015 for U.S. Appl. No. 13/834,809.
Office action dated Apr. 21, 2004 for U.S. Appl. No. 09/907,038.
Office action dated Apr. 21, 2015 for U.S. Appl. No. 13/838,340.
Office action dated Apr. 21, 2015 for U.S. Appl. No. 13/838,491.
Office action dated Jun. 18, 2007 for U.S. Appl. No. 11/327,199.
Office action dated Aug. 25, 2003 for U.S. Appl. No. 09/907,035.
Office action dated Sep. 10, 2004 for U.S. Appl. No. 09/731,366.
Office action dated Sep. 15, 2015 for U.S. Appl. No. 13/834,521.
Office action dated Sep. 20, 2005 for U.S. Appl. No. 10/467,098.
Office action dated Oct. 2, 2012 for U.S. Appl. No. 12/571,342.
Office action dated Oct. 23, 2003 for U.S. Appl. No. 09/731,366.
Office action dated Oct. 28, 2002 for U.S. Appl. No. 09/731,366.
Office action dated Nov. 3, 2006 for U.S. Appl. No. 10/970,754.
Office action dated Nov. 20, 2002 for U.S. Appl. No. 09/907,035.
Oral Abstracts from the Society of Biomolecular Sciences 14th Annual Conference and Exhibition: St. Louis, Missouri Apr. 6-10, 2008. J. Biomol Screen 2008 13: 692. DOI: 10.1177/1087057108322219.
Oudar, et al. Hyperpolarizabilities of the nitroanilines and their relations to the excited state dipole moment. J. Chem. Phys. 1977; 66. 2664-2668.
Oudar, et al. Optical nonlinearities of conjugated molecules. Stilbene derivatives and highly polar aromatic compounds. J. Chem. Phys. 1977; 67(2):446-457.
Paige, et al. Estrogen receptor (ER) modulators each induce distinct conformational changes in ER alpha and ER beta. Proc Natl Acad Sci U S A. Mar. 30, 1999;96(7):3999-4004.
Paszti, et al. Sum frequency generation vibrational spectroscopy studies of protein adsorption on oxide-covered Ti surfaces. Journal of Physical Chemistry B. 2004; 108:7779-7787.
Peleg, et al. Nonlinear optical measurement of membrane potential around single molecules at selected cellular sites. Proc Natl Acad Sci U S A. Jun. 8, 1999;96(12):6700-4.
Pitchford, et al. Direct, real-time detection of kinae type II inhibitors using second harmonic generation (SHG) detection. 2011. Poster T380. Retrieved Apr. 18, 2012. www.labautopedia.com/mw/images/T380posterSBS2011.jpg.
Polizzi, et al. (2004). Ellipsometric approach for the real-time detection of label-free protein absroption by second harmonic generation. Journal of the American Chemical Society. 2004; 126:5001-5007.
Rajagopalan, et al. Interaction of dihydrofolate reductase with methotrexate: ensemble and single-molecule kinetics. Proc Natl Acad Sci U S A. Oct. 15, 2002;99(21):13481-6. Epub Oct. 1, 2002.
Reider, et al. Second-order Nonlinear Optical Effects at Surfaces and Interfaces in Photonic Probes of Surfaces. Halevia, P., editor. Elsevier Science, Amsterdam. Chapter 9. 1995. 415-478.
Request for Continued Examination filed on Jan. 13, 2009 for U.S. Appl. No. 11/327,199, filed Jan. 5, 2006, 6 pages.
Request for Continued Examination filed on Jul. 16, 2012 for U.S. Appl. No. 12/571,342, filed Sep. 30, 2009, 10 pages.
Response to Non-Final Office Action filed on Apr. 1, 2013 for U.S. Appl. No. 12/571,342, filed Sep. 30, 2009, 9 pages.
Response to Non-Final Office Action filed on Aug. 18, 2011 for U.S. Appl. No. 12/571,342, filed Sep. 30, 2009, 6 pages.

(56) References Cited

OTHER PUBLICATIONS

Response to Non-Final Office Action filed on Dec. 14, 2007 for U.S. Appl. No. 11/327,199, filed Jan. 5, 2006, 8 pages.
Rinuy, et al. Second harmonic generation of glucose oxidase at the air/water interface. Biophysial Journal. 1999; 77:3350-3355.
Salafsky, et al. A second-harmonic-active unnatural amino acid as a structural probe of biomolecules on surfaces. J. Phys. Chem. B, 2008, 112 (47), pp. 15103-15107.
Salafsky, et al. Architecture and function of membrane proteins in planar supported bilayers: A study with photosynthetic reaction centers Biochemistry. 1996; 35(47):14773-14781.
Salafsky, et al. Protein absorption at interfaces detected by second-harmonic generation. Journal of Physical Chemistry B. 2000; 104:7752-7755.
Salafsky, et al. Protein absorption at interfaces detected by second-harmonic generation. J. Phys. Chem. B. 2004; 108(10):3376. Additions and Corrections.
Salafsky, et al. Second Harmonic Spectroscopy: Detection and Orientation of Molecules at a Biomembrane Interface. Chemical Physics Letters 2000; 319:435-439.
Salafsky, et al. SHG labels for detection of molecules by second harmonic generation. Chemical Physics Letters. 2001; 342:485-491.
Salafsky, J. (Apr. 2008). "Second-Harmonic Generation (SHG) for Identification of Allosteric D & Conformation-Specific Compounds" PowerPoint Presentation presented to SBS, 30 pages.
Salafsky, J. (Apr. 15, 2009). "Detection Method for Conformational Change Second-Harmonic Generation Provides a Molecular-Level, Functional Readout in Real Time" Gen Eng & Biotech News, 2 pages.
Salafsky. Detection of protein conformational change by optical second-harmonic generation. J Chem Phys. Aug. 21, 2006;125(7):074701.
Salafsky. Second-harmonic generation as a probe of conformational change in molecules. Chemical Physics Letters. 2003; 381(5):705-709.
Salafsky. Second-harmonic generation for studying structural motion of biological molecules in real time and space. Phys Chem Chem Phys. Nov. 14, 2007;9(42):5704-11. Epub Sep. 7, 2007.
Samanta, et al. Excited state dipole moment of PRODAN as determined from transient dielectric loss measurements. Journal of Physical Chemistry A. 2000; 104:8972-8975.
Seok, et al. Topology of allosteric regulation of lactose permease. Proc Natl Acad Sci U S A. Dec. 9, 1997;94(25):13515-9.
Shen. Optical Second Harmonic Generation at Interfaces. Annual Review of Physical Chemistry. 1989; 40(1):327-350.
Shen. The Principles of Nonlinear Optics, John Wiley & Sons, New York. 1984.
Shen.. Surface properties probed by second-harmonic and sum-frequency generation. Nature. 1989; 337: 20 519-525.
Singer, et al. Measurements of molecular second-order optical susceptibilities using dc-induced second harmonic generation. J. Chem. Phys. 1981; 75:3572-3580.
Summerer, et al. A genetically encoded fluorescent amino acid. Proc Natl Acad Sci U S A. Jun. 27, 2006;103(26):9785-9. Epub Jun. 19, 2006.
Theodossiou, et al.Thermally Induced Irreversible Conformational Changes in Collagen Probed by Optical Second Harmonic Generation and Laser-induced Fluorescence, 2002; 17:34-41.
Vance, et al. Enormous Hyper-Rayleigh Scattering from Nanocrystalline Gold Particle Suspensions. J. Phys. Chem. B. 1999; 102:10091-93.
Wang, et al. In situ, nonlinear optical probe of Surfactant Adsorption on the Surface of Microparticles in Colloids. Langmuir 2000, 16, 2475-2481.
Wang, et al. Polarity of liquid interfaces by second harmonic generation spectroscopy, 1997, J Phys Chem A, 101, 713-718.
Weidner, et al. Sum frequency generation and solid-state NMR study of the structure, orientation, and dynamics of polystyrene-adsorbed peptides. Proc Natl Acad Sci U S A. Jul. 27, 2010;107(30):13288-93. doi: 10.1073/pnas.1003832107. Epub Jul. 13, 2010.
Yang, et al. Surface second harmonic generation (SSHG)—a new scheme for immunoassay. Proceedings of the SPIE. 1996; 2676:290-296. http://dx.doi.org/10.1117/12.238808.
International search report and written opinion dated Jun. 23, 2016 for PCT/US2016/025751.
Martin, et al. A novel approach to the discovery of small-molecule ligands of CDK2. Chembiochem. Sep. 24, 2012;13(14):2128-36. doi: 10.1002/cbic.201200316. Epub Aug. 14, 2012.
Matar, et al. Second Harmonic Generation, a new approach for analyzing the interfacial properties of a short tryptophan-rich peptide. Chemical Physics Letters. vol. 500, pp. 161-166, (2010).
McGuinness, et al. Direct, Real-time Detection of Protein Conformation: Revealing Therapeutic Opportunities Using Second Harmonic Generation (SHG) Detection. Biodesy, LLC. Poster M143. Mar. 18-21, 2011.
NSF. SBIR Phase I: Development of a Conformational Screen for Rapidly Identifying Kinase Inhibitor Type Using SHG. NSF SBIR grant abstract. 2011.
Pitchford, et al. Direct, Real-time Detection of Kinase Type II Inhibitors Using Second Harmonic Generation (SHG) Detection. Biodesy, LLC. Poster T380. Mar. 17, 2011.
Reider et al. Coherence artifacts in second harmonic microscopy. Applied Physics B: Lasers & Optics. 68(3):343 (1999). 5 pages.
Salafsky, et al. Real-time measurement of protein conformational change in key therapeutic targets: application to Abl kinase and mutant Ras. Biodesy, LLC. SLAS2012 talk abstract. Nov. 2011.
Salafsky. Real-time measurement of protein conformational change in key therapeutic targets: applications to Abl-kinase and mutant Ras. Biodesy, LLC. SLAS Conference. PPT presentation. Feb. 7, 2012.
Salafsky. Second-Harmonic Generation (SHG) for Identification of Allosteric and Conformation-Specific Compounds. Journal of Biomolecular Screening. 2008; 13(7):697.
Simpson et al. An SHG Magic Angle: Dependence of Second Harmonic Generation Orientation Measurements on the Width of the Orientation Distribution. J Am Chem Soc 21(11):2635-2636 (Mar. 6, 1999). DOI: https://doi.org/10.1021/ja983683f.
Vanzi, et al., Protein conformation and molecular order probed by second-harmonic-generation microscopy, Journal of Biomedical Optics, Jun. 18, 2012, 17(6):060901, 8 Pages.
Wartchow, et al. Assaying protein conformational change in real time—A novel approach for target-based drug discovery. Biodesy, LLC. SLAS2012 Roche poster. Feb. 6-8, 2012.

* cited by examiner

METHODS FOR DETERMINING PROTEIN STRUCTURE USING A SURFACE-SELECTIVE NONLINEAR OPTICAL TECHNIQUE

CROSS-REFERENCE

This application claims the benefit of U.S. Provisional Application No. 62/142,314, filed Apr. 2, 2015, and also claims the benefit of U.S. Provisional Application No. 62/148,649, filed Apr. 16, 2015, both of which applications are incorporated herein by reference in their entirety.

BACKGROUND

Second harmonic generation (SHG) is a nonlinear optical process which may be configured as a surface-selective detection technique that enables detection of binding interactions and conformational change in proteins and other biological targets using second harmonic-active labels attached to the target molecules (see, for example, U.S. Pat. Nos. 6,953,694, and 8,497,073). To date these methods have been applied to detect ligand-induced conformational changes in a variety of systems and to distinguish ligands by the type of conformation they induce upon binding (Salafsky, J. S. (2001), "'SHG-labels' for Detection of Molecules by Second Harmonic Generation", Chemical Physics Letters 342, 485-491; Salafsky, J. S. (2003), "Second-Harmonic Generation as a Probe of Conformational Change in Molecules", Chemical Physics Letters 381, 705-709; Salafsky, J. S. (2006), "Detection of Protein Conformational Change by Optical Second-Harmonic Generation", Journal of Chemical Physics 125; Moree, B., et al. (2015), "Small Molecules Detected by Second Harmonic Generation Modulate the Conformation of Monomeric α-Synuclein and Reuce Its Aggregation in Cells", J. boil. Chem. 290(46); 27582-27593; Moree, et al. (2015), "Protein Conformational Changes are Detected and Resolved Site Specifically by Second-Harmonic Generation", Biophys. J. 109:806-815). Examples include distinguishing between type I vs. type II kinase inhibitors, such as imatinib and dasatinib, which bind to the protein to induce inactive and active conformations, respectively.

SHG and the related technique sum-frequency generation (SFG) have been used in the past to study the orientation of dye molecules at an interface (Heinz T., et al., (1983), "Determination of Molecular Orientation of Monolayer Adsorbates by Optical Second-Harmonic Generation", Physical Review A 28(3):1883-1885; Heinz, T, (1991) Second-Order Nonlinear Optical Effects at Surfaces and Interfaces", in *Nonlinear Surface Electromagnetic Phenomena* (Stegeman, H. P. a. G. ed.), Elsevier, Amsterdam, pp 353-416). In these measurements, the components of the nonlinear susceptibility ($\chi^{(2)}$) of the labeled interface are determined using polarized light. Details of the molecular orientation distribution for the dye molecules at the interface can then be inferred using the experimentally determined values for $\chi^{(2)}$ and assumptions regarding the degree of orientation of the dye molecules within the plane of the interface, the relative magnitude of the components of hyperpolarizability ($\alpha^{(2)}$) of the dye molecules in the molecular frame of reference, etc.

The field of protein and biomolecular structure determination is highly developed but there remains a need for a sensitive and rapid measure of conformational change and structure in real time and in solution. Most information about protein structure and dynamics has come mainly from X-ray crystallography and NMR studies, but these techniques are relatively labor and material intensive, slow, or provide only a static snapshot of protein structure.

The presently disclosed methods, devices, and systems for determining protein structure using surface-selective nonlinear optical techniques address these unmet needs. In some embodiments, determination of protein structure in a high-throughput format is enabled through the use of novel device designs and mechanisms for rapid, precise, and interchangeable positioning of substrates (comprising the tethered or immobilized biological targets to be analyzed) with respect to the optical system used to deliver excitation light, and which at the same time ensure that efficient optical coupling between the excitation light and the substrate surface is maintained. One preferred format for high-throughput optical interrogation of biological samples is the glass-bottomed microwell plate. The systems and methods disclosed herein provide mechanisms for coupling the high intensity excitation light required for SHG and other nonlinear optical techniques to a substrate, e.g. the glass substrate in a glass-bottomed microwell plate, by means of total internal reflection in a manner that is compatible with the requirements for a high-throughput analysis system.

SUMMARY

Disclosed herein are methods for determining protein structure in solution, the methods comprising: (a) tethering protein molecules to a surface under a first set of experimental conditions, wherein the protein molecules are labeled at one or more known positions with one or more nonlinear-active labels; (b) illuminating the tethered protein molecules of step (a) with excitation light of at least one fundamental frequency, wherein the excitation light is provided by at least one light source; (c) detecting a first physical property of light generated by the one or more nonlinear-active labels as a result of the illumination in step (b); (d) tethering the protein molecules on a surface under at least a second set of experimental conditions; (e) illuminating the tethered protein molecules of step (d) with excitation light of at least one fundamental frequency; (f) detecting at least a second physical property of light generated by the one or more nonlinear-active labels as a result of the illumination in step (e); and (g) comparing the at least second physical property of the light detected in step (f) to the first physical property of the light detected in step (c) to determine a relative orientation of the one or more nonlinear-active labels in the tethered protein molecules.

In some embodiments, the methods further comprising globally fitting data for the relative orientation of the one or more nonlinear-active labels to a structural model of the protein molecule, wherein the structural model is based on known positions of the one or more nonlinear-active labels within the protein molecule.

In some embodiments, the methods further comprise repeating steps (a) through (f) for at least two different nonlinear-active label-protein conjugates, wherein the nonlinear-active labels are attached to at least two different sites on the protein molecule. In some embodiments, the at least two different nonlinear-active label-protein conjugates each comprise a single-site cysteine. In some embodiments, the nonlinear-active labels are nonlinear-active unnatural amino acids. In some embodiments, the at least second physical property of light is different from the first physical property of light. In some embodiments, the first and the at least second physical properties of light possess the same polarization but are of different magnitudes or intensities. In some embodiments, the first and at the least second physical properties of light possess different polarizations. In some embodiments, the nonlinear-active unnatural amino acid is Aladan or a derivative of naphthalene. In some embodiments, the methods further comprise incorporating x-ray crystallographic data for the protein into the structural model of the protein molecule. In some embodiments, the protein molecules are labeled at two or more known positions. In some embodiments, the protein molecules are labeled at three or more known positions.

In some embodiments, steps (d) through (f) are repeated for at least a third set of experimental conditions. In some embodiments, steps (d) through (f) are repeated for at least a fourth set of experimental conditions. In some embodiments, the first set of experimental conditions comprises applying a first electric field of a first electric field strength to the tethered protein molecules, and the at least second set of experimental conditions comprises applying an at least second electric field of an at least a second electric field strength to the tethered protein molecules. In some embodiments, the first electric field and the at least second electric field are direct current (DC) fields. In some embodiments, the first electric field and the at least second electric field are alternating current (AC) fields. In some embodiments, the first electric field is a direct current (DC) field and the at least second electric field is an alternating current (AC) field. In some embodiments, the first electric field is an alternating current (AC) field and the at least second electric field is a direct current (DC) field. In some embodiments, the first electric field and the at least second electric field are applied using an array of electrodes fabricated on the surface. In some embodiments, the array of electrodes is a circular array as illustrated in FIG. 9.

In some embodiments, the first set of experimental conditions comprises tethering the protein molecules using a His-tag attached to the N-terminus, and the at least second set of experimental conditions comprises tethering the protein molecules using a His-tag attached to the C-terminus. In some embodiments, the first set of experimental conditions comprises tethering the protein molecules using a first His-tag selected from the group consisting of 2×His, 4×His, 6×His, 8×His, 10×His, 12×His, and 14×His, and the at least second set of experimental conditions comprises tethering the protein molecules using an at least second His-tag that differs in length from the first His-tag.

In some embodiments, the first set of experimental conditions comprises tethering the protein molecules using a first assay buffer, and the at least second set of experimental conditions comprises tethering the protein molecules using an at least second assay buffer that differs from the first assay buffer. In some embodiments, the difference between the first assay buffer and the at least second assay buffer is selected from the group consisting of ionic strength, pH, detergent concentration, calcium ion (Ca2+) concentration, magnesium ion (Mg2+) concentration, polyethylene glycol concentration, and any combination thereof.

In some embodiments, the difference between the first set of experimental conditions and the at least second set of experimental conditions comprises contacting the tethered protein molecules with at least a first ligand that is known to bind to and induce conformational change in the protein molecules.

In some embodiments, the one or more nonlinear-active labels located at the one or more known positions are the same. In some embodiments, the one or more nonlinear-active labels located at the one or more known positions are different. In some embodiments, the one or more nonlinear-active labels are second harmonic (SH)-active labels. In some embodiments, the one or more nonlinear-active labels are sum frequency (SF)-active labels. In some embodiments, the one or more nonlinear active labels are difference frequency (DF)-active labels.

In some embodiments, the illuminating steps comprise adjusting the polarization of excitation light of at least one fundamental frequency. In some embodiments, the detecting in steps (c) and (e) comprise adjusting the polarization of the light generated by the one or more nonlinear-active labels that reaches a detector. In some embodiments, the first and at least second physical properties of light are intensity or polarization.

Also disclosed herein are methods for determining the absolute orientation of a nonlinear-active label attached to a tethered protein, the method comprising: (a) detecting a physical property of light generated by a nonlinear-active surface as a result of illumination with excitation light of at least one fundamental frequency, wherein detection is performed using two different polarization states of the excitation light; (b) detecting a physical property of light generated by a nonlinear-active labeled protein tethered in an oriented fashion on a non-labeled surface, wherein the light is generated as a result of illumination with excitation light of the at least one fundamental frequency, and wherein detection is performed using two different polarization states of the excitation light; (c) detecting a physical property of light generated by a nonlinear-active labeled protein tethered in an oriented fashion on a nonlinear-active labeled surface, wherein the light is generated as a result of illumination with excitation light of the at least one fundamental frequency, and wherein detection is performed using the two different polarization states of the excitation light; and (d) determining the absolute orientation of the nonlinear-active label attached to the tethered protein by comparing the physical property of the light in step (a), the physical property of the light detected in step (b), and the physical property of the light detected in step (c).

In some embodiments, the excitation light is directed to the surface in such a way that it is totally internally reflected from the surface. In some embodiments, a first polarization state of the excitation light comprises p-polarization relative to its plane of incidence, and a second polarization state of the excitation light comprises s-polarization relative to its plane of incidence. In some embodiments, the methods further comprise detecting a physical property of the light generated in steps (a), (b), and (c) using excitation light of more than two different polarization states.

In some embodiments, the nonlinear-active labeled surface is prepared using covalent carbodiimide coupling of a carboxylated nonlinear-active label to an aminosilane-functionalized glass substrate surface. In some embodiments, the nonlinear-active labeled surface comprises a supported lipid bilayer, and wherein the supported lipid bilayer further comprises an amine- or thiol-containing lipid to which a nonlinear-active label is covalently coupled.

In some embodiments, the nonlinear-active labeled protein is tethered in an oriented fashion on the non-labeled or nonlinear-active labeled surface using covalent carbodiimide coupling of the C-terminus of the protein to an aminosilane-functionalized glass substrate surface. In some embodiments, the nonlinear-active labeled protein is tethered in an oriented fashion on a non-labeled or nonlinear-active labeled surface comprising a supported lipid bilayer, and wherein the nonlinear-active labeled protein is inserted into the supported lipid bilayer or attached to an anchor molecule that is inserted into the supported lipid bilayer.

In some embodiments, the nonlinear-active label is a second harmonic (SH)-active label. In some embodiments, the nonlinear-active label is a sum frequency (SF)-active label. In some embodiments, the nonlinear-active label is a difference frequency (DF)-active label.

Disclosed herein are devices comprising: (a) a substrate comprising a first surface that further comprises a plurality of discrete regions, wherein each discrete region further comprises a supported lipid bilayer and a patterned array of electrodes; and (b) a well-forming component bonded to or integrated with the first surface of the substrate so that each discrete region is contained within a single well.

In some embodiments, a plurality of supported lipid bilayers further comprises a nonlinear-active labeled protein. In some embodiments, the plurality of supported lipid bilayers further comprises a nonlinear-active protein that is the same for each. In some embodiments, the plurality of supported lipid bilayers further comprise two or more subsets of supported lipid bilayers, and wherein each subset of supported lipid bilayers comprises a different nonlinear-active protein. In some embodiments, the substrate is fabricated from an optically-transparent material selected from the group consisting of glass, fused-silica, polymer, or any combination thereof. In some embodiments, the patterned array of electrodes comprises an array of two or more electrodes patterned on the substrate surface surrounding the supported lipid bilayer. In some embodiments, the patterned array of electrodes comprises an array of two or more electrodes patterned on the walls of each well of the well-forming unit. In some embodiments, the patterned array of electrodes comprises at least one electrode patterned on a lid that seals each well. In some embodiments, the well-forming unit comprises 96 wells. In some embodiments, the well-forming unit comprises 384 wells. In some embodiments, the well-forming unit comprises 1,536 wells. In some embodiments, the device further comprises an array of prisms integrated with a second surface of the substrate and configured to deliver excitation light to the first surface of the substrate so that it is totally internally reflected from the first surface.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in its entirety. In the event of a conflict between a term herein and a term in an incorporated reference, the term herein controls.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 10A: top axonometric view. FIG. 10B: bottom axonometric view.

FIG. 11A: top axonometric view. FIG. 11B: bottom axonometric view.

FIG. 13A: Data for cysteine-labeled DHFR mutants tethered to a Ni/NTA-doped supported lipid bilayer by means of an N-terminal His-tag. FIG. 13B: Data for cysteine-labeled DHFR mutants tethered to a Ni/NTA-doped supported lipid bilayer by means of a C-terminal His-tag.

FIG. 14A: Data for cysteine-labeled DHFR mutants tethered to a Ni/NTA-doped supported lipid bilayer by means of an N-terminal His-tag. FIG. 14B: Data for cysteine-labeled DHFR mutants tethered to a Ni/NTA-doped supported lipid bilayer by means of a C-terminal His-tag.

DETAILED DESCRIPTION

The systems and methods disclosed herein relate to the field of biomolecular structure and dynamics determination. Methods for determining the relative and/or absolute orientation of second harmonic-active labels (or other nonlinear-active labels, e.g. sum frequency-active or difference frequency-active labels) attached to proteins or other biological molecules, and for determining molecular structures therefrom are described. In addition, devices and systems are described which are suitable for high throughput analysis of molecular orientation or molecular structure. In some aspects of the present disclosure, methods and systems are described for determining orientation, conformation, structure, or changes in orientation, conformation, or structure of biological entities in response to contacting the biological entities with one or more test entities. As used herein, determining orientation, conformation, structure, or changes thereof may involve measurement of a nonlinear optical signal which is related to and/or proportional to the average orientation of a nonlinear-active label or tag. As used herein, "high throughput" refers to the ability to perform rapid analysis of molecular orientation, conformation, structure, or changes thereof for a plurality of biological entities optionally contacted with one or more test entities, or to the ability to perform rapid analysis of molecular orientation, conformation, structure, or changes thereof for one or more biological entities optionally contacted with a large plurality of test entities, or to any combination of these modalities.

In general, the methods, devices, and systems disclosed rely on the use of second harmonic generation (SHG), or the related nonlinear optical techniques of sum frequency generation (SHG) or difference frequency generation (DFG), for the determination of molecular orientation, conformation, structure, or changes thereof. In these methods, polarization-dependent measurements are used to determine the components of the nonlinear susceptibility, $\chi^{(2)}$, of protein molecules (or other biological molecules) oriented at a surface or interface and labeled at one or more specific sites by a hyperpolarizable moiety according to methods known to those of skill in the art. The components of $\chi^{(2)}$ in turn are related to the molecular orientational distribution at each label site through a model. By measuring at least two different components of $\chi^{(2)}$ under two or more different sets of experimental conditions (defined below) using labels placed at one or more different sites in the protein, one can use the resulting information on relative orientation of the labels to develop a model of protein structure and detect changes thereof using SHG or related nonlinear optical techniques.

Figure 1:
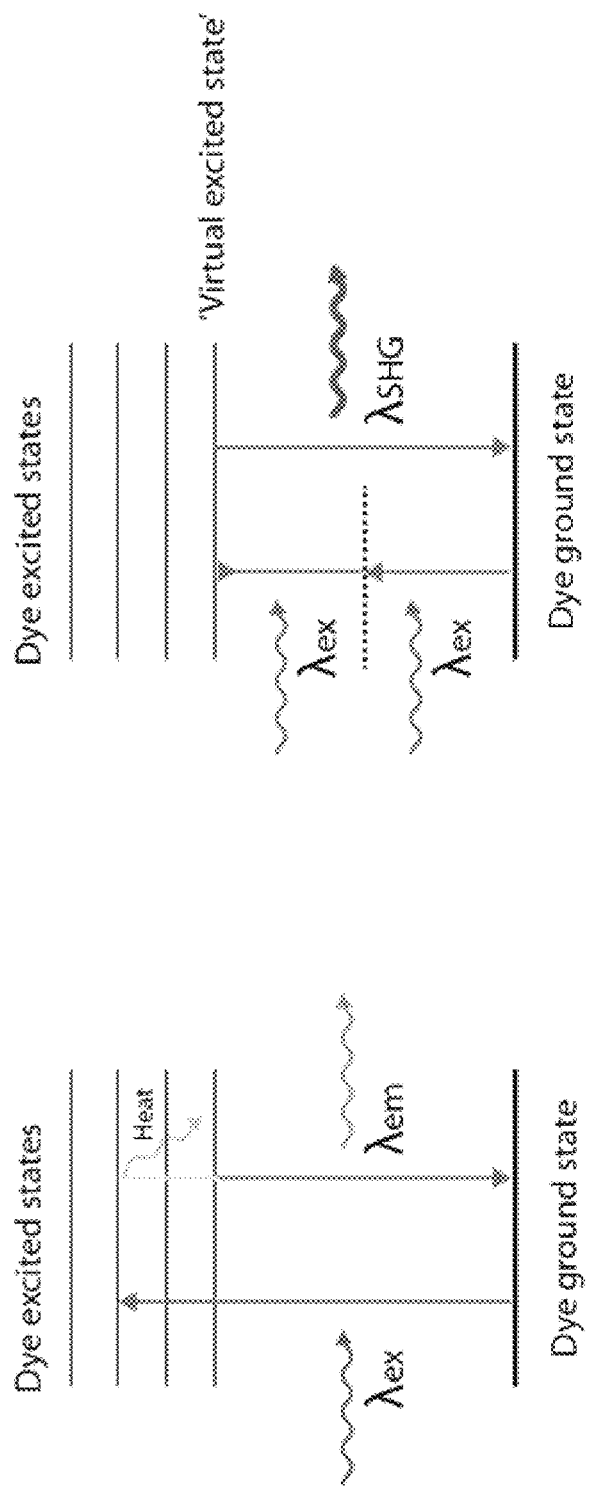
FIG. 1A provides a schematic illustration of the energy level diagrams for fluorescence (an absorption/emission process).
FIG. 1B provides a schematic illustration of the energy level diagrams for second harmonic generation (a two photon scattering process).

Detection of Orientation, Conformation, and Structure Using Second Harmonic Generation Second harmonic generation, in contrast to the more widely used fluorescence-based techniques (FIG. 1A), is a nonlinear optical process in which two photons of the same excitation wavelength or frequency interact with a nonlinear material and are re-emitted as a single photon having twice the energy, i.e. twice the frequency and half the wavelength, of the excitation photons (FIG. 1B). Second harmonic generation only occurs in nonlinear materials lacking inversion symmetry (i.e. in non-centrosymmetric materials), and requires a high intensity excitation light source. It is a special case of sum frequency generation, and is related to other nonlinear optical phenomena such as difference frequency generation. Throughout this disclosure, the terms SHG, SFG, and DFG are used interchangeably, as will be understood by those of skill in the art.

Second harmonic generation and other nonlinear optical techniques can be configured as surface-selective detection techniques because of their dependence on the orientation of the nonlinear-active species. Tethering of the nonlinear-active species to a surface, for example, can create a net, average degree of orientation that is absent when molecules are able to undergo free diffusion in solution. An equation commonly used to model the orientation-dependence of nonlinear-active species at an interface is:

$$\chi^{(2)} = N_s \langle \alpha^{(2)} \rangle$$

where $\chi^{(2)}$ is the nonlinear susceptibility, $N_s$ is the total number of nonlinear-active molecules per unit area at the interface, and $\langle \alpha^{(2)} \rangle$ is the average orientation of the nonlinear hyperpolarizability ($\alpha^{(2)}$) of these molecules. The intensity of SHG is proportional to the square of the nonlinear susceptibility, and is thus dependent on both the number of oriented nonlinear-active species at the interface and their orientational distribution; changes in this orientational distribution, whether spatial or temporal, change the SHG intensity.

Second harmonic generation and other nonlinear optical techniques may be rendered additionally surface selective through the use of total internal reflection as the mode for delivery of the excitation light to the optical interface (or surface) on which nonlinear-active species have been tethered or immobilized. Total internal reflection of the incident excitation light creates an "evanescent wave" at the interface, which may be used to selectively excite only nonlinear-active labels that are in close proximity to the surface, i.e. within the spatial decay distance of the evanescent wave, which is typically on the order of tens of nanometers. Total internal reflection may also be used to excite fluorescence in a surface-selective manner, for example to excite a fluorescence donor attached to the optical interface, which then transfers energy to a suitable acceptor molecule via a fluorescence resonance energy transfer (FRET) mechanism. In the present disclosure, the evanescent wave generated by means of total internal reflection of the excitation light is preferentially used to excite a nonlinear-active label or molecule. The efficiency of exciting nonlinear active species in the nonlinear-active processes described herein depends strongly on their average orientation relative to the surface. For example, if no net average orientation of the nonlinear active species exists, there will be no SHG signal.

Figure 2:
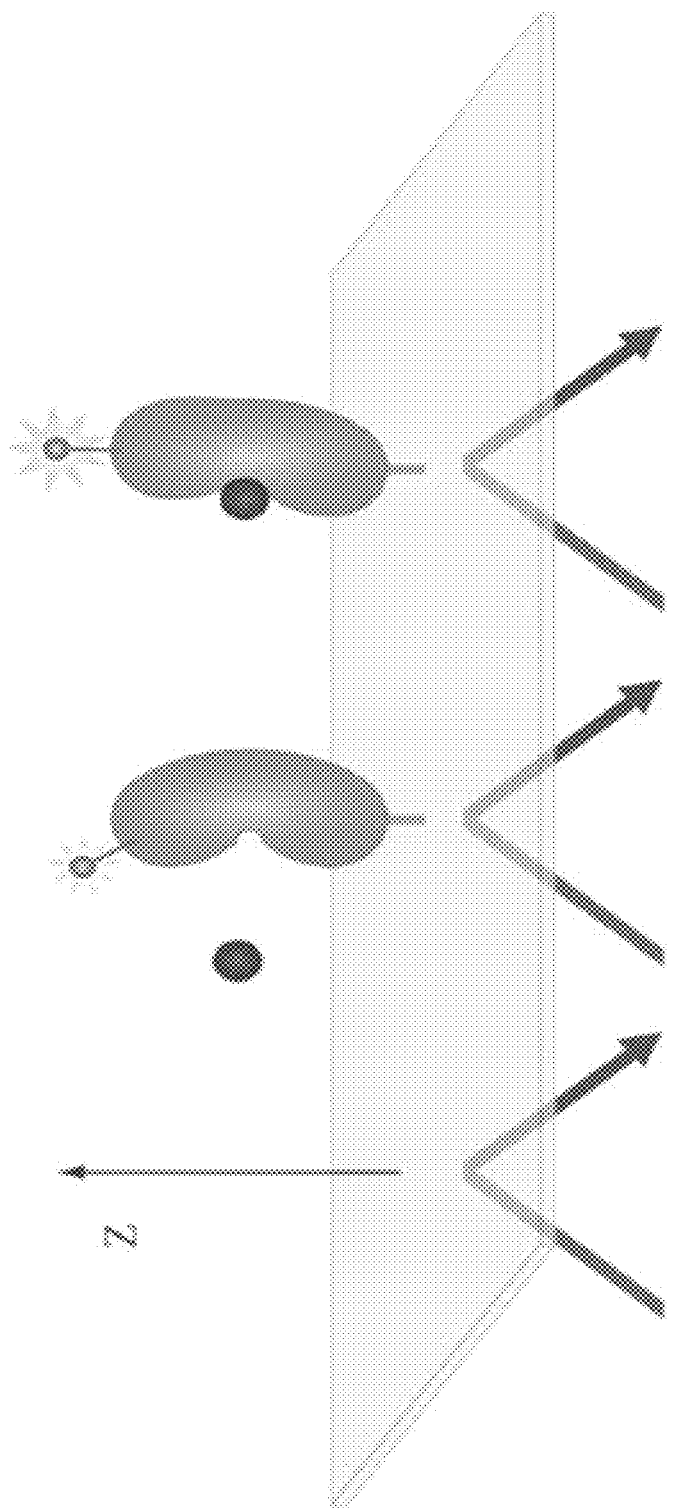
FIG. 2 provides a schematic illustration of a conformational change in a protein (labeled with a nonlinear-active moiety) which is induced by binding of a ligand, and its impact on the orientation of a nonlinear-active label relative to an optical interface (Z-axis) to which the protein is attached.

This surface selective property of SHG and other nonlinear optical techniques (e.g. sum frequency generation and difference frequency generation) can be exploited to detect orientation, conformation, structure, and change thereof in biological molecules tethered at interfaces. For example, conformational change in a receptor molecule due to binding of a ligand, might be detected using a nonlinear-active label or moiety wherein the label is attached to or associated with the receptor such that the conformational change leads to a change in the orientation with respect to the interface (FIG. 2), and thus to a change in a physical property of the nonlinear optical signal (e.g. a change in signal intensity or polarization). In the past, the use of surface-selective nonlinear optical techniques has been confined mainly to applications in physics and chemistry, since relatively few biological samples are intrinsically non-linearly active. Recently, the use of second harmonic active labels ("SHG labels") has been introduced, allowing virtually any molecule or particle to be rendered highly non-linear active. The first example of this was demonstrated by labeling the protein cytochrome c with an oxazole dye and detecting the protein conjugate at an air-water interface with second harmonic generation (Salafsky, J., "'SHG-labels' for Detection of Molecules by Second Harmonic Generation", Chem. Phys. Lett. 342(5-6):485-491 (2001)).

Surface-selective nonlinear optical techniques are also coherent techniques, meaning that the fundamental and nonlinear optical light beams have wavefronts that propagate through space with well-defined spatial and phase relationships. The use of surface-selective nonlinear optical detection techniques for analysis of structure and conformation of biological molecules or other biological entities has a number of inherent advantages over other optical approaches, including: i) sensitive and direct dependence of the nonlinear signal on the orientation of the nonlinear-active species, thereby conferring sensitivity to orientation and conformational change; (ii) higher signal-to-noise (lower background) than fluorescence-based detection since the nonlinear optical signal is generated only at surfaces that create a non-centrosymmetric system, i.e. the technique inherently has a very narrow "depth-of-field"; (iii) as a result of the narrow "depth of field", the technique is useful when measurements must be performed in the presence of a overlaying solution containing free (i.e., not tethered to the surface) nonlinear-active species, e.g. where a binding process might be obviated or disturbed by a separation or rinse step. This aspect of the technique may be particularly useful for performing equilibrium binding measurements, which require the presence of bulk species, or kinetics measurements where the measurements are made over a defined period of time; (iv) the technique exhibits lower photobleaching and heating effects than those that occur in fluorescence, due to the fact that the two-photon absorption cross-section is typically much lower than the one-photon absorption cross-section for a given molecule, and that SHG (and sum frequency generation or difference frequency generation) involves scattering, not absorption; (v) minimal collection optics are required and higher signal to noise is expected since the fundamental and nonlinear optical beams (e.g., second harmonic light) have well-defined incoming and outgoing directions with respect to the interface; this is particularly advantageous compared to fluorescence-based detection, as fluorescence emission is isotropic and there may also be a large fluorescence background component to detected signals arising from out-of-focal plane fluorescent species; (vi) the signals arising from SHG, SFG or DFG provide an instantaneous, real-time means of studying a molecule's structure, conformation or change thereof such as occurs, for example, upon ligand binding. This property may be very useful in the disclosed methods for obtaining real-time "movies" of proteins undergoing structural changes as part of their function in real time.

Determination of Protein Structure & Dynamics

Polarization Measurements:

The components of $\chi^{(2)}$ may be measured in the laboratory frame of reference using polarized excitation light of at least one fundamental frequency. Some light sources, e.g. some lasers, produce light of a fundamental frequency that is substantially polarized. In some embodiments, the polarization of the excitation light may be further defined and/or adjusted using one or more optical polarizers, wave plates, etc. Typically, the plane of incidence of the polarized light (i.e. the plane defined by the propagation direction of the excitation light and a vector perpendicular to the plane of the substrate or reflecting surface) will be the X-Z plane of the laboratory coordinate system illustrated in FIG. 3. Polarized light having its electric field vector parallel to the plane of incidence is called p-polarized light. Polarized light having its electric field vector perpendicular to the plane of incidence is called s-polarized light. In some embodiments, the polarization of the detected second harmonic light generated by excitation of a nonlinear-active moiety may also be defined and/or adjusted using one or more optical polarizers, wave plates, etc. As outlined above, by measuring at least two different components of $\chi^{(2)}$ under two or more different sets of experimental conditions using labels placed at one or more different sites in the protein tethered or immobilized in an oriented fashion on the optical interface (i.e. the surface plane in FIG. 3), one can use the resulting information on relative orientation of the labels to develop a model for protein structure and detect changes thereof using SHG or related nonlinear optical techniques.

Proteins Labeled with Nonlinear-Active Moieties:

Attachment of nonlinear-active labels to proteins may be accomplished by any of a variety of techniques, as is well known to those of skill in the art. Specific non-limiting examples of suitable label attachment techniques will be described in more detail below.

In some embodiments, one or more nonlinear-active labels may be attached to one or more different positions within the same individual protein molecule. In some embodiments, the one or more nonlinear-active labels may be attached to one or more different positions (e.g. sites) in different molecules of the same protein, i.e. to create a family of proteins comprising different versions of the labeled protein. In some embodiments, the number of labeling sites at which the protein (or family of proteins) is labeled may be at least 1 site, at least 2 sites, at least 3 sites, at least 4 sites, at least 5 sites, at least 6 sites, at least 7 sites, at least 8 sites, at least 9 sites, at least 10 sites, or more. In other embodiments, the nonlinear-active label may be attached to different single-site cysteine mutants or variants of the same protein, or nonlinear-active unnatural amino acids (e.g., Aladan or other naphthalene derivatives) may be attached to a family of mutants or variants at one or more sites. Such proteins can be engineered, naturally occurring, made using in vitro translation methods, expressed in vivo, and in general created through any of the various methods known to those skilled in the art.

In some embodiments, the SHG measurements may comprise using protein molecules labeled with a single nonlinear-active label. In some embodiments, the SHG measurements may comprise using protein molecules labeled with at least 2 different nonlinear-active labels, at least 3 different nonlinear-active labels, at least 4 different nonlinear-active labels, at least 5 different nonlinear-active labels, at least 6 different nonlinear-active labels, at least 7 different nonlinear-active labels, at least 8 different nonlinear-active labels, at least 9 different nonlinear-active labels, or at least 10 different nonlinear-active labels.

Figure 3:
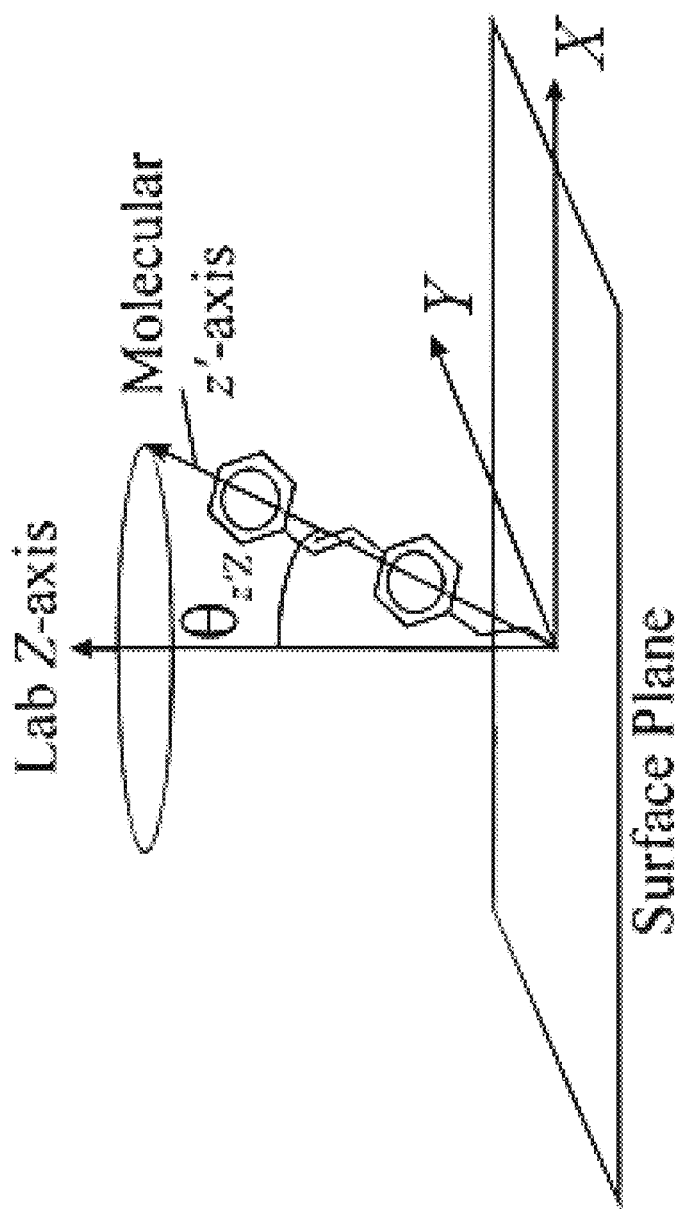
FIG. 3 illustrates the relationship between the laboratory frame of reference (as defined by X, Y, and Z axes) and the molecular frame of reference (as defined by X', Y', and Z' axes). For some nonlinear-active molecules, the hyperpolarizability tensor ($\alpha^{(2)}$) may be dominated by a single component in the molecular frame of reference, i.e., $\alpha^{(2)} = \alpha^{(2)}_{Z'Z'Z'}$.

Experimental Conditions:

As defined herein, "experimental conditions" refer to any set of experimental parameters under which SHG or other nonlinear optical signals are measured, wherein a change in one or more of the experimental parameters in the set of experimental conditions results in a change in the measured values of $\chi^{(2)}$ due to a change in the underlying molecular orientational distribution. In other words, different sets of experimental conditions produce different baseline SHG signal intensities, different polarization dependences, different responses to the same ligand binding event, or any or all of the aforementioned. For example, applying an electric field to proteins attached to a supported lipid bilayer can change the molecules' underlying orientational distribution and thus may change the measured values of $\chi^{(2)}$. Other examples of experimental parameters that may be used to define sets of experimental conditions include, but are not limited to, buffer conditions such as pH, ionic strength, detergent content and concentration, tether attachment site (e.g., through the use of N- or C-terminal His tags), etc. Specifically, the independent values of $\chi^{(2)}$ measured under the different and independent sets of experimental conditions permit one to obtain the underlying molecular orientational distribution in the laboratory frame of reference (FIG. 3). By relating these different laboratory frame measurements to each other, one can determine the relative difference in angle between the nonlinear-active labels positioned at two or more different label sites in the protein frame of reference, along with other parameters of the orientational distribution such as the width of a gaussian distribution used to model the molecular orientational distribution.

In some embodiments, the use of one or more compositions of surfaces to which the labeled proteins are tethered may be used to define different sets of experimental conditions. For example, if supported lipid bilayers are used to tether and orient the labeled proteins, two or more different lipid compositions of the bilayer (for example, with different electrostatic charge densities or different molar lipid doping densities) can be used to create two or more different orientational distributions of the same protein. For example, lipids with head groups bearing different net charges can be used (e.g., zwitterionic, positively, and negatively charged lipid head groups). In some embodiments, it may be advantageous to vary the lipid composition of the supported lipid bilayer by varying, e.g., the number of different lipid components and/or their relative concentrations. Examples of lipid molecules that may be used to form supported lipid bilayers or that may be inserted as major or minor components of the supported lipid bilayer include, but are not limited to, diacylglycerol, phosphatidic acid (PA), phosphatidylethanolamine (PE), phosphatidylcholine (PC), phosphatidylserine (PS), phosphatidylinositol (PI), phosphatidylinositol phosphate (PIP), phosphatidylinositol biphosphate (PIP2), phosphatidylinositol triphosphate (PIP3), ceramide phosphorylcholine (sphingomyelin; SPH), ceramide phosphorylethanolamine (sphingomyelin; Cer-PE), ceramide phosphoryllipid, or any combination thereof. In some embodiments, a lipid molecule comprising a nickel-nitrilotriacetic acid chelate (Ni-NTA) moiety may be used for the purpose of tethering proteins by means of a His tag. For example, the bilayer may incorporate 1,2-dioleoyl-sn-glycero-3-[(N-(5-amino-1-carboxypentyl)iminodiacetic acid)succinyl] (nickel salt) at various molar concentrations.

In some embodiments, the number of different lipid components of the lipid bilayer may range from 1 to 10, or more. In some embodiments, the number of different lipid components may be at least 1, at least 2, at least 3, at least 4, at least 5, at least 6, at least 7, at least 8, at least 9, or at least 10. In some embodiments, the number of different lipid components may be at most 10, at most 9, at most 8, at most 7, at most 6, at most 5, at most 4, at most 3, at most 2, or at most 1.

In some embodiments, the relative percentage of a given lipid component of the lipid bilayer may range from about 0.1% to about 100%. In some embodiments, the relative percentage of a given lipid component may be at least about 0.1%, at least about 0.2%, at least about 0.3%, at least about 0.4%, at least about 0.5%, at least about 1%, at least about 5%, at least about 10%, at least about 20%, at least about 30%, at least about 40%, at least about 50%, at least about 60%, at least about 70%, at least about 80%, at least about 90%, or at least about 100%. In some embodiments, the relative percentage of a given lipid component may be at most about 100%, at most about 90%, at most about 80%, at most about 70%, at most about 60%, at most about 50%, at most about 40%, at most about 30%, at most about 20%, at most about 10%, at most about 5%, at most about 1%, at most about 0.5%, at most about 0.4%, at most about 0.3%, at most about 0.2%, or at most about 0.1%. Those of skill in the art will recognize that the relative percentage of a given lipid component in the lipid bilayer may have any value within this range, e.g. about 12.5%.

If tags such as His tags are used to tether the protein, different lengths of the His-tags (i.e., 6x, 8x, 10x, 12x, etc.) can produce different orientational distributions, and therefore may be used to define different sets of experimental conditions. Moreover, N-terminal vs. C-terminal His-tags generally produce different orientational distributions, and thus may be used to define different sets of experimental conditions that yield different measured values of $\chi^{(2)}$.

In some embodiments, the length of the His tag used to tether a labeled protein to a supported lipid bilayer comprising a lipid having a Ni-NTA moiety attached may range from about 1 His residue to about 20 His residues, or more. In some embodiments, the length of the His tag may be at least 1 His residue, at least 2 His residues, at least 3 His residues, at least 4 His residues, at least 5 His residues, at least 6 His residues, at least 7 His residues, at least 8 His residues, at least 9 His residues, at least 10 His residues, at least 11 His residues, at least 12 His residues, at least 13 His residues, at least 14 His residues, at least 15 His residues, at least 16 His residues, at least 17 His residues, at least 18 His residues, at least 19 His residues, or at least 20 His residues. In some embodiments, the length of the His tag may be at most 20 His residues, at most 19 His residues, at most 18 His residues, at most 17 His residues, at most 16 His residues, at most 15 His residues, at most 14 His residues, at most 13 His residues, at most 12 His residues, at most 11 His residues, at most 10 His residues, at most 9 His residues, at most 8 His residues, at most 7 His residues, at most 6 His residues, at most 5 His residues, at most 4 His residues, at most 3 His residues, at most 2 His residues, or at most 1 His residue.

Furthermore, different buffer conditions, such as different salt concentrations in the same buffer or different buffers, can also change the orientational distributions of the molecules and thus the measured values of $\chi^{(2)}$. In some embodiments, the ionic strength of the buffers used to define different sets of experimental conditions may comprise using monovalent salts (e.g. NaCl, KCl, etc.), divalent salts (e.g. $CaCl_2$, $MgCl_2$, etc.), trivalent salts (e.g. $AlCl_3$), or any combination thereof. In some embodiments, the ionic strength of the buffers used to define different sets of experimental conditions may range from about 0.0 M to about 1 M, or higher. In some embodiments, the ionic strength of the buffer may be at least 0.0 M, at least 0.1 M, at least 0.2 M, at least 0.3 M, at least 0.4 M, at least 0.5 M, at least 0.6 M, at least 0.7 M, at least 0.8 M, at least 0.9 M, or at least 1.0 M. In some embodiments, the ionic strength of the buffer may be at most 1.0 M, at most 0.9 M, at most 0.8 M, at most 0.7 M, at most 0.6 M, at most 0.5 M, at most 0.4 M, at most 0.3 M, at most 0.2 M, or at most 0.1 M. Those of skill in the art will recognize that the ionic strength of the buffer may have any value within this range, for example, about 0.15 M.

In some embodiments, buffer additives that associate with the interfacial region and produce different orientational distributions of the proteins as a function of their concentration can also be used, such as PEG400, ethylene glycol, etc.

In some embodiments, the number of different sets of experimental conditions used for SHG polarization measurements may be increased in order to increase the number of independent molecular orientational distributions to be sampled and the number of independent polarization measurements that may be made, thereby increasing the accuracy of the angular measurements and the protein structural models derived therefrom. In some embodiments, the number of different sets of experimental conditions used may be at least 2, at least 3, at least 4, at least 5, at least 6, at least 7, at least 8, at least 9, at least 10, at least 15, at least 20, at least 30, at least 40, at least 50, at least 60, at least 70, at least 80, at least 90, or at least 100.

Measurement of $\chi^{(2)}$ and the Relationship to Protein Structure:

Each set of experimental conditions that leads to a different set of measured values for $\chi^{(2)}$ due to a different underlying orientational distribution allows for independent measurements of angle $\theta$ to be determined by SHG. By combining two or more such measurements, a more accurate determination of protein structure(s) can be made, including structure(s) of protein that exist in an equilibrium of multiple conformational states. Measurements of the components of $\chi^{(2)}$ and determination of the values for $\theta$ can be used to develop structural models through the use of standard molecular modeling techniques known to those of skill in the art and, in some embodiments, a choice of appropriate simplifying assumptions. One non-limiting example of an assumption that may be made to simplify the analysis and develop protein structural models is that, although the orientation of the two or more labels at different sites on the protein surface varies from one experimental condition to another in the laboratory frame of reference (i.e., relative to the axis normal to the surface plane), the relative orientation between them, i.e. the angle within the protein frame of reference remains constant under different experimental conditions. In effect, under this assumption one varies the orientational distribution of the proteins on the surface in ways that do not perturb their function and conformational landscape. Each experimental condition produces at least one independent equation relating the measured SHG intensity at the different polarizations to the molecular orientational distribution. Appropriate controls such as ligand-induced conformational changes, ligand competition experiments, kinetics of ligand binding, dose-response measurements, and others, can be run at each experimental condition to ensure that the protein is still functional and thus native-like. The measurements of mean angle, for example, along with other parameters of the orientational distribution of the label or hyperpolarizable moiety in the protein, can be used as constraints in de novo or integrative structural model building according to methods known to those skilled in the art. In some embodiments, for example, an apo X-ray crystallographic structure of a protein may be included in the model, and overlaid with structural data provided by SHG measurements to improve the accuracy of the model.

Non-limiting examples of assumptions that may be made in some embodiments of the disclosed method for the purpose of simplifying the analysis of the SHG structural data include: (i) that a single component of $\alpha^{(2)}$ (e.g., $\alpha_{zzz}^{(2)}$) dominates the hyperpolarizability of the label; (ii) that the hyperpolarizability of the label does not change with changes in experimental conditions; (iii) that the position of the two or more labels within the protein (i.e. the identities of the amino acid residues to which they are attached) is known; (iv) that the orientation of the tethered or immobilized protein molecules is isotropic in the X-Y plane (i.e. they are randomly oriented on the plane of the substrate surface or in the plane of a supported lipid bilayer); (v) that the change in orientation of the two or more labels is not due to intrinsic changes in protein conformation or protein un-folding; (vi) that the orientational distribution of the label at each label site constitutes a delta function (i.e. that there is no spread in orientation angle at the label site), or any such combination thereof. In some embodiments, the SHG structural data may be overlaid or combined with structural data from protein crystallographic studies, NMR studies, UV-Vis and fluorescence spectroscopic studies, circular dichroism studies, cross-linking experiments, small-angle X-ray scattering studies, etc.

In some embodiments, the attachment of nonlinear-active labels to protein molecules may be performed using standard covalent conjugation chemistries, e.g. using non-linear active moieties that are reactive with amine groups, carboxyl groups, thiol groups, and the like. In some embodiments, it may optionally be desirable to perform mass spectrometric analysis of the labeled proteins to rigorously identify the positions of the labeled amino acid residues within the protein.

In preferred embodiments, the attachment sites for the labels are determined through genetic engineering and site-directed mutagenesis techniques, as are well known to those of skill in the art (see, for example, Edelheit, et al. (2009), "Simple and Efficient Site-Directed Mutagenesis Using Two Single-Primer Reactions in Parallel to Generate Mutants for Protein Structure-Function Studies", BMC Biotechnology 9:61). Using this approach, amino acid residues comprising amine or thiol groups, for example, may be placed at precise positions within the protein prior to labeling with a nonlinear-active tag. Mutated proteins may then be tested for native-like functionality using any of a variety of assays known to those of skill in the art, e.g, performing binding assays using a known ligand for the protein.

In additionally preferred embodiments, genetic engineering techniques may be used to incorporate nonlinear-active unnatural amino acids at specific sites within the protein using any of a variety of techniques known to those of skill in the art. See, for example, Cohen, et al. (2002), "Probing Protein Electrostatics with a Synthetic Fuorescence Amino Acid", Science 296:1700-1703, and U.S. Pat. No. 9,182,406.

In one example of the disclosed methods, a protein is labeled at a single site-specifically engineered cysteine residue with an SHG-active label possessing a hyperpolarizability, which in turn possesses a single dominant element of the response $\alpha^{(2)} = \alpha^{(2)}_{z'z'z'}$. The labeled protein is attached via a His tag to a supported lipid bilayer membrane which comprises Ni-NTA moieties attached to lipid headgroups. A baseline SHG signal is generated in this way, and the non-vanishing components of $\chi^{(2)}$ (Salafsky, J. S. (2001), "'SHG-labels' for Detection of Molecules by Second Harmonic Generation", Chemical Physics Letters 342, 485-491; Salafsky, J. S. (2003), "Second-Harmonic Generation as a Probe of Conformational Change in Molecules", Chemical Physics Letters 381, 705-709; Salafsky, J. S. (2006), "Detection of Protein Conformational Change by Optical Second-Harmonic Generation", Journal of Chemical Physics 125) are given, as is well known to those of skill in the art:

$$\chi^{(2)}_{ZZZ} = N_S \langle \cos^3\theta \rangle \alpha^{(2)}_{Z'Z'Z'} \quad (1)$$

$$\chi^{(2)}_{ZXX} = \chi^{(2)}_{XZX} = \frac{1}{2} N_S \langle \sin^2\theta \cos\theta \rangle \alpha^{(2)}_{Z'Z'Z'}$$

where Ns and $\alpha_{Z'Z'Z'}^{(2)}$ are the surface density and molecular hyperpolarizability, respectively. The components of $\chi^{(2)}$ can then be determined from two different polarization-dependent measurements ($I_{zzz}$ and $I_{zxx}$, or equivalently $I_{ppp}$ and $I_{pss}$. In this case, $\chi_{zzz}^{(2)}$ can be determined by measuring the p-polarized SHG signal using p-polarized fundamental excitation light. For example, if fundamental excitation light at 800 nm is used (e.g., from a Ti: Sapphire mode-locked laser), the second harmonic signal is detected at 400 nm. In general, $I_{ppp}$, which is the SHG signal intensity observed under p-polarized excitation and p-polarized SHG detection, is governed by several components of the nonlinear susceptibily. However, a simplified approach for isolating only $\chi_{zzz}^{(2)}$ in this measurement is achieved by measuring the SHG signal at the critical angle of incidence in a total reflection geometry using a silica prism. In total internal reflection (TIR) geometry the measured SHG intensity is determined by the refractive indices of the prism and the buffer in which the surface-tethered proteins are bathed, since the off-axis tensor components of $\chi^{(2)}$ vanish, leaving only $\chi_{zzz}^{(2)}$ which determines the measured $I_{ppp}$ SHG signal intensity (referring to polarization of the fundamental/SHG beams). Similarly, $\chi_{zxx}^{(2)}$ can be determined by measuring $I_{pss}$ using s-polarized fundamental light and measuring the p-polarized SHG light intensity. In cases where $N_s$ and $\alpha_{z'z'z'}$ are unknown, ratios of the intensities measured under different polarization combinations can be used to eliminate these parameters, leaving only ratios of the orientational distributions themselves which are trigonometric functions of $\theta$, where $\theta$ is defined as the mean angle between the z-axis in the molecular frame and the surface normal. When the orientational distribution is narrow, $\theta$ can be determined directly. By repeating the measurements of the SHG intensity under different polarizations (e.g., $I_{zzz}$ and $I_{zxx}$) using protein labeled at two or more different sites (e.g., in two or more different single-site cysteine mutants, at these cysteine sites), one can obtain, for example, a different $\theta$ for each label site that can be used as a constraint in structure determination. Each measurement requires a labeled protein, preferably with the label site-specifically attached (e.g., covalently attached via site-directed cysteine mutagenesis) at a known position within the protein. By also varying the experimental conditions to produce differently oriented protein relative to the surface plane along with the two or more different sites of labeling, independent measurements can be made to determine multiple parameters describing the orientational distribution, thereby providing important constraints for protein structure determination. A key step of the present invention is to make measurements of a protein labeled at two or more different sites (preferably in separate protein-label conjugates) under two or more different experimental conditions that result in different values of $\chi^{(2)}$ or ratios of $\chi^{(2)}$ components e.g., $\chi_{zzz}^{(2)}/\chi_{zxx}^{(2)}$). By measuring values of $\chi^{(2)}$ for the same protein labeled at two or more different sites under two or more different experimental conditions, one can obtain more accurate measurements of the $\theta$'s (in the lab frame) and relate the difference between them, i.e. in the protein frame, to the structure of the protein.

For example, with two proteins each labeled at one site (site 1 and site 2), each of which is oriented differently under different experimental conditions on a surface, one can have four distinct measurements for which two polarization-dependent SHG intensities can be made as shown below, for a total of 8 independent intensity measurements:

Orientation 1: Protein labeled at site 1—measure $I_{zzz}$, $I_{zxx}$
Protein labeled at site 2—measure $I_{zzz}$, $I_{zxx}$
Orientation 2: Protein labeled at site 1—measure $I_{zzz}$, $I_{zxx}$
Protein labeled at site 2—measure $I_{zzz}$, $I_{zxx}$ By rationing the measured intensities of $I_{zzz}$ and $I_{zxx}$ and using the appropriate Fresnel factors, the hyperpolarizability and number density of the SHG-active labels can be eliminated using methods well known to those of skill in the art. Because proteins are macromolecules with many potential label attachment sites, labeling different sites and orienting the protein in different ways offers a convenient way to obtain more than one independent ratio of polarization-dependent intensities (e.g., $I_{zzz}$ and $I_{zxx}$), thereby allowing one to fit the orientational distribution term within the brackets of the Equations in (1) to multiple model parameters.

For example, if using three or more different sets of experimental conditions which produce a different protein orientational distribution for two separate protein conjugates labeled at two different cysteine sites, one obtains (2×3)−1=5 intensity ratios which can be used to determine parameters of the molecular orientational distribution. The different 0's in the lab frame can be used to calculate the intramolecular angle differences between the two label sites in the protein frame, i.e. to obtain structural information in the protein frame. This is because although the protein will be oriented differently in the lab frame when it is tethered to a surface via a His-tag at the C-terminus vs. the N-terminus (resulting in different θ's and orientational distributions), the relationship between the labels in the protein frame of reference should remain constant. Therefore, when the protein is tethered in different orientational distributions to the surface, the additional independent measurements allow one to determine the inter-angle measurements in the protein frame reference more accurately. In effect, each set of experimental condition will reorient the protein on the surface so that multiple independent measurements of the lab frame angle of the label hyperpolarizability projected on the z-axis can be obtained. Each independent measurement can be used to provide an additional constraint in determining the structure in the protein frame of reference. In effect, the mean angle differences between the two cysteine sites should remain constant across the experimental conditions, allowing for fitting of the orientational distribution to additional model parameters beyond the mean angle, such as the width of the orientational distribution (e.g., the full width at half maximum (FWHM) of a Gaussian distribution centered around the mean angle). Using this approach, structures of ligand-bound protein could be determined rapidly by making two or more independent measurements of the values of $\chi^{(2)}$ for different label sites and using these angular constraints determined by SHG along with the unbound (apo) X-ray crystal structure coordinates to determine the best ligand-bound structure at atomic resolution, without requiring X-ray crystal structure determination of the ligand-bound complex. Such ligands could be small molecules, small molecule fragments, peptides, proteins, antibodies, oligonucleotides, and in general any ligand Known to Those Skilled in the Art.

Multiple Conformations—Equilibrium Orientational Distributions:

If a protein exists in an equilibrium of multiple conformational states, the protein will be described by a multi-modal (or multi-state) orientational distribution at each label site. If the distribution is composed of a sum of Gaussians with different weights, mean angles (θs) and distribution widths (Δs), a complete description of the protein's conformational landscape will depend on determining each of these parameters. For example, if the local structure of the protein at label site 1 adopts 3 conformations, under these assumptions, the local orientational distribution can be described by 3×3 parameters to be determined, or 9 unknowns, describing amplitude, mean angle, and width for each conformation. Label site 2 may adopt only 2 local conformations and in that case can similarly be described by 6 parameters. For an experimental geometry involving a single dominant tensor component of the hyperpolarizability, isotropic symmetry in the surface plane (azimuthal symmetry), and excitation at the critical angle, two independent components of $\chi^{(2)}$ can be determined for each experimental condition (e.g., $\chi_{zzz}^{(2)}$ and $\chi_{zxx}^{(2)}$ or $\chi_{xzx}^{(2)}$); and N-1 independent ratios of these values may be used to eliminate $N_s$ and $\alpha_{z'z'z'}$). Therefore, for an experiment involving two labeled mutants under the aforementioned assumptions, a minimum of 16 independent measurements (of the components of $\chi^{(2)}$) should be made (yielding 15 independent ratios of $\chi^{(2)}$ values) which can be used to fit the orientational distributions. This approach assumes that the single dominant tensor component of the hyperpolarizability does not vary in magnitude or phase with label site. The additional independent measurements, an aspect of the present invention, can be obtained by varying the tag site (e.g., C- and N-terminus), tag length (e.g., 6×, 8×, 10× and 12× His tags), buffer conditions (e.g., different salt concentrations), and so on, or in general, any experimental conditions that varies the orientation of the protein on the surface and thus impacts the measured values of $\chi^{(2)}$. All of these independent measurements can then be used, for example, in a global fitting method to determine the solution-based conformational landscape (i.e. multi-state orientational distribution) in the protein frame of reference at these two sites. In some embodiments, the X-ray crystal structure coordinates of the protein may optionally be used as a further constraint in the model building.

Absolute Polar Orientation Determination:

Although the tilt angle orientation of the label in the lab frame can be determined, this tilt angle is degenerate in two cones pointing toward and away from the surface, respectively. The present invention also discloses a novel method for obtaining the absolute direction of the labels, i.e. which direction the label points relative to the surface plane using a simple experiment. In this experiment, the SHG signal under a given polarization condition is measured using: i) labeled protein attached to an unlabeled surface; ii) unlabeled protein attached to a labeled surface and iii) labeled protein attached to a labeled surface. The labeled surface can be prepared in a variety of ways known to those skilled in the art, for example through covalent carbodiimide coupling of a carboxylated nonlinear-active label to an aminosilane-functionalized glass substrate surface. Alternatively, with supported lipid bilayers (SLBs), one can covalently couple the same nonlinear-active label that attaches via amines or thiols (e.g. corresponding to lysine or cysteine residue side-chains) to a protein to the bilayer doped with varying mole percentages of an amine or thiol-containing lipid. This surface then provides an SHG signal of its own which, because the label is the same as that of the protein label, is in phase with the SHG signal generated from the protein. The label attached to the supported bilayer has a known polar orientation by virtue of its known directional coupling to the surface and its chemical structure. An experiment to determine the absolute polar orientation of a label on a protein (and therefore potentially the polar orientation of the entire protein) can be carried out as follows. First, the SHG signal of the labeled surface in the absence of protein is measured ($I_L$). Second, the SHG signal of the labeled protein attached to the unlabeled surface is measured ($I_P$). Third, the SHG signal of the surface is measured when labeled protein is attached to the labeled surface ($I_{TOT}$). The relationship between the different SHG signal is as follows:

$$I_{TOT}=I_L+I_P+\text{sqrt}(I_L\times I_P)\times\cos(\theta)$$

where cos(θ) describes the phase relationship (which flips in sign with the absolute polar orientation toward or away from the surface) between the labels attached to the protein molecules and the surface in the third measurement ($I_{TOT}$). By measuring $I_{TOT}$, $I_L$, and $I_P$ separately and comparing the measured signal intensities, the absolute polar orientation of each label on the protein can be determined. In some cases, e.g., when $I_L+I_P$ are of roughly comparable magnitude, if $I_{TOT}$ is smaller than $I_L$ on its own, one can immediately determine that destructive interference is occurring between the protein label and the surface label; therefore, the labels are oriented in opposite polar orientations; if $I_{TOT}$ is larger than $I_L$ on its own, constructive interference is occurring and the labels are oriented in the same polar direction. The magnitude of $I_L+I_P$ can be varied by tuning, for example, the density of attachment sites on the supported bilayer for the dye, or the density of proteins attached to the surface.

In some embodiments, the density of attachment sites on the supported lipid bilayer may be varied by varying the percentage of a lipid component of the bilayer that comprises an amine group or a thiol group (or any other functional group for which standard conjugation chemistries are available). In some embodiments, the percentage of the lipid component that comprises an amine or thiol group may range from about 0 percent to about 100 percent. In some embodiments, the percentage of the lipid component that comprises an amine or thiol group may be at least 0 percent, at least 10 percent, at least 20 percent, at least 30 percent, at least 40 percent, at least 50 percent, at least 60 percent, at least 70 percent, at least 80 percent, at least 90 percent, or at least 100 percent. In some embodiments, the percentage of the lipid component that comprises an amine or thiol group may be at most 100 percent, at most 90 percent, at most 80 percent, at most 70 percent, at most 60 percent, at most 50 percent, at most 40 percent, at most 30 percent, at most 20 percent, or at most 10 percent. Those of skill in the art will recognize that the percentage of the lipid component that comprises an amine group or a thiol group may have any value within this range, for example, about 12 percent.

In some embodiments, the density of nonlinear-active labeled proteins attached to the surface may be varied by varying the concentration of labeled protein in the solution that is incubated with the supported lipid bilayer. For example, the concentration of a His tagged, labeled protein may be varied in the solution that is incubated with a supported lipid bilayer comprising a lipid component that further comprises a Ni-NTA moiety. In some embodiment, the concentration of labeled protein in the solution may range from about 1 nM to about 100 µM. In preferred embodiments, the concentration of labeled protein in the solution may range from about 100 nM to about 5 µM. In some embodiments, the concentration of labeled protein in the solution may be at least 1 nM, at least 10 nM, at least 100 nM, at least 1 µM, at least 10 µM, or at least 100 µM. In some embodiments, the concentration of labeled protein in the solution may be at most 100 µM, at most 10 µM, at most 1 µM, at most 100 nM, at most 10 nM, or at most 1 nM. Those of skill in the art will recognize that the concentration of labeled protein in the solution may have any value with this range, for example, about 12 µM.

In some embodiments the density of nonlinear-active labeled protein on the surface may be varied using any of a variety of techniques known to those of skill in the art over the range of about $10^2$ molecules/cm$^2$ to about $10^{14}$ molecules/cm$^2$. In some embodiments, the density of nonlinear-active labeled protein on the surface may be at least $10^2$ molecules/cm$^2$, at least $10^3$ molecules/cm$^2$, at least $10^4$ molecules/cm$^2$, at least $10^5$ molecules/cm$^2$, at least $10^6$ molecules/cm$^2$, at least $10^7$ molecules/cm$^2$, at least $10^8$ molecules/cm$^2$, at least $10^9$ molecules/cm$^2$, at least $10^{10}$ molecules/cm$^2$, at least $10^{11}$ molecules/cm$^2$, at least $10^{12}$ molecules/cm$^2$, at least $10^{13}$ molecules/cm$^2$, or at least $10^{14}$ molecules/cm$^2$. In some embodiments, the density of nonlinear-active labeled protein on the surface may be at most $10^{14}$ molecules/cm$^2$, at most $10^{13}$ molecules/cm$^2$, at most $10^{12}$ molecules/cm$^2$, at most $10^{11}$ molecules/cm$^2$, at most $10^{10}$ molecules/cm$^2$, at most $10^9$ molecules/cm$^2$, at most $10^8$ molecules/cm$^2$, at most $10^7$ molecules/cm$^2$, at most $10^6$ molecules/cm$^2$, at most $10^5$ molecules/cm$^2$, at most $10^4$ molecules/cm$^2$, at most $10^3$ molecules/cm$^2$, or at most $10^2$ molecules/cm$^2$. Those of skill in the art will recognize that the density of nonlinear-active labeled protein on the surface may have any value within this range, for example, about $4.0 \times 10^{12}$ molecules/cm$^2$.

Background Signal Subtraction:

If background SHG signal is present due to the substrate-buffer interface, for example, this can be "subtracted" out in various ways. For example, the phase difference between the SHG signal from the label on the protein and the SHG signal due to the background can be measured in an interferometric experiment such as the one described in Reider, G., et al. (1999), "Coherence Artifacts in Second Harmonic Microscopy", Applied Physics B-Lasers and Optics 68, 343-347. The SHG signal due to the protein alone can then be determined.

Electric Field Orientation, Strength and Characteristics:

An electric field can be applied to manipulate the orientation of the biomolecules in the lab frame at the interface. The electric field direction can be across the surface, perpendicular to it, or in general, at any angle relative to the surface plane. In one embodiment, one electrode is placed underneath a lipid bilayer membrane or other surface chemistry for protein attachment to the substrate, e.g. a glass substrate. A counter-electrode is placed above the substrate surface plane, for example at the top of the liquid in a sample well. In another embodiment, two or more electrodes are placed in the substrate surface plane and the electric field direction is parallel to the substrate-membrane interface.

Figure 9:
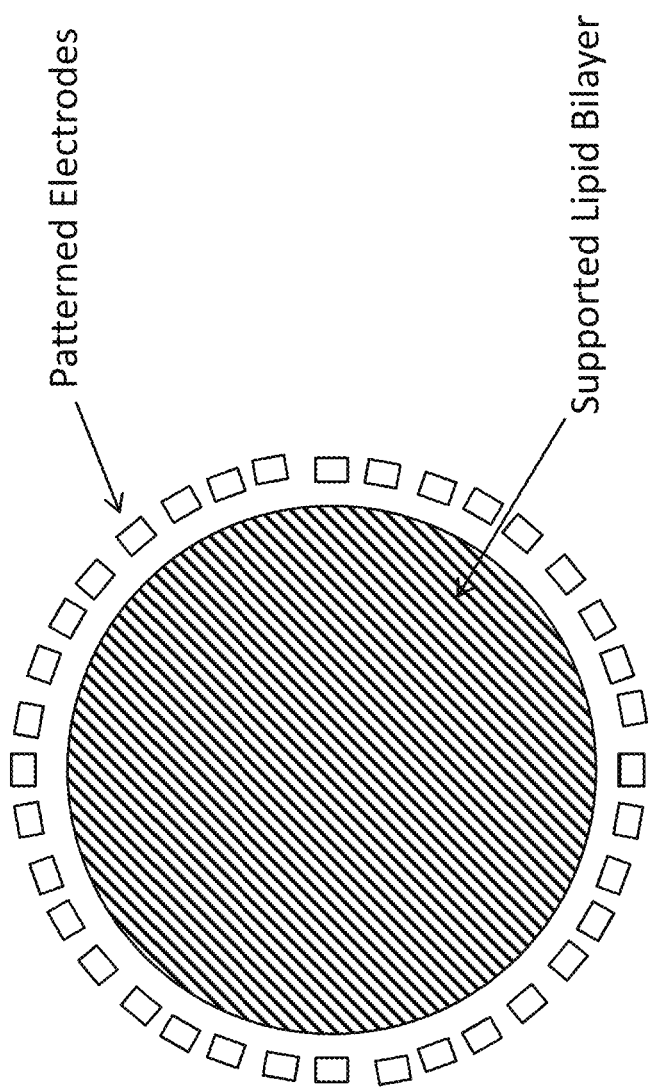
FIG. 9 provides a schematic illustration of one non-limiting example of a device comprising a patterned array of electrodes surrounding an area of a substrate surface used to form a supported lipid bilayer.
Figure 10A:
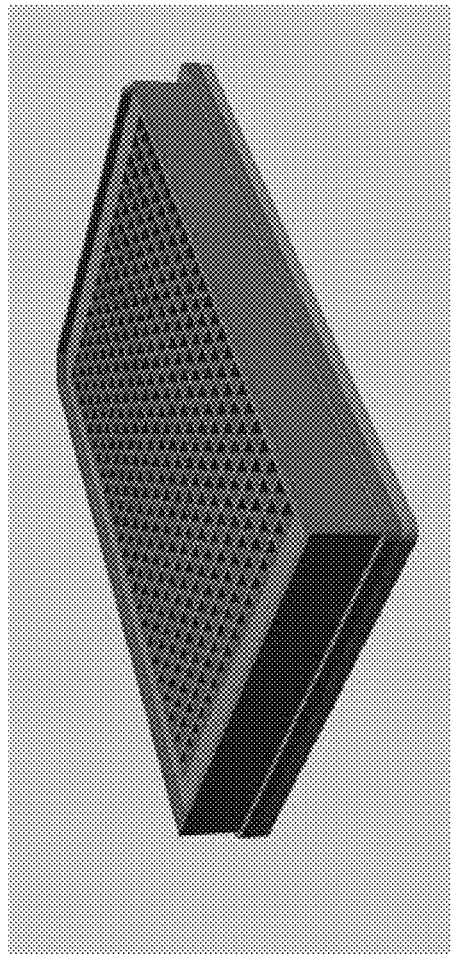
FIGS. 10A-B illustrate a microwell plate with integrated prism array for providing good optical coupling of the excitation light to the top surface of the substrate. Such a device may be useful in conducting high-throughput structure determination of proteins and other biological molecules.
Figure 10B:
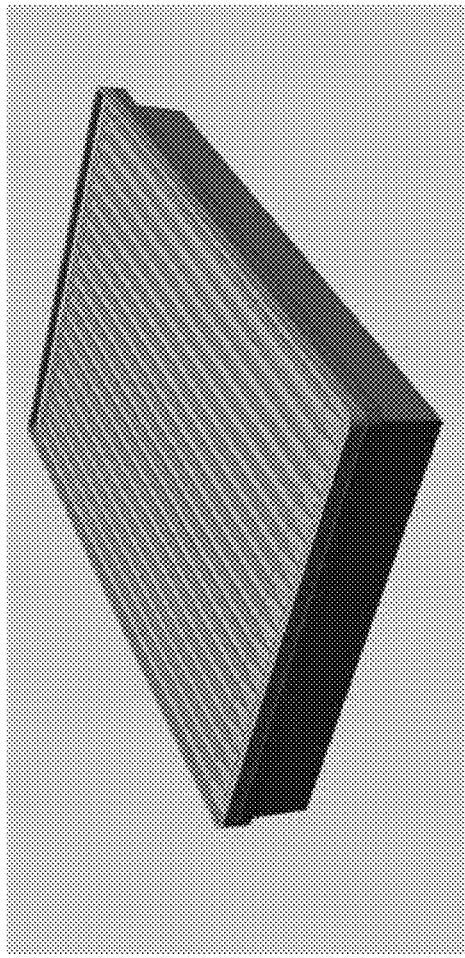
Figure 11A:
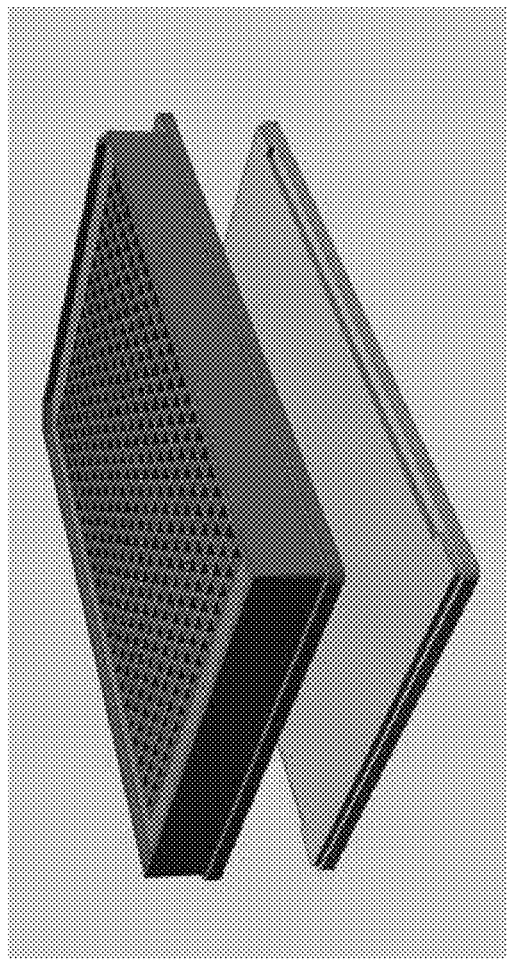
FIGS. 11A-B show exploded views of the microwell plate device shown in FIGS. 10A-B.
Figure 11B:
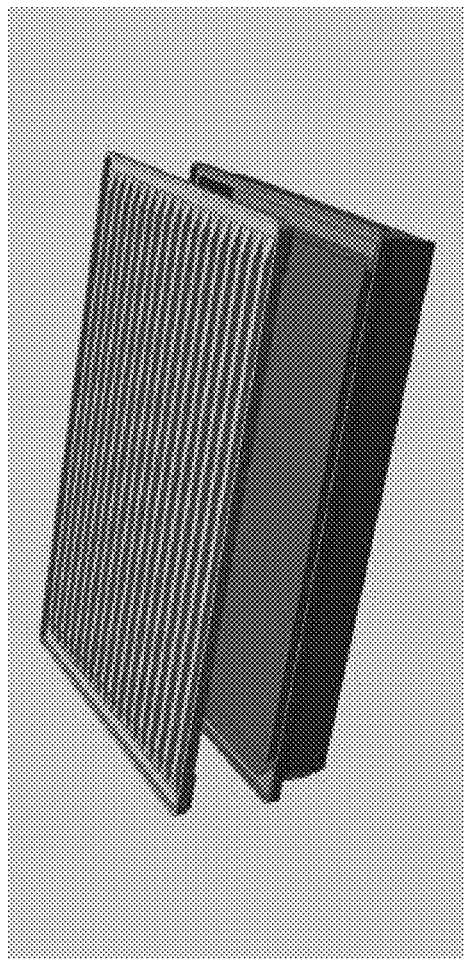

In another embodiment, an array of electrodes can be placed around the tethered or immobilized protein sample, as illustrated in FIG. 9. For example, a circular array of electrodes can be placed parallel to the membrane interface on a glass substrate surface, each spaced about 10 degrees apart from each other. Voltage applied to a pair of electrodes that are 180 degrees apart from each other allows the azimuthal direction of the electric field to be changed at will and in a rapid fashion. For example, the azimuthal direction of the electric field can be swept around the entire circle in a second or a fraction of a second.

Electrodes may be patterned on the substrate surface using any of a variety of techniques known to those of skill in the art. Examples include, but are not limited to, screen printing, photolithographic patterning, sputter coating, chemical vapor deposition, or any combination thereof.

Electrodes may be fabricated from any of a variety of material, as is well known to those of skill in the art. Examples of suitable electrode materials include, but are not limited to, silver, gold, platinum, copper, aluminum, graphite, indium tin oxide (ITO), semiconductor materials, conductive polymers, or any combination thereof.

In some embodiments, it may be desirable to passivate the surface of one or more electrodes, e.g., to minimize corrosion of the electrode surfaces that are in contact with aqueous buffers, and/or to prevent contamination of or interference with proteins or other biological components, and/or to prevent current flow in the sample. Any of a variety of passivation techniques known to those of skill in the art may be used, and will in general depend on the choice of materials used to fabricate the electrode(s). For example, indium tin oxide electrodes on glass substrates may be passivated by growth or deposition of a 30 nm SiO$_2$ layer. Metal or semiconductor electrodes will often develop an inert "native oxide" layer upon exposure to air that may serve as a passivation layer. This inert surface layer is usually an oxide or a nitride, with a thickness of a monolayer (1-3 Å) for platinum, about 15 Å for silicon, and may be close to 50 Å thick for aluminum after long exposures to air.

The electric field can be DC or AC, i.e. time-invariant or time-varying. In the latter case, it can take a sinusoidal wave of any frequency or it can be a complex wave (e.g., a step function, a saw tooth pattern, etc.) comprised of many frequency components, and the field can oscillate between positive or negative values or remain all positive or all negative. Non-periodic or pulsed electric fields can also be applied in some embodiments. The SHG signal can be read before, during or after application of an electric field to the sample.

In some embodiments, the electric field strength may range from about zero to about $10^6$ V/cm, or larger. In some embodiments, the electric field strength may be at least zero, at least 10 V/cm, at least $10^2$ V/cm, at least $10^3$ V/cm, at least $10^4$ V/cm, at least $10^5$ V/cm, or at least $10^6$ V/cm. In some embodiments, the electric field strength may be at most $10^6$ V/cm, at most $10^5$ V/cm, at most $10^4$ V/cm, at most $10^3$ V/cm, at most $10^2$ V/cm, at most 10 V/cm. Those of skill in the art will recognize that the electric field strength may have any value within this range, for example, about 500 V/cm.

In some embodiments, the frequency at which the electric field is varied may range from about 0 Hz to about $10^5$ Hz. In some embodiments, the frequency at which the electric field is varied may be at least 0 Hz, at least 10 Hz, at least $10^2$ Hz, at least $10^3$ Hz, at least $10^4$ Hz, or at least $10^5$ Hz. In some embodiments, the frequency at which the electric field is varied may be at most $10^5$ Hz, at most $10^4$ Hz, at most $10^3$ Hz, at most $10^2$ Hz, or at most 10 Hz. Those of skill in the art will recognize that the frequency at which the electric field is varied may have any value within this range, for example, about 125 Hz.

The electric field can be used to manipulate the orientation of the protein molecules and thus the baseline signal or SHG polarization dependence. In some embodiments, if orientational isotropy in the substrate surface plane (i.e. the XY plane) occurs in the absence of an applied electric field and is preserved when a field is applied, only two or three independent non-vanishing components of the nonlinear susceptibility ($\chi^{(2)}$) will exist. In other embodiments in which orientational anisotropy is present in the surface plane, either before, during or after application of an electric field, more than two or three independent, non-vanishing components of $\chi^{(2)}$ will exist, allowing for additional independent SHG measurements with different combinations of polarized fundamental and second-harmonic light. In some embodiments in which orientational anisotropy exists at the surface plane (e.g., at a lipid biomembrane to which labeled proteins are attached), multiple independent measurements of the $\chi^{(2)}$ can be made at different azimuthal angles. For example, if an electric field is applied parallel to the surface, and this causes a change in the orientational distribution of the protein molecules from isotropic in-plane to anisotropic in-plane, additional independent optical measurements can be made in many azimuthal directions relative to the direction of the applied electric field to determine the molecular orientational distribution.

Optical Multiwell Plate with Integrated Electrodes:

As will be discussed in more detail below, in some embodiments the SHG measurements described herein are preferentially performed using a microwell plate format. In some embodiments using a 384-well plate (or other microwell plate or multi-chamber formats), electrodes can be patterned on a substrate surface inside of and adjacent to the walls of the wells, as part of a lid that is used to seal the wells, elsewhere on the substrate surface (which may be glass) within the wells, or anywhere that allows both application of voltage to produce an electric field on the sample and optical reading of the SHG signal.

Figure 8:
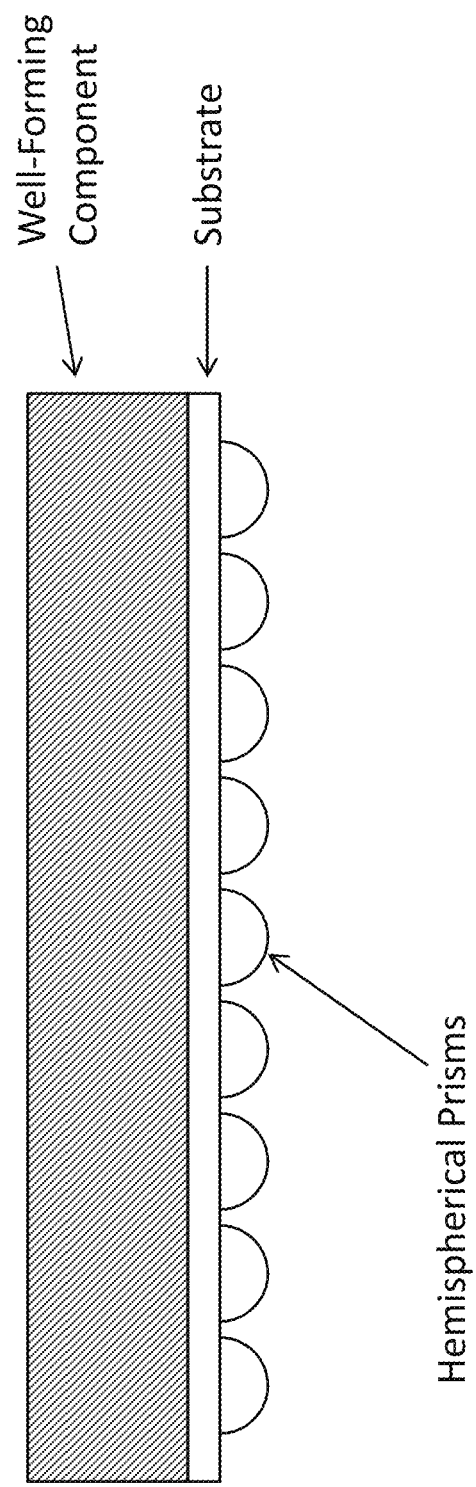
FIG. 8 provides a schematic illustration of one non-limiting example of a device for performing high-throughput structure determination using surface-selective nonlinear-optical techniques, wherein an array of hemispherical prisms bonded to or integrated with the substrate in a glass-bottom microplate format are used to provide good optical coupling of the excitation light to the top surface of the substrate.

Optical Multiwell Plate with Hemispherical Prisms:

In some embodiments, particularly in cases in which an anisotropic orientational distribution of the molecules exists at the surface, it will be useful to optically probe the sample at different azimuthal directions relative to the anisotropic axis. As an alternative to rotating the sample relative to the optical axis, the optical axis can be rotated relative to the fixed sample. To accomplish this, hemispherical prisms placed at the bottom of, or near each well, can be used to direct incoming light incident on the prisms at arbitrary angles relative to the well to the interfacial region containing the molecules. In some embodiments, the hemispherical prisms are bonded to or integrated with the substrate in a glass-bottom multi-well plate, as illustrated in FIG. 8. The hemispherical prisms make optical contact with the multi-well plate, thereby permitting transmission of the optical beam with minimal loss. In some embodiments, the optical multi-well plate will comprise a 384-well glass-bottom plate or other glass-bottom microwell plate format (i.e. standard microwell plate formats that are well known to those of skill in the art).

In some embodiments, the microwell plate device comprising an array of hemispherical prisms bonded to or integrated with the glass substrate that forms the bottom of the wells may further comprise a patterned array of electrodes on the upper surface of the glass substrate within each well so that polarized SHG measurements may be made while applying electric fields of different field strengths.

Measurement of conformational change: In one embodiment, a ligand-induced conformational change is measured at one or more label sites within the protein. In one embodiment, single-site cysteine residues are used. Combinations of polarized fundamental and nonlinear light are used to determine the components of $\chi^{(2)}$ before and after ligand addition. For example, if the biomolecules are oriented isotropically on the surface and the molecular hyperpolarizability is dominated by a single tensor element (e.g., $\alpha_{z'z'z'}$, or equivalently in some literature $\beta_{z'z'z'}$) then 4 independent measurements of $\chi^{(2)}$ can be made: two before and two after contacting the biomolecules with the ligand: (e.g., $\chi_{zzz}$ and $\chi_{xzx}$ or $\chi_{zxx}$). If one models the orientational distribution before and after conformational change as containing three adjustable parameters ($\theta_1$, $\theta_2$, and $\sigma$) where $\theta_1$ is the average lab frame orientation prior to conformational change, $\theta_2$ is the average lab frame orientation after conformational change, and $\sigma$ is the orientational width of a Gaussian around both $\theta_1$ and $\theta_2$, i.e. in one non-limiting example of a model assumption the width of the orientational angle distribution remains the same after the conformational change, then one can determine these three parameters by determining the three independent ratios of the four components of $\chi^{(2)}$ ($\chi^1_{zzz}$, $\chi^1_{zxx}$, $\chi^2_{zzz}$, $\chi^2_{zxx}$): e.g., $\chi^1_{zzz}$, $\chi^1_{zxx}$, $\chi^2_{zzz}/\chi_{zxx}$, $\chi^1_{zzz}/\chi^2_{zzz}$ where the superscripts 1 and 2 indicate the conformations before and after the ligand-induced change, respectively. The mean angles ($\theta_1$ and $\theta_2$) determined from such measurements and equation 1 can be used to determine the angular change in label orientation at the label site in the protein frame of reference due to conformational change. This process can be repeated for any number of label sites using different single-site cysteine mutants, and a model of local or the global ligand-bound structure can be determined. In some embodiments, the model optionally incorporates the X-ray crystal structure coordinates or other structural constraints (e.g., from NMR data, small angle X-ray scattering data, or any other measurements known to those skilled in the art).

High Throughput Systems and Methods

Systems and methods are disclosed herein for implementing high throughput analysis of structure of conformation in biological entities based on the use of second harmonic generation or related nonlinear optical detection techniques. As used herein, "high throughput" is a relative term used in comparison to structural measurements performed using traditional techniques such as NMR or X-ray crystallography. As will be described in more detail below, the SHG-based methods and systems disclosed herein are capable of performing structural determinations at a rate that is at least an order-of-magnitude faster than these conventional techniques.

In one aspect, this disclosure provides a method for high throughput detection of conformation or conformational change in one or more biological entities, the method comprising (i) labeling one or more target biological entities, e.g. protein molecules, with a nonlinear-active label or tag, (ii) tethering or immobilizing the one or more labeled target biological entities at one or more discrete regions of a planar substrate surface, wherein the substrate surface further comprises an optical interface, (iii) sequentially exposing each discrete region to excitation light by changing the position of the substrate relative to an external light source, (iv) collecting a nonlinear optical signal emitted from each discrete region as it is exposed to excitation light, and (v) processing said nonlinear optical signal to determine an orientation, conformation, or conformational change of each of the one or more biological entities. In another aspect, the method further comprises (vi) contacting each of the one or more biological entities with one or more test entities following the first exposure to excitation light, (vii) subsequently re-exposing each discrete region to excitation light one or more times, (viii) collecting a nonlinear optical signal from each discrete region as it is exposed to excitation light, and (ix) processing said nonlinear optical signals to determine whether or not a change in orientation or conformation has occurred in the one or more biological entities as a result of contacting with said one or more test entities. In one aspect of the method, nonlinear optical signals are detected only once following contact of the one or more biological entities with one or more test entities (i.e. endpoint assay mode), and then used to determine whether or not conformational change has occurred. In another aspect, nonlinear optical signals are collected repeatedly and at defined time intervals following contact of the one of more biological entities with one or more test entities (i.e. kinetics mode), and then used to determine the kinetics of conformational change in the one or more biological entities. In a preferred aspect of the method, each discrete region of the substrate comprises a supported lipid bilayer structure, and biological entities are immobilized in each discrete region by means of tethering to or embedding in the lipid bilayer. In another preferred aspect of the method, the excitation light is delivered to the substrate surface, i.e. the optical interface, by means of total internal reflection, and the nonlinear optical signals emitted from the discrete regions of the substrate surface are collected along the same optical axis as the reflected excitation light.

In order to implement high throughput analysis of protein structure or conformational change using nonlinear optical detection, the systems described herein require several components (illustrated schematically in FIG. 4), including (i) at least one suitable excitation light source and optics for delivering the at least one excitation light beam to an optical interface, (ii) an interchangeable substrate comprising the optical interface, to which one or more biological entities have been tethered or immobilized in discrete regions of the substrate, (iii) a high-precision translation stage for positioning the substrate relative to the at least one excitation light source, and (iv) optics for collecting nonlinear optical signals generated as a result of illuminating each of the discrete regions of the substrate with excitation light and delivering said nonlinear signals to a detector, and (v) a processor for analyzing the nonlinear optical signal data received from the detector and determining conformation or conformational change for the one or more biological entities immobilized on the substrate. In some aspects, the systems and methods disclosed herein further comprise the use of (vi) a programmable fluid-dispensing system for delivering test entities to each of the discrete regions of the substrate, and (vii) the use of plate-handling robotics for automated positioning and replacement of substrates at the interface with the optical system.

The methods and systems disclosed herein may be configured for analysis of a single biological entity contacted with a plurality of test entities, or for analysis of a plurality of biological entities contacted with a single test entity, or any combination thereof. When contacting one or more biological entities with a plurality of test entities, the contacting step may be performed sequentially, i.e. by exposing the immobilized biological entity to a single test entity for a specified period of time, followed by an optional rinse step to remove the test entity solution and regenerate the immobilized biological entity prior to introducing to the next test entity, or the contacting step may be performed in parallel, i.e. by having a plurality of discrete regions comprising the same immobilized biological entity, and exposing the biological entity in each of the plurality of discrete regions to a different test entity. The methods and systems disclosed herein may be configured to perform analysis of conformational change in at least one biological entity, at least two biological entities, at least four biological entities, at least six biological entities, at least eight biological entities, at least ten biological entities, at least fifteen biological entities, or at least twenty biological entities. In some aspects, methods and systems disclosed herein may be configured to perform analysis of conformational change in at most twenty biological entities, at most fifteen biological entities, at most ten biological entities, at most eight biological entities, at most six biological entities, at most four biological entities, at most two biological entities, or at most one biological entity. Similarly, the methods and systems disclosed herein may be configured to perform analysis of conformational change upon exposure of the one or more biological entities to at least 1 test entity, at least 5 test entities, at least 10 test entities, at least 50 test entities, at least 100 test entities, at least 500 test entities, at least 1,000 test entities, at least 5,000 test entities, at least 10,000 test entities, or at least 100,000 test entities. In some aspects, the methods and systems disclosed herein may be configured to perform analysis of conformational change upon exposure of the one or more biological test entities to at most 100,000 test entities, at most 10,000 test entities, at most 5,000 test entities, at most 1,000 test entities, at most 500 test entities, at most 100 test entities, at most 50 test entities, at most 10 test entities, at most 5 test entities, or at most 1 test entity.

Biological Entities and Test Entities

As used herein, the phrase "biological entities" comprises but is not limited to cells, proteins, peptides, receptors, enzymes, antibodies, DNA, RNA, biological molecules, oligonucleotides, solvents, small molecules, synthetic molecules, carbohydrates, or any combination thereof. Similarly, the phrase "test entities" also comprises but is not limited to cells, proteins, peptides, receptors, enzymes, antibodies, DNA, RNA, biological molecules, oligonucleotides, solvents, small molecules, synthetic molecules, carbohydrates, or any combination thereof. In some aspects, biological entities may comprise drug targets, or portions thereof, while test entities may comprise drug candidates, or portions thereof.

Nonlinear-Active Labels and Labeling Techniques

As noted above, most biological molecules are not intrinsically nonlinear-active. Exceptions include collagen, a structural protein that is found in most structural or load-bearing tissues. SHG microscopy has been used extensively in studies of collagen-containing structures, for example, the cornea. Other biological molecules or entities must be rendered nonlinear-active by means of introducing a nonlinear-active moiety such as a tag or label. A label for use in the present invention refers to a nonlinear-active moiety, tag, molecule, or particle which can be bound, either covalently or non-covalently to a molecule, particle or phase (e.g., a lipid bilayer) in order to render the resulting system more nonlinear optical active. Labels can be employed in the case where the molecule, particle or phase (e.g., a lipid bilayer) is not nonlinear active to render the system nonlinear-active, or with a system that is already nonlinear-active to add an extra characterization parameter into the system. Exogenous labels can be pre-attached to the molecules, particles, or other biological entities, and any unbound or unreacted labels separated from the labeled entities before use in the methods described herein. In a specific aspect of the methods disclosed herein, the nonlinear-active moiety is attached to the target molecule or biological entity in vitro prior to immobilizing the target molecules or biological entities in discrete regions of the substrate surface. The labeling of biological molecules or other biological entities with nonlinear-active labels allows a direct optical means of detecting interactions between the labeled biological molecule or entity and another molecule or entity (i.e. the test entity) in cases where the interaction results in a change in orientation or conformation of the biological molecule or entity using a surface-selective nonlinear optical technique.

In alternative aspects of the methods and systems described herein, at least two distinguishable nonlinear-active labels are used. The orientation of the attached two or more distinguishable labels would then be chosen to facilitate well defined directions of the emanating coherent nonlinear light beam. The two or more distinguishable labels can be used in assays where multiple fundamental light beams at one or more frequencies, incident with one or more polarization directions relative to the optical interface are used, with the resulting emanation of at least two nonlinear light beams. In some embodiments, the number of distinguishable nonlinear-active labels used my be at least two, at least three, at least four, at least five, at least six, at least seven, at least eight, at least nine, or at least ten.

Examples of nonlinear-active tags or labels include, but are not limited to, the compounds listed in Table 1, and their derivatives.

TABLE 1

Examples of Nonlinear-Active Tags 2-aryl-5-(4-pyridyl)oxazole
2-(4-pyridyl)-cycloalkano[d]oxazoles
5-aryl-2-(4-pyridyl)oxazole
7-Hydroxycoumarin-3-carboxylic acid, succinimidyl ester TABLE 1-continued Examples of Nonlinear-Active Tags Azo dyes
Benzooxazoles
Bithiophenes
Cyanines
Dapoxyl carboxylic acid, succinimidyl ester
Diaminobenzene compounds
Diazostilbenes
Fluoresceins
Hemicyanines
Indandione-1,3-pyidinium betaine
Indodicarbocyanines
Melamines
Merocyanines
Methoxyphenyl)oxa-zol-2-yl)pyridinium bromide)
Methylene blue
Oxazole or oxadizole molecules
Oxonols
Perylenes
Phenothiazine-stilbazole
Polyenes
Polyimides
Polymethacrylates
PyMPO (pyridyloxazole)
PyMPO, succinimidyl ester
(1-(3-(succinimidyloxycarbonyl)benzyl)-4-(5-(4-PyMPO, maleimide
Stilbazims
Stilbenes
Stryryl-based dyes
Sulphonyl-substituted azobenzenes
Thiophenes
Tricyanovinyl aniline
Tricyanovinyl azo In evaluating whether a species may be nonlinear-active, the following characteristics can indicate the potential for nonlinear activity: a large difference dipole moment (difference in dipole moment between the ground and excited states of the molecule), a large Stokes shift in fluorescence, or an aromatic or conjugated bonding character. In further evaluating such a species, an experimenter can use a simple technique known to those skilled in the art to confirm the nonlinear activity, for example, through detection of SHG from an air-water interface on which the nonlinear-active species has been distributed. Once a suitable nonlinear-active species bas been selected for the experiment at hand, the species can be conjugated, if desired, to a biological molecule or entity for use in the surface-selective nonlinear optical methods and systems disclosed herein.

The following reference and references therein describe techniques available for creating a labeled biological entity from a synthetic dye and many other molecules: Greg T. Hermanson, Bioconjugate Techniques, Academic Press, New York, 1996.

In a specific aspect of the methods and systems disclosed, metal nanoparticles and assemblies thereof are modified to create biological nonlinear-active labels. The following references describe the modification of metal nanoparticles and assemblies: J. P. Novak and D. L. Feldheim, "Assembly of Phenylacetylene-Bridged Silver and Gold Nanoparticle Arrays", J. Am. Chem. Soc. 122:3979-3980 (2000); J. P. Novak, et al., "Nonlinear Optical Properties of Molecularly Bridged Gold Nanoparticle Arrays", J. Am. Chem. Soc. 122:12029-12030 (2000); Vance, F. W., Lemon, B. I., and Hupp, J. T., "Enormous Hyper-Rayleigh Scattering from Nanocrystalline Gold Particle Suspensions", J. Phys. Chem. B 102:10091-93 (1999).

In yet another aspect of the methods and systems disclosed herein, the nonlinear activity of the system can also be manipulated through the introduction of nonlinear analogues to molecular beacons, that is, molecular beacon probes that have been modified to incorporate a nonlinear-active label (or modulator thereof) instead of fluorophores and quenchers. These nonlinear optical analogues of molecular beacons are referred to herein as molecular beacon analogues (MB analogues or MBA). The MB analogues to be used in the described methods and systems can be synthesized according to procedures known to one of ordinary skill in the art.

Types of Biological Interactions Detected

In addition to determining orientation or structure of proteins and other biological molecules, the methods and systems disclosed herein provide for detection of a variety of interactions between biological entities, or between biological entities and test entities, depending on the choice of biological entities, test entities, and non-linear active labeling technique employed. In one aspect, the present disclosure provides for the qualitative detection of binding events, e.g. the binding of a ligand to a receptor, as indicated by the resulting conformational change induced in the receptor. In another aspect, the present disclosure provides for quantitative analysis of binding events, e.g. the binding of a ligand to a receptor, by performing replicate measurements using different concentrations of the ligand molecule and generating a dose-response curve using the percent change in maximal conformational change observed. Similarly, other aspects of the present disclosure may provide methods for qualitative or quantitative measurements of enzyme-inhibitor interactions, antibody-antigen interactions, the formation of complexes of biological macromolecules, or interactions of receptors with allosteric modulators.

In other specific embodiments, MB analogues can be used according to the methods disclosed herein as hybridization probes that can detect the presence of complementary nucleic acid target without having to separate probe-target hybrids from excess probes as in solution-phase hybridization assays, and without the need to label the targets oligonucleotides. MB analogue probes can also be used for the detection of RNAs within living cells, for monitoring the synthesis of specific nucleic acids in sample aliquots drawn from bioreactors, and for the construction of self-reporting oligonucleotide arrays. They can be used to perform homogeneous one-well assays for the identification of single-nucleotide variations in DNA and for the detection of pathogens or cells immobilized to surfaces for interfacial detection.

Interactions between biological entities or biological and test entities (e.g. binding reactions, conformational changes, etc.) can be correlated through the methods presently disclosed to the following measurable nonlinear signal parameters: (i) the intensity of the nonlinear light, (ii) the wavelength or spectrum of the nonlinear light, (iii) the polarization of the nonlinear light, (iv) the time-course of (i), (ii), or (iii), and/or vi) one or more combinations of (i), (ii), (iii), and (iv).

Laser Light Sources and Excitation Optical System

Figure 5:
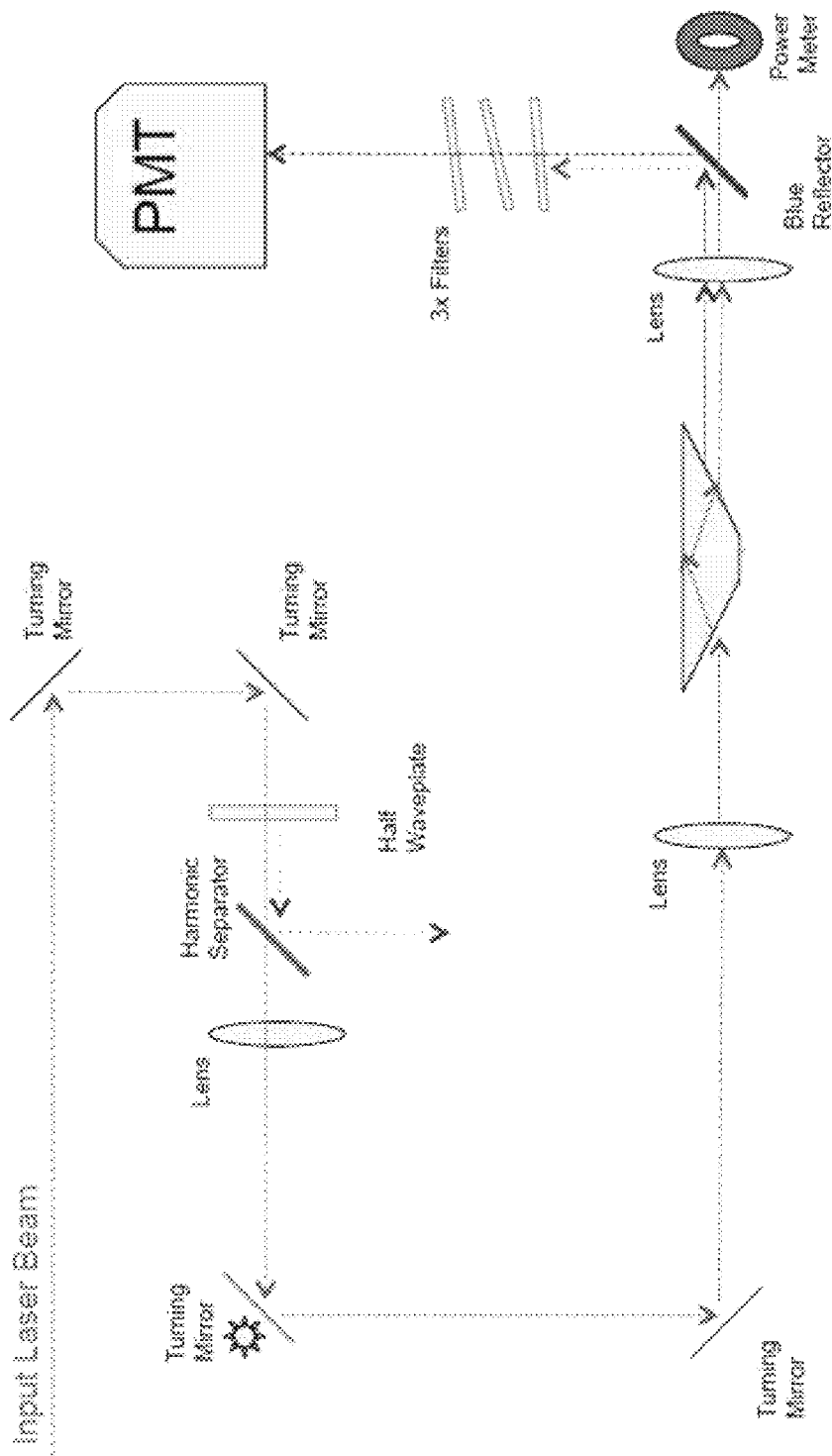
FIG. 5 shows a schematic for one non-limiting example of an optical setup used for analysis of structure or conformational change in biological molecules using nonlinear optical detection.
Figure 6:
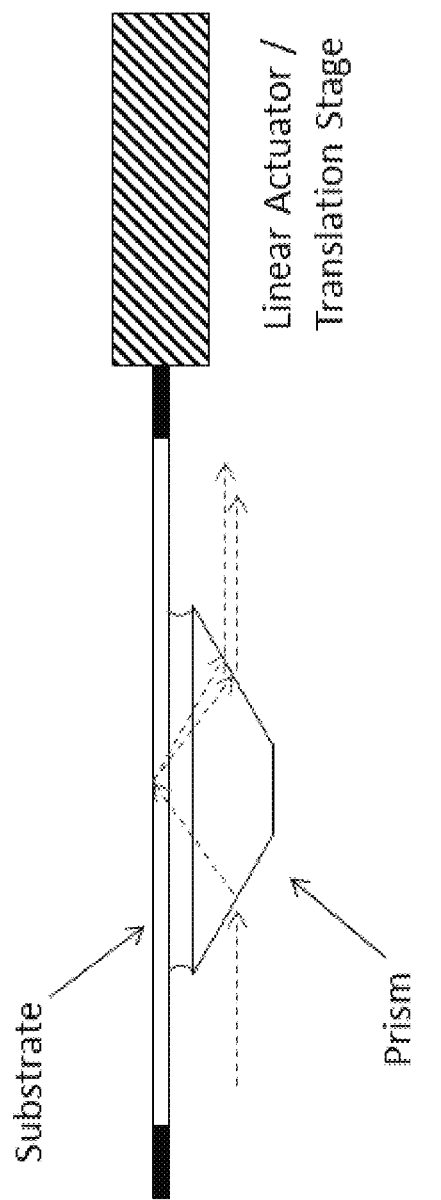
FIG. 6 shows a schematic illustration depicting the use of a prism to direct excitation light at an appropriate incident angle such that the excitation light undergoes total internal reflection at the top surface of a substrate. The two dashed lines to the right of the prism indicate the optical path of the reflected excitation light and the nonlinear optical signal generated at the substrate surface when nonlinear-active species are tethered to the surface. The substrate is optionally connected to the actuator of an X-Y translation stage for re-positioning between measurements. The curved lines between the top surface of the prism and the lower surface of the substrate indicate the presence a thin layer (not to scale) of index-matching fluid used to ensure high optical coupling efficiency between the prism and substrate.

FIG. 5 illustrates one aspect of the methods and systems disclosed herein wherein second harmonic light is generated by reflecting incident fundamental excitation light from the surface of a substrate comprising the sample interface (or optical interface). In some embodiments, the substrate is optically-coupled to a prism used to deliver laser light at the appropriate angle to induce total internal reflection at the substrate surface (FIG. 6). In some embodiments, the optical coupling is provided by use of a thin film of an index-matching fluid. A laser provides the fundamental light necessary to generate second harmonic light at the sample interface. Typically this will be a picosecond or femtosecond laser, either wavelength tunable or not tunable, and commercially available (e.g. a Ti:Sapphire femtosecond laser or fiber laser system). Light at the fundamental frequency (w) exits the laser and its polarization is selected using, for example a half-wave plate appropriate to the frequency and intensity of the light (e.g., available from Melles Griot, Oriel, or Newport Corp.). The beam then passes through a harmonic separator designed to pass the fundamental light but block nonlinear light (e.g. second harmonic light). This filter is used to prevent back-reflection of the second harmonic beam into the laser cavity which can cause disturbances in the lasing properties. A combination of mirrors and lenses are then used to steer and shape the beam prior to reflection from a final mirror that directs the beam via a prism to impinge at a specific location and with a specific angle $\theta$ on the substrate surface such that it undergoes total internal reflection at the substrate surface. One of the mirrors in the optical path can be scanned if required using a galvanometer-controlled mirror scanner, a rotating polygonal mirror scanner, a Bragg diffractor, acousto-optic deflector, or other means known in the art to allow control of a mirror's position. The substrate comprising the optical interface and nonlinear-active sample surface can be mounted on an x-y translation stage (computer controlled) to select a specific location on the substrate surface for generation of the second harmonic beam. In some aspects of the methods and systems presently described, it is desirable to scan or rotate one mirror in order to slightly vary the angle of incidence for total internal reflection, and thereby maximize the nonlinear optical signal emitted from the discrete regions of the substrate surface without substantially changing the position of the illuminating excitation light spot. In some aspects, two (or more) lasers having different fundamental frequencies may be used to generate sum frequency or difference frequency light at the optical interface on which the non-linear active sample is immobilized.

Substrate Formats, Optical Interface, and Total Internal Reflection

As described above, the systems and methods of the present disclosure utilize a planar substrate for tethering or immobilization of one or more biological entities on a top surface of the substrate, wherein the top substrate surface further comprises the optical interface (or sample interface) used for exciting nonlinear optical signals. The substrate can be glass, silica, fused-silica, plastic, or any other solid material that is transparent to the fundamental and second harmonic light beams, and that supports total internal reflection at the substrate/sample interface when the excitation light is incident at an appropriate angle. In some aspects of the invention, the discrete regions within which biological entities are contained are configured as one-dimensional or two-dimensional arrays, and are separated from one another by means of a hydrophobic coating or thin metal layer. In other aspects, the discrete regions may comprise indents in the substrate surface. In still other aspects, the discrete regions may be separated from each other by means of a well-forming component such that the substrate forms the bottom of a microwell plate (or microplate), and each individual discrete region forms the bottom of one well in the microwell plate. In one aspect of the present disclosure, the well-forming component separates the top surface of the substrate into 96 separate wells. In another aspect, the well-forming component separates the top surface of the substrate into 384 wells. In yet another aspect, the well-forming component separates the top surface of the substrate into 1,536 wells. In all of these aspects, the substrate, whether configured in a planar array, indented array, or microwell plate format, may comprise a disposable or consumable device or cartridge that interfaces with other optical and mechanical components of the high throughput system.

The methods and systems disclosed herein further comprise specifying the number of discrete regions or wells into which the substrate surface is divided, irrespective of how separation is maintained between discrete regions or wells. Having larger numbers of discrete regions or wells on a substrate may be advantageous in terms of increasing the sample analysis throughput of the method or system. In one aspect of the present disclosure, the number of discrete regions or wells per substrate is between 10 and 1,600. In other aspects, the number of discrete regions or wells is at least 10, at least 20, at least 50, at least 100, at least 200, at least 300, at least 400, at least 500, at least 750, at least 1,000, at least 1,250, at least 1,500, or at least 1,600. In yet other aspects of the disclosed methods and systems, the number of discrete regions or wells is at most 1,600, at most 1,500, at most 1,000, at most 750, at most 500, at most 400, at most 300, at most 200, at most 100, at most 50, at most 20, or at most 10. In a preferred aspect, the number of discrete regions or wells is 96. In another preferred aspect, the number of discrete regions or wells is 384. In yet another preferred aspect, the number of discrete regions or wells is 1,536. Those of skill in the art will appreciate that the number of discrete regions or wells may fall within any range bounded by any of these values (e.g. from about 12 to about 1,400).

The methods and systems disclosed herein also comprise specifying the surface area of the discrete regions or wells into which the substrate surface is divided, irrespective of how separation is maintained between discrete regions or wells. Having discrete regions or wells of larger area may facilitate ease-of-access and manipulation of the associated biological entities in some cases, whereas having discrete regions or wells of smaller area may be advantageous in terms of reducing assay reagent volume requirements and increasing the sample analysis throughput of the method or system. In one aspect of the present disclosure, the surface area of the discrete regions or wells is between 1 $mm^2$ and 100 $mm^2$. In other aspects, the area of the discrete regions or wells is at least 1 $mm^2$, at least 2.5 $mm^2$, at least 5 $mm^2$, at least 10 $mm^2$, at least 20 $mm^2$, at least 30 $mm^2$, at least 40 $mm^2$, at least 50 $mm^2$, at least 75 $mm^2$, or at least 100 $mm^2$. In yet other aspects of the disclosed methods and systems, the area of the discrete regions or wells is at most 100 $mm^2$, at most 75 $mm^2$, at most 50 $mm^2$, at most 40 $mm^2$, at most 30 $mm^2$, at most 20 $mm^2$, at most 10 $mm^2$, at most 5 $mm^2$, at most 2.5 $mm^2$, or at most 1 $mm^2$. In a preferred aspect, the area of discrete regions or wells is about 35 $mm^2$. In another preferred aspect, the area of the discrete regions or wells is about 8.6 $mm^2$. Those of skill in the art will appreciate that the area of the discrete regions or wells may fall within any range bounded by any of these values (e.g. from about 2 $mm^2$ to about 95 $mm^2$).

Discrete regions of the substrate surface are sequentially exposed to (illuminated with) excitation light by re-positioning the substrate relative to the excitation light source. Total internal reflection of the incident excitation light creates an "evanescent wave" at the sample interface, which excites the nonlinear-active label and results in generation of second harmonic light (or in some aspects, sum frequency or difference frequency light). Because the intensity of the evanescent wave, and hence the intensity of the nonlinear optical signals generated, is dependent on the incident angle of the excitation light beam, precise orientation of the substrate plane with respect to the optical axis of the excitation beam and efficient optical coupling of the beam to the substrate is critical for achieving optimal SHG signal across the array of discrete regions. In some aspects of the present disclosure, total internal reflection is achieved by means of a single reflection of the excitation light from the substrate surface. In other aspects, the substrate may be configured as a waveguide such that the excitation light undergoes multiple total internal reflections as it propagates along the waveguide. In yet other aspects, the substrate may be configured as a zero-mode waveguide, wherein an evanescent field is created by means of nanofabricated structures.

Efficient optical coupling between the excitation light beam and the substrate in an optical setup such as the one illustrated in FIGS. 5 and 6 would typically be achieved by use of an index-matching fluid such as mineral oil, mixtures of mineral oil and hydrogenated terphenyls, perfluorocarbon fluids, glycerin, glycerol, or similar fluids having a refractive index near 1.5, wherein the index-matching fluid is wicked between the prism and the lower surface of the substrate. Since a static, bubble-free film of index-matching fluid is likely to be disrupted during fast re-positioning of the substrate, the systems and methods disclosed herein include alternative approaches for creating efficient optical coupling of the excitation beam to the substrate in high throughput systems.

Figure 7:
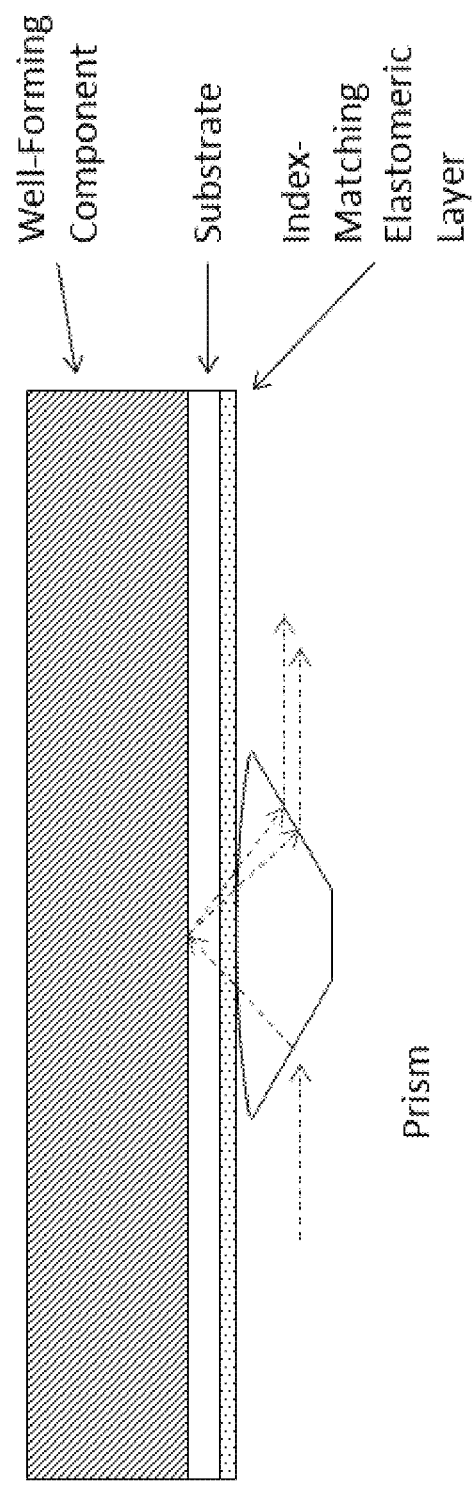
FIG. 7 shows a schematic illustration depicting the use of a layer of index-matching elastomeric material attached or adjacent to the lower surface of a transparent substrate (configured in a microwell plate format in this example) to ensure high optical coupling efficiency between a prism and the upper surface of the substrate. In some embodiments of this approach, the upper surface of the prism is slightly domed to focus the compression force when bringing the microwell plate and prism into contact, thereby reducing or eliminating the formation of air gaps between the prism and elastomeric material.

FIG. 7 illustrates another aspect of a high throughput system of the present disclosure, in which a thin layer of index-matching elastomeric material is used in place of index-matching fluid to maintain efficient optical coupling between the prism and substrate. In this case, the substrate is again packaged in a microwell plate format (e.g. a glass bottom microplate format), but with a thin layer of an index-matching elastomeric material attached to or adjacent to the lower surface of the substrate, such that when placed in contact with the upper surface of the prism, the elastomer fills the gap between prism and substrate and provides for efficient optical coupling. Examples of elastomeric materials that may be used include, but are not limited to silicones having a refractive index of about 1.4. In one aspect of the present disclosure, the refractive index of the elastomeric material is between about 1.35 and about 1.6. In other aspects, the index of refraction is about 1.6 or less, about 1.55 or less, about 1.5 or less, about 1.45 or less, about 1.4 or less, or about 1.35 or less. In yet other aspects, the index of refraction is at least about 1.35, at least about 1.4, at least about 1.45, at least about 1.5, at least about 1.55, or at least about 1.6. Those of skill in the art will appreciate that the index of refraction of the elastomeric layer may fall within any range bounded by any of these values (e.g. from about 1.4 to about 1.6). In one aspect of this approach, the thickness of the layer of elastomeric material is between about 0.1 mm and 2 mm. In other aspects, the thickness of the elastomeric layer is at least 0.1 mm, at least 0.2 mm, at least 0.4 mm, at least 0.6 mm, at least 0.8 mm, at least 1.0 mm, at least 1.2 mm, at least 1.4 mm, at least 1.6 mm, at least 1.8 mm, or at least 2.0 mm. In another aspect of this approach, the thickness of the elastomeric layer is at most 2.0 mm, at most 1.8 mm, at most 1.6 mm, at most 1.4 mm, at most 1.2 mm, at most 1.0 mm, at most 0.8 mm, at most 0.6 mm, at most 0.4 mm, at most 0.2 mm, or at most 0.1 mm. Those of skill in the art will appreciate that the thickness of the elastomeric layer my fall within any range bounded by any of these values (e.g. from about 0.1 mm to about 1.5 mm). In another aspect of this approach, the upper surface of the prism has a partially-cylindrical ridge or is domed (FIG. 7) to focus the compression force and provide better contact between substrate, elastomeric layer, and prism surface. This approach may also require the use of a third axis of translation for positioning of the substrate, i.e. between excitation and detection steps, the substrate (microwell plate) would be raised slightly to eliminate contact between the elastomeric layer and the prism prior to re-positioning the substrate to the location of the next discrete region to be analyzed.

Figure 12:
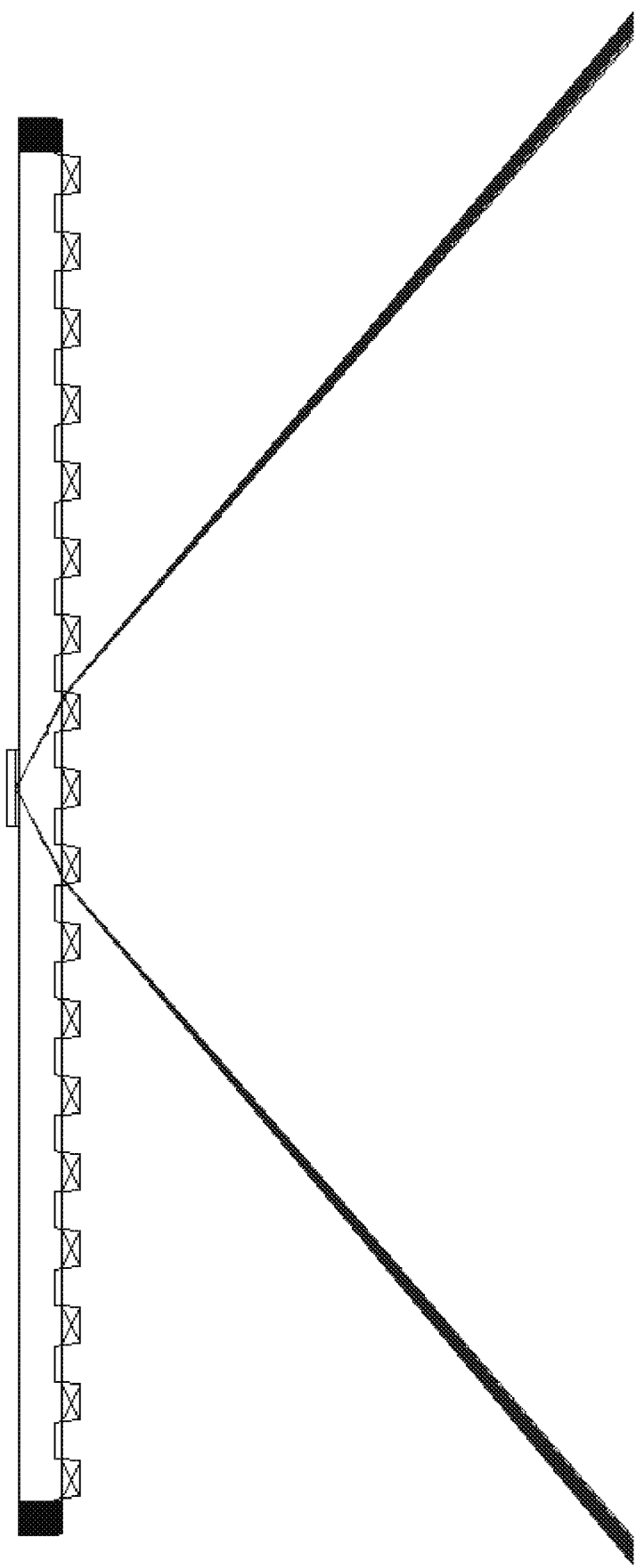
FIG. 12 illustrates the incident and exit light paths for coupling the excitation light to the substrate surface via total internal reflection using the design concept illustrated in FIGS. 10A-B.

FIGS. 10A-B and FIGS. 11A-B illustrate a preferred aspect of a high throughput system of the present disclosure, in which an array of prisms or gratings is integrated with the lower surface of the substrate (packaged in a microwell plate format) and used to replace the fixed prism, thereby eliminating the need for index-matching fluids or elastomeric layers entirely. The array of prisms (or gratings) is aligned with the array of discrete regions or wells on the upper surface of the substrate in such a way that incident excitation light is directed by an "entrance prism" ("entrance grating") to a discrete region or well that is adjacent to but not directly above the entrance prism (entrance grating), at an angle of incidence that enables total internal reflection of the excitation light beam from the sample interface (see FIG. 12), and such that the reflected excitation beam, and nonlinear-optical signals generated at the illuminated discrete region, are collected by an "exit prism" ("exit grating") that is again offset from (adjacent to but not directly underneath) the discrete region under interrogation, and wherein the entrance prism and exit prism (entrance grating and exit grating) for each discrete region are different, non-unique elements of the array.

In general, for an array of discrete regions comprising M rows×N columns of individual features, the corresponding prism or grating array will have M+2 rows×N columns or N+2 columns×M rows of individual prisms or gratings. In some embodiments, M may have a value of at least 2, at least 4, at least 6, at least 8, at least 12, at least 14, at least 16, at least 18, at least 20, at least 25, at least 30, at least 35, at least 40, at least 45, or at least 50 rows. In some embodiments, M may have a value of at most 50, at most 45, at most 40, at most 35, at most 30, at most 25, at most 20, at most 18, at most 16, at most 14, at most 12, at most 10, at most 8, at most 6, at most 4, or at most 2 rows. Similarly, in some embodiments, N may have a value of at least 2, at least 4, at least 6, at least 8, at least 12, at least 14, at least 16, at least 18, at least 20, at least 25, at least 30, at least 35, at least 40, at least 45, or at least 50 columns. In some embodiments, N may have a value of at most 50, at most 45, at most 40, at most 35, at most 30, at most 25, at most 20, at most 18, at most 16, at most 14, at most 12, at most 10, at most 8, at most 6, at most 4, or at most 2 columns. As will be apparent to those of skill in the art, M and N may have the same value or different values, and may have any value within the range specified above, for example, M=15 and N=45.

The geometry and dimensions of the individual prisms or gratings, including the thickness of the prism or grating array layer, are optimized to ensure that incident light undergoes total internal reflection at the selected discrete region of the substrate, and nonlinear optical signals generated at the selected discrete region are collected, with high optical coupling efficiency, independently of the position of substrate (microwell plate) relative to the excitation light beam. The prism or grating arrays may be fabricated by a variety of techniques known to those of skill in the art, for example, in a preferred aspect, they may be injection molded from smooth flowing, low birefringence materials such as cyclic olefin copolymer (COC) or cyclic olefin polymer (COP), acrylic, polyester, or similar polymers. In some aspects, the prism or grating array may be fabricated as a separate component, and subsequently integrated with the lower surface of the substrate. In other aspects, the prism or grating array may be fabricated as an integral feature of substrate itself.

Immobilization Chemistries

As disclosed herein, substrates in any of the formats described above are further configured for immobilization of biological entities within the specified discrete regions. Immobilization of biological molecules or cells may be accomplished by a variety of techniques known to those of skill in the art, for example, through the use of aminopropyl silane chemistries to functionalize glass or fused-silica surfaces with amine functional groups, followed by covalent coupling using amine-reactive conjugation chemistries, either directly with the biological molecule of interest, or via an intermediate spacer or linker molecule. Non-specific adsorption may also be used directly or indirectly, e.g. through the use of BSA-NHS (BSA-N-hydroxysuccinimide) by first attaching a molecular layer of BSA to the surface and then activating it with N,N'-disuccinimidyl carbonate. The activated lysine, aspartate or glutamate residues on the BSA react with surface amines on proteins.

In a preferred aspect of the present disclosure, biological molecules may be immobilized on the surface by means of tethering to or embedding in "supported lipid bilayers", the latter comprising small patches of lipid bilayer confined to a silicon or glass surface by means of hydrophobic and electrostatic interactions, where the bilayer is "floating" above the substrate surface on a thin layer of aqueous buffer. Supported phospholipid bilayers can also be prepared with or without membrane proteins or other membrane-associated components as described, for example, in Salafsky et al., "Architecture and Function of Membrane Proteins in Planar Supported Bilayers: A Study with Photosynthetic Reaction Centers", Biochemistry 35 (47): 14773-14781 (1996); Gennis, R., *Biomembranes*, Springer-Verlag, 1989; Kalb et al., "Formation of Supported Planar Bilayers by Fusion of Vesicles to Supported Phospholipid Monolayers", Biochimica Biophysica Acta. 1103:307-316 (1992); and Brian et al. "Allogeneic Stimulation of Cytotoxic T-cells by Supported Planar Membranes", PNAS-Biological Sciences 81(19): 6159-6163 (1984), relevant portions of which are incorporated herein by reference. Supported phospholipid bilayers are well known in the art and there are numerous techniques available for their fabrication. Potential advantages of using supported lipid bilayers for immobilization of proteins or other biological entities on substrate surfaces or optical interfaces include (i) preservation of membrane protein structure for those proteins that typically span the cell membrane or other membrane components of cells and require interaction with the hydrophobic core of the bilayer for stabilization of secondary and tertiary structure, (ii) preservation of two dimensional lateral and rotational diffusional mobility for studying interactions between protein components within the bilayer, and (iii) preservation of molecular orientation, depending on such factors as the type of protein under study (i.e. membrane or soluble protein), how the bilayer membrane is formed on the substrate surface, and how the protein is tethered to the bilayer (in the case of soluble proteins). Supported bilayers, with or without tethered or embedded protein, should typically be submerged in aqueous solution to prevent their destruction when exposed to air.

Soluble proteins and other biological entities may be tethered or attached to the supported lipid bilayer in an oriented fashion using a number of different anchor molecules, linkers, and/or attachment chemistries. As used herein, "anchor molecules" are molecules which are embedded in the lipid bilayer, and may comprise fatty acid, glycerolipid, glycerophospholipid, sphingolipid, or other lipid or non-lipid molecules to which attachment moieties are conjugated.

Linker molecules are molecules used to provide spatial ("vertical") separation between the attachment point of the protein or other biological entity being tethered and the attachment point on the anchor molecule embedded in the plane of the lipid bilayer. Examples of suitable linker molecules include, but are not limited to, omega-amino fatty acids, polyethylene glycols, and the like.

Attachment moieties (also referred to as "affinity tags") are specific chemical structures or binding partners that provide for covalent or non-covalent binding between two biological entities. Examples of attachment moieties or affinity tags that are suitable for use in the methods disclosed herein include biotin and avidin (or biotin and streptavidin), and His-tag/Ni-NTA binding partners.

The high affinity, non-covalent biotin-streptavidin interaction is widely used in biological assay techniques to conjugate or immobilize proteins or other biological entities. Biotinylation of proteins enables capture by multivalent avidin or streptavidin molecules that are themselves adhered to a surface (e.g. glass slides or beads) or conjugated to another molecule (e.g. through the use of a biotin-streptavidin-biotin bridge or linker). The biotin moiety is sufficiently small that biotinylation typically doesn't interfere with protein function. The high affinity (Kd of 10-14 M to 10-15M) and high specificity of the binding interaction between biotin and avidin or streptavidin enables capture of biotinylated proteins of interest even from complex samples. Due to the extremely strong binding interaction, harsh conditions are needed to elute biotinylated protein from streptavidin-coated surfaces (typically 6M guanidine HCl at pH 1.5), which will often denature the protein of interest. The use of monomeric forms of avidin or streptavidin, which have a decreased biotin-binding affinity of ~10-8 M, may allow biotinylated proteins to be eluted with excess free biotin if necessary. In the methods disclosed herein, lipid molecules comprising biotin moieties may be incorporated into supported lipid bilayers for the purpose of immobilizing or tethering biotinylated proteins and/or other biotinylated biological entities to the bilayer via a biotin-avidin-biotin (or biotin-streptavidin-biotin) bridge.

Biotinylation of proteins and other biological entities may be performed by direct coupling, e.g. through conjugation of primary amines on the surface of a protein using N-hydroxysuccinimidobiotin (NHS-biotin). Alternatively, recombinant proteins are conveniently biotinylated using the AviTag approach, wherein the AviTag peptide sequence (GLNDIFEAQKIEWHE) is incorporated into the protein through the use of genetic engineering and protein expression techniques. The presence of the AviTag sequence allows biotinylation of the protein by treatment with the BirA enzyme.

His tag chemistry is another widely used tool for purification of recombinant proteins and other biomolecules. In this approach, for example, a DNA sequence specifying a string of six to nine histidine residues may be incorporated into vectors used for production of recombinant proteins comprising 6xHis or poly-His tags fused to their N- or C-termini. His-tagged proteins can then be purified and detected as a result of the fact that the string of histidine residues binds to several types of immobilized metal ions, including nickel, cobalt and copper, under specific buffer conditions. Supports such as agarose beads or magnetic particles can be derivatized with chelating groups to immobilize the desired metal ions, which then function as ligands for binding and purification of the His-tagged biomolecules of interest.

The chelators most commonly used to create His-tag ligands are nitrilotriacetic acid (NTA) and iminodiacetic acid (IDA). Once NTA- or IDA-conjugated supports are prepared, they can be "loaded" with the desired divalent metal (e.g., Ni, Co, Cu, or Fe). When using nickel as the metal, for example, the resulting affinity support is usually called a Ni-chelate, Ni-IDA or Ni-NTA support. Affinity purification of His-tagged fusion proteins is the most common application for metal-chelate supports in protein biology research. Nickel or cobalt metals immobilized by NTA-chelation chemistry are the systems of choice for this application. In the methods disclosed herein, lipid molecules comprising Ni-NTA groups (or other chelated metal ions) may be incorporated into supported lipid bilayers for the purpose of immobilizing or tethering His-tagged proteins and other His-tagged biological entities to the bilayer. In some embodiment, the supported lipid bilayer may comprise 1,2-dioleoyl-sn-glycero-3-phosphocholine, and may also contain 1,2-dioleoyl-sn-glycero-3-[(N-(5-amino-1-carboxypentyl)iminodiacetic acid)succinyl] (nickel salt) at various concentrations.

Poly-His tags bind best to chelated metal ions in near-neutral buffer conditions (physiologic pH and ionic strength). A typical binding/wash buffer consists of Tris-buffer saline (TBS) pH 7.2, containing 10-25 mM imidazole. The low-concentration of imidazole helps to prevent non-specific binding of endogenous proteins that have histidine clusters. Elution and recovery of captured His-tagged protein from chelated metal ion supports, when desired, is typically accomplished using a high concentration of imidazole (at least 200 mM), low pH (e.g., 0.1M glycine-HCl, pH 2.5), or an excess of strong chelator (e.g., EDTA). Immunoglobulins are known to have multiple histidines in their Fc region and can bind to chelated metal ion supports, therefore stringent binding conditions (e.g. using an appropriate concentration of imidazole) are necessary to avoid high levels of background binding if immunoglobulins are present in a sample at high relative abundance compared to the His-tagged proteins of interest. Albumins, such as bovine serum albumin (BSA), also have multiple histidines and can yield high levels of background binding to chelated metal ion supports in the absence of more abundant His-tagged proteins or the use of imidazole in the binding/wash buffer.

Collection Optics and Detector

FIG. 5 further illustrates the collection optics and detector used to detect nonlinear optical signals generated upon sequential illumination of the discrete regions of the substrate. Because surface-selective nonlinear optical techniques are coherent techniques, meaning that the fundamental and nonlinear optical light beams have wave fronts that propagate through space with well-defined spatial and phase relationships, minimal collection optics are required. Emitted nonlinear optical signals are collected by means of a prism (or the integrated prism or grating array of the microplate device described above) and directed via a dichroic reflector and mirror to the detector. Additional optical components, e.g. lenses, optical bandpass filters, mirrors, etc. are optionally used to further shape, steer, and/or filter the beam prior to reaching the detector. A variety of different photodetectors may be used, including but not limited to photodiodes, avalanche photodiodes, photomultipliers, CMOS sensors, or CCD devices.

X-Y Translation Stage

Figure 4:
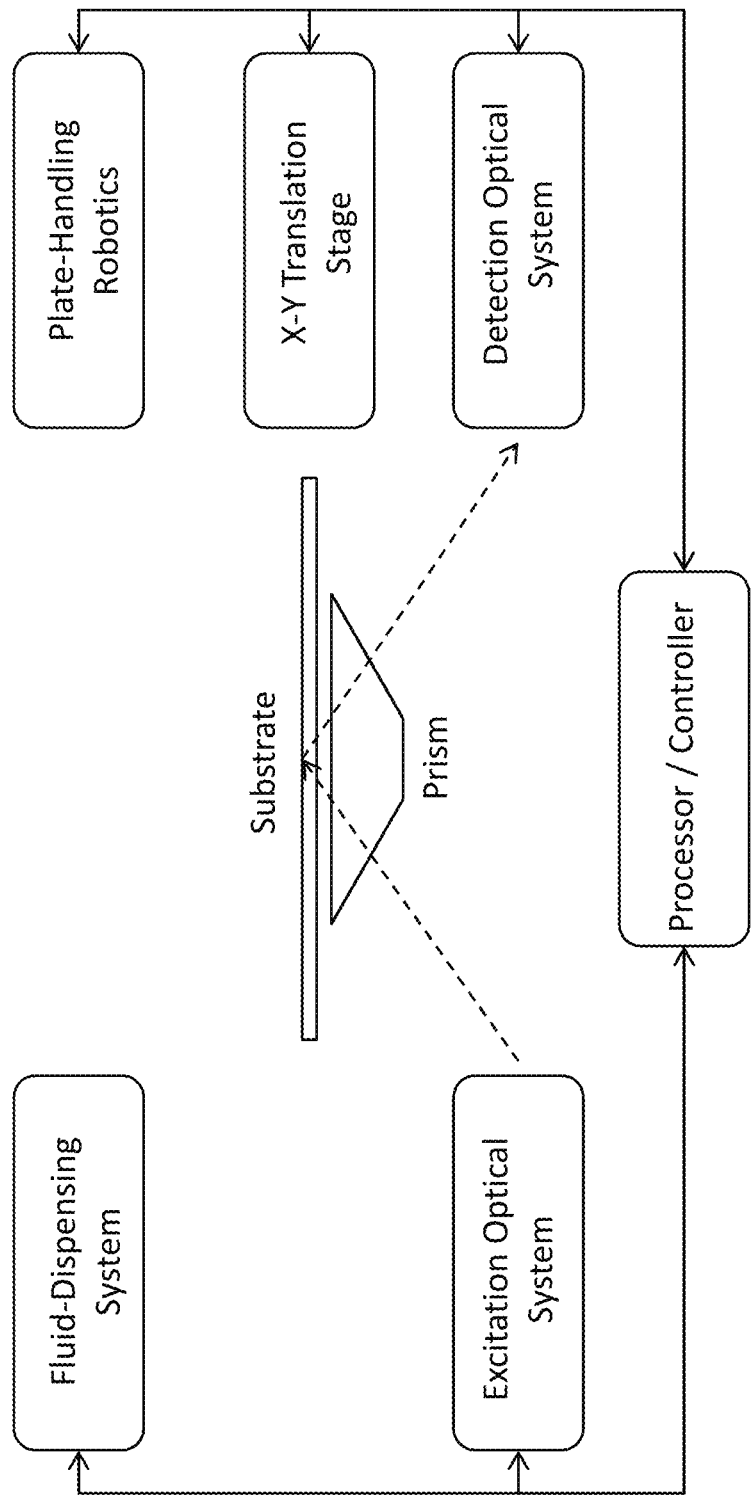
FIG. 4 illustrates one non-limiting example of the system architecture for a high throughput analysis system for determining structure or conformational change of biological molecules, e.g. proteins or other biological entities, based on nonlinear optical detection.

As illustrated in FIG. 4, implementation of the high throughput systems disclosed herein ideally utilizes a high precision X-Y (or in some cases, an X-Y-Z) translation stage for re-positioning the substrate (in any of the formats described above) in relation to the excitation light beam. Suitable translation stages are commercially available from a number of vendors, for example, Parker Hannifin. Precision translation stage systems typically comprise a combination of several components including, but not limited to, linear actuators, optical encoders, servo and/or stepper motors, and motor controllers or drive units. High precision and repeatability of stage movement is required for the systems and methods disclosed herein in order to ensure accurate measurements of nonlinear optical signals when interspersing repeated steps of optical detection and/or liquid-dispensing. Also, as the size of the focal spot for the excitation light [20-200 microns in diameter or on a side is substantially smaller than the size of the discrete regions on the substrate, in some aspects of the present disclosure, it may also be desirable to return to a slightly different position within a given discrete region when making replicate measurements, or to slowly scan the excitation beam across a portion of the discrete region over the course of a single measurement, thereby eliminating potential concerns regarding the photo-bleaching effects of long exposures or prior exposures.

Consequently, the methods and systems disclosed herein further comprise specifying the precision with which the translation stage is capable of positioning a substrate in relation to the excitation light beam. In one aspect of the present disclosure, the precision of the translation stage is between about 1 um and about 10 um. In other aspects, the precision of the translation stage is about 10 um or less, about 9 um or less, about 8 um or less, about 7 um or less, about 6 um or less, about 5 um or less, about 4 um or less, about 3 um or less, about 2 um or less, or about 1 um or less. Those of skill in the art will appreciate that the precision of the translation stage may fall within any range bounded by any of these values (e.g. from about 1.5 um to about 7.5 um).

Fluid Dispensing System

As illustrated in FIG. 4, some embodiments of the high throughput systems disclosed herein further comprise an automated, programmable fluid-dispensing (or liquid-dispensing) system for use in contacting the biological or target entities immobilized on the substrate surface with test entities (or test compounds), the latter typically being dispensed in solutions comprising aqueous buffers with or without the addition of a small organic solvent component, e.g. dimethylsulfoxide (DMSO). Suitable automated, programmable fluid-dispensing systems are commercially available from a number of vendors, e.g. Beckman Coulter, Perkin Elmer, Tecan, Velocity 11, and many others. In a preferred aspect of the systems and methods disclosed herein, the fluid-dispensing system further comprises a multichannel dispense head, e.g. a 4 channel, 8 channel, 16 channel, 96 channel, or 384 channel dispense head, for simultaneous delivery of programmable volumes of liquid (e.g. ranging from about 1 microliter to several milliliters) to multiple wells or locations on the substrate.

Plate-Handling Robotics

In other aspects of the high throughput systems disclosed herein, the system further comprises a microplate-handling (or plate-handling) robotic system (FIG. 4) for automated replacement and positioning of substrates (in any of the formats described above) in relation to the optical excitation and detection optics, or for optionally moving substrates between the optical instrument and the fluid-dispensing system. Suitable automated, programmable microplate-handling robotic systems are commercially available from a number of vendors, including Beckman Coulter, Perkin Elemer, Tecan, Velocity 11, and many others. In a preferred aspect of the systems and methods disclosed herein, the automated microplate-handling robotic system is configured to move collections of microwell plates comprising immobilized biological entities and/or aliquots of test compounds to and from refrigerated storage units.

Processor/Controller and Constraint-Based Scheduling Algorithm

In another aspect of the present disclosure, the high throughput systems disclosed further comprise a processor (or controller, or computer system) (FIG. 4) configured to run system software which controls the various subsystems described (excitation and detection optical systems, X-Y (or X-Y-Z) translation stage, fluid-dispensing system, and plate-handling robotics) and synchronizes the different operational steps involved in performing high throughput conformational analysis. In addition to handling the data acquisition process, i.e. collection of output electronic signals from the detector that correspond to the nonlinear optical signals associated with conformational change, the processor or controller is also typically configured to store the data, perform data processing and display functions (including determination of whether or not changes in orientation or conformation have occurred for the biological entities, or combinations of biological and test entities, that have been tested), and operate a graphical user interface for interactive control by an operator. The processor or controller may also be networked with other processors, or connected to the internet for communication with other instruments and computers at remote locations.

Typical input parameters for the processor/controller may include set-up parameters such as the total number of microwell plates to be analyzed; the number of wells per plate; the number of times excitation and detection steps are to be performed for each discrete region of the substrate or well of the microplate (e.g. to specify endpoint assay or kinetic assay modes); the total timecourse over which kinetic data should be collected for each discrete region or well; the order, timing, and volume of test compound solutions to be delivered to each discrete region or well; the dwell time for collection and integration of nonlinear optical signals; the name(s) of output data files; and any of a number of system set-up and control parameters known to those skilled in the art.

In a preferred aspect of the present disclosure, the processor or controller is further configured to perform system throughput optimization by means of executing a constraint-based scheduling algorithm. This algorithm utilizes system set-up parameters as described above to determine an optimal sequence of interspersed excitation/detection and liquid-dispensing steps for discrete regions or wells that may or may not be adjacent to each other, such that the overall throughput of the system, in terms of number of biological entities and/or test entities analyzed per hour, is maximized. Optimization of system operational steps is an important aspect of achieving high throughput analysis. In some aspects of the disclosed methods and systems, the average throughput of the analysis system may range from about 10 test entities tested per hour to about 1,000 test entities tested per hour. In some aspects, the average throughput of the analysis system may be at least 10 test entities tested per hour, at least 25 test entities tested per hour, at least 50 test entities tested per hour, at least 75 test entities tested per hour, at least 100 test entities tested per hour, at least 200 test entities tested per hour, at least 400 test entities tested per hour, at least 600 test entities tested per hour, at least 800 test entities tested per hour, or at least 1,000 test entities tested per hour. In other aspects, the average throughput of the analysis system may be at most 1,000 test entities tested per hour, at most 800 test entities tested per hour, at most 600 test entities tested per hour, at most 400 test entities tested per hour, at most 200 test entities tested per hour, at most 100 test entities tested per hour, at most 75 test entities tested per hour, at most 50 test entities tested per hour, at most 25 test entities tested per hour, or at most 10 test entities tested per hour.

Computer Systems and Networks

In various embodiments, the methods and systems of the invention may further comprise software programs installed on computer systems and use thereof. Accordingly, as noted above, computerized control of the various subsystems and synchronization of the different operational steps involved in performing high throughput conformational analysis, including data analysis and display, are within the bounds of the invention.

Figure 15:
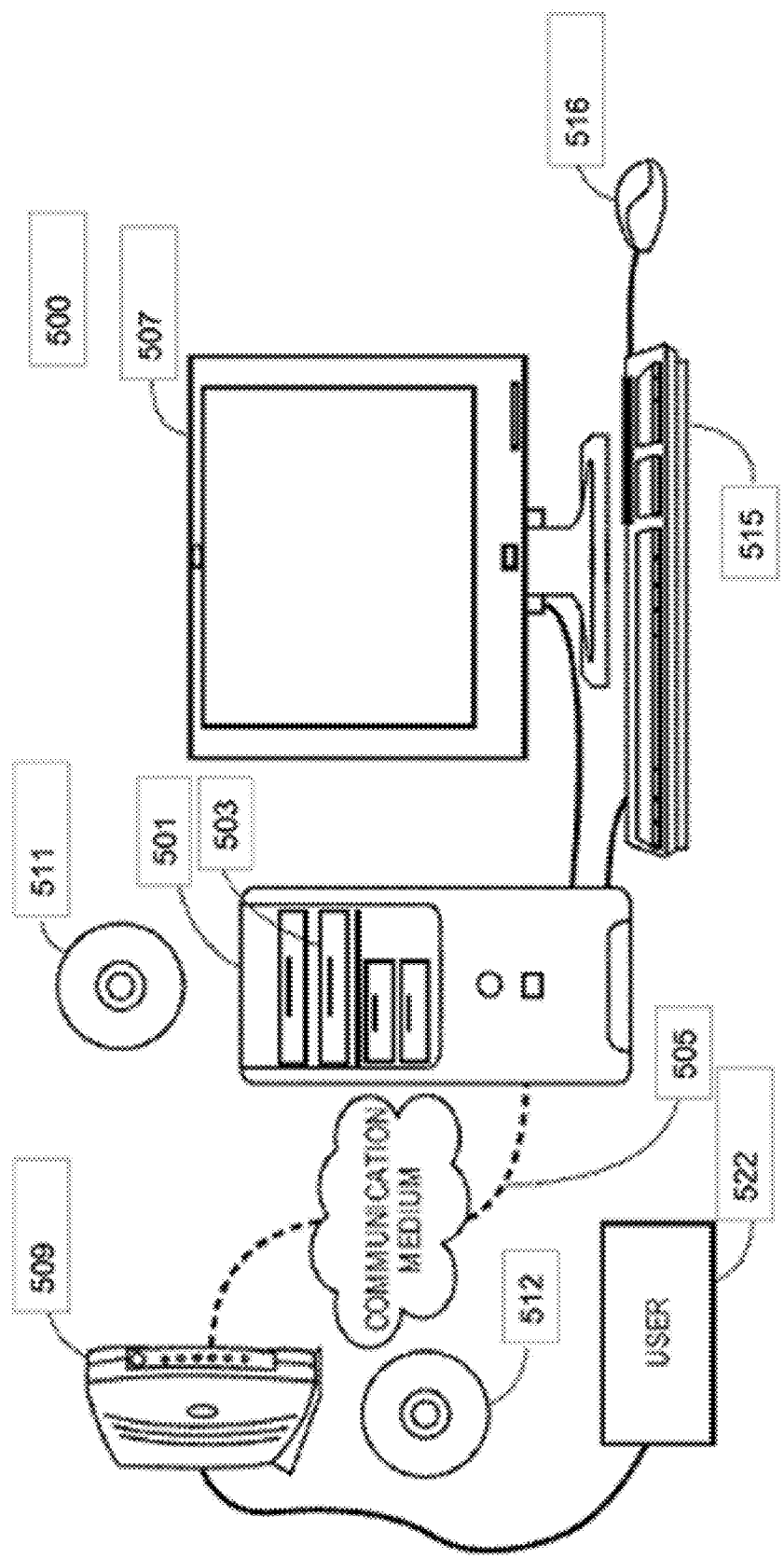
FIG. 15 illustrates a computer system that may be configured to control the operation of the systems disclosed herein.

The computer system 500 illustrated in FIG. 15 may be understood as a logical apparatus that can read instructions from media 511 and/or a network port 505, which can optionally be connected to server 509 having fixed media 512. The system, such as shown in FIG. 15 can include a CPU 501, disk drives 503, optional input devices such as keyboard 515 and/or mouse 516 and optional monitor 507. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 522 as illustrated in FIG. 15.

Figure 16:
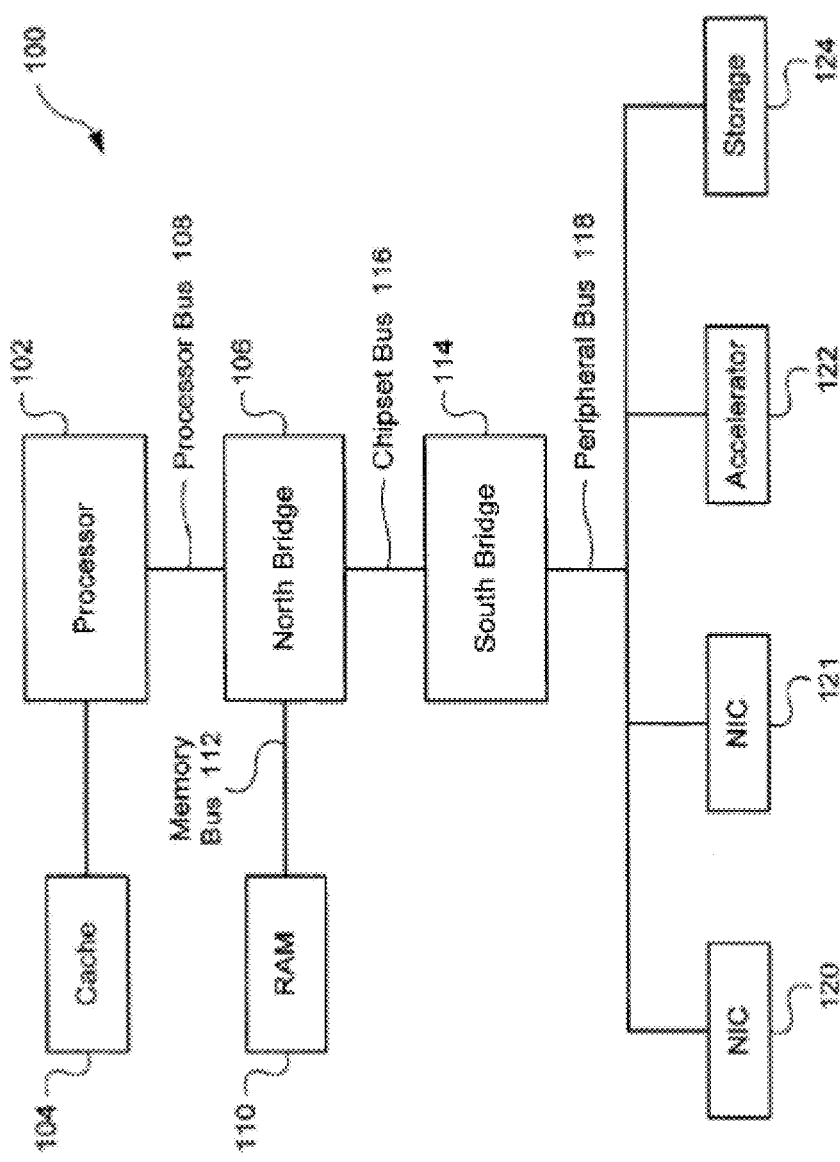
FIG. 16 is a block diagram illustrating a first example architecture of a computer system that can be used in connection with example embodiments of the present invention.

FIG. 16 is a block diagram illustrating a first example architecture of a computer system 100 that can be used in connection with example embodiments of the present invention. As depicted in FIG. 16, the example computer system can include a processor 102 for processing instructions. Non-limiting examples of processors include: the Intel Xeon™ processor, the AMD Opteron™ processor, the Samsung 32-bit RISC ARM 1176JZ(F)-S v1.0™ processor, the ARM Cortex-A8 Samsung S5PC100™ processor, the ARM Cortex-A8 Apple A4™ processor, the Marvell PXA 930™ processor, or a functionally-equivalent processor. Multiple threads of execution can be used for parallel processing. In some embodiments, multiple processors or processors with multiple cores can also be used, whether in a single computer system, in a cluster, or distributed across systems over a network comprising a plurality of computers, cell phones, and/or personal data assistant devices.

As illustrated in FIG. 16, a high speed cache 104 can be connected to, or incorporated in, the processor 102 to provide a high speed memory for instructions or data that have been recently, or are frequently, used by processor 102. The processor 102 is connected to a north bridge 106 by a processor bus 108. The north bridge 106 is connected to random access memory (RAM) 110 by a memory bus 112 and manages access to the RAM 110 by the processor 102. The north bridge 106 is also connected to a south bridge 114 by a chipset bus 116. The south bridge 114 is, in turn, connected to a peripheral bus 118. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 118. In some alternative architectures, the functionality of the north bridge can be incorporated into the processor instead of using a separate north bridge chip.

In some embodiments, system 100 can include an accelerator card 122 attached to the peripheral bus 118. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 124 and can be loaded into RAM 110 and/or cache 104 for use by the processor. The system 100 includes an operating system for managing system resources; non-limiting examples of operating systems include: Linux, Windows™, MacOS™, BlackBerry OS™, iOS™, and other functionally-equivalent operating systems, as well as application software running on top of the operating system for managing data storage and optimization in accordance with example embodiments of the present invention.

In this example, system 100 also includes network interface cards (NICs) 120 and 121 connected to the peripheral bus for providing network interfaces to external storage, such as Network Attached Storage (NAS) and other computer systems that can be used for distributed parallel processing.

Figure 17:
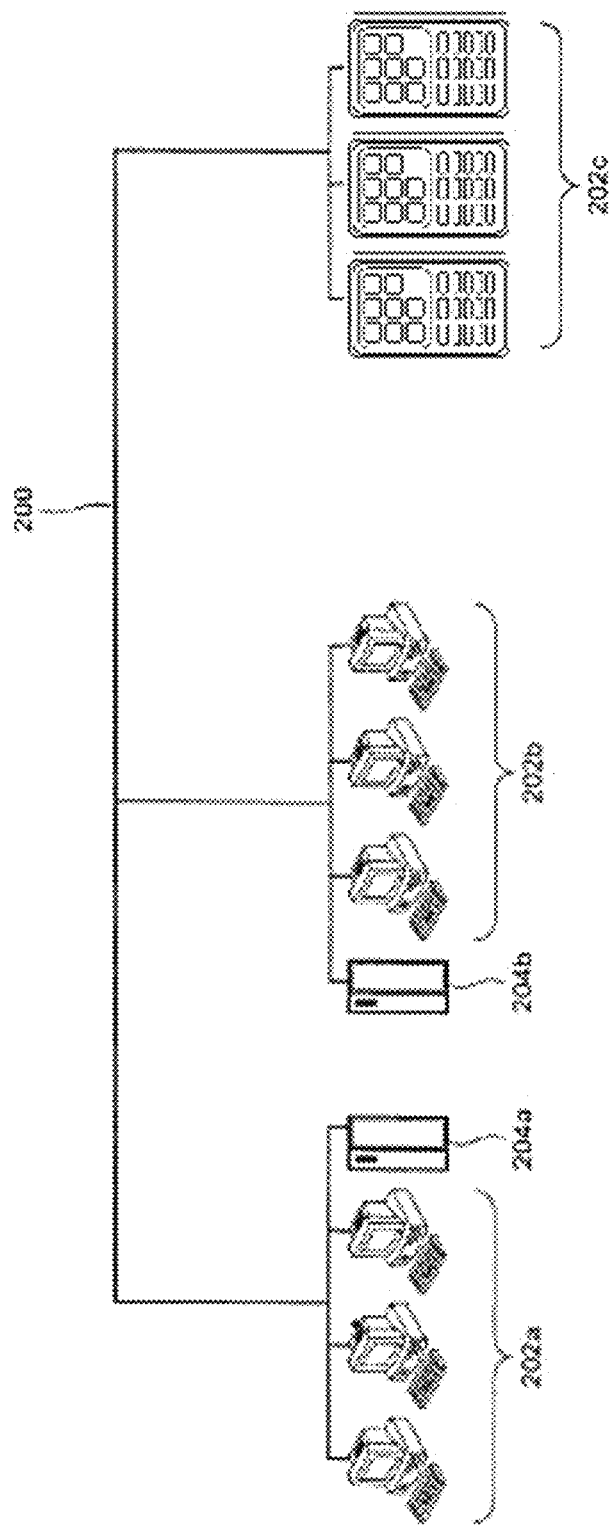
FIG. 17 is a diagram showing one embodiment of a network with a plurality of computer systems, a plurality of cell phones and personal data assistants, and Network Attached Storage (NAS).

FIG. 17 is a diagram showing a network 200 with a plurality of computer systems 202a, and 202b, a plurality of cell phones and personal data assistants 202c, and Network Attached Storage (NAS) 204a, and 204b. In example embodiments, systems 202a, 202b, and 202c can manage data storage and optimize data access for data stored in Network Attached Storage (NAS) 204a and 204b. A mathematical model can be used for the data and be evaluated using distributed parallel processing across computer systems 202a, and 202b, and cell phone and personal data assistant systems 202c. Computer systems 202a, and 202b, and cell phone and personal data assistant systems 202c can also provide parallel processing for adaptive data restructuring of the data stored in Network Attached Storage (NAS) 204a and 204b. FIG. 17 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface.

In some example embodiments, processors can maintain separate memory spaces and transmit data through network interfaces, back plane or other connectors for parallel processing by other processors. In other embodiments, some or all of the processors can use a shared virtual address memory space.

Figure 18:
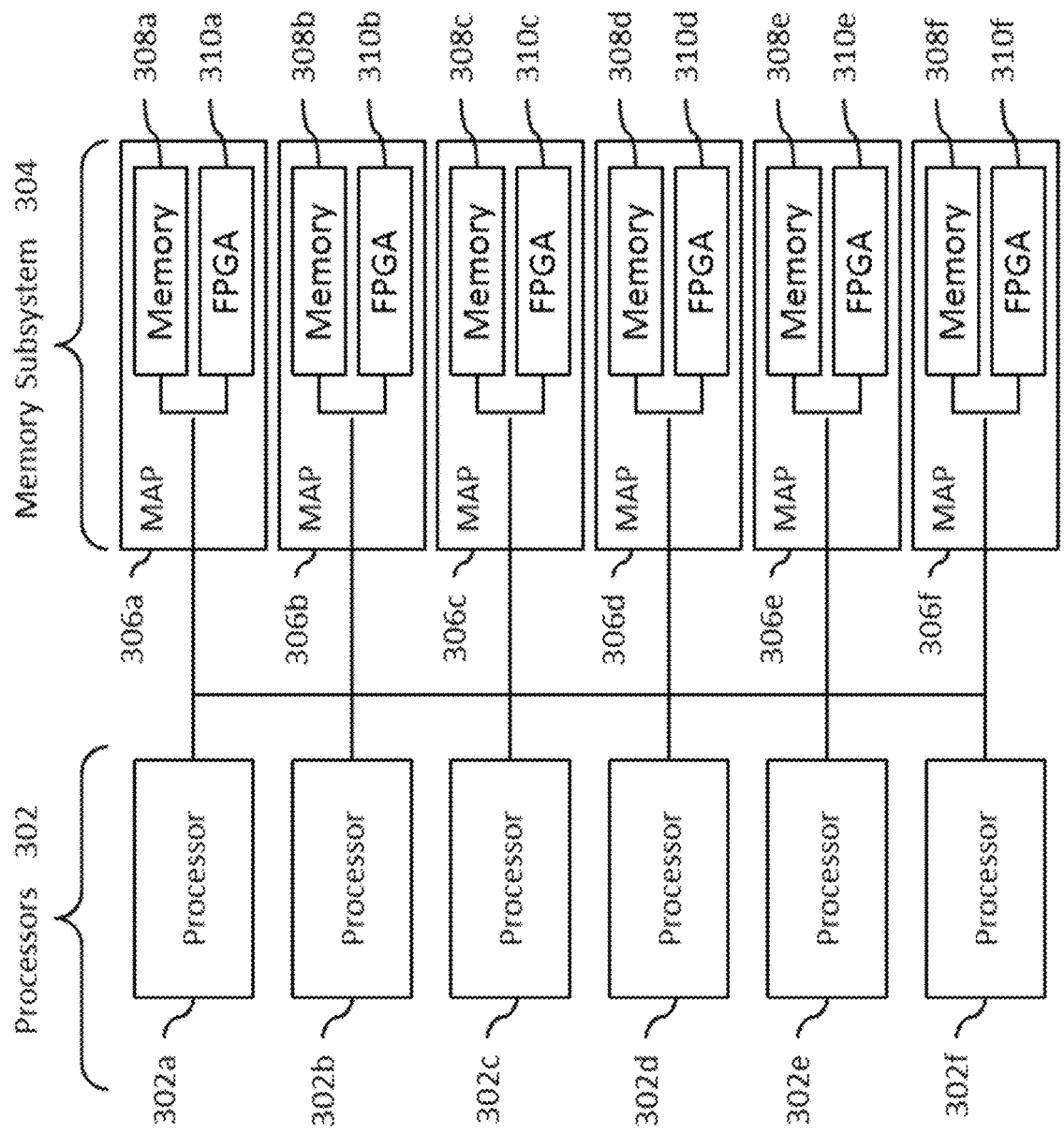
FIG. 18 is a block diagram of a multiprocessor computer system using a shared virtual address memory space in accordance with an example embodiment.

FIG. 18 is a block diagram of a multiprocessor computer system using a shared virtual address memory space in accordance with an example embodiment. The system includes a plurality of processors 302a-f that can access a shared memory subsystem 304. The system incorporates a plurality of programmable hardware memory algorithm processors (MAPs) 306a-f in the memory subsystem 304. Each MAP 306a-f can comprise a memory 308a-f and one or more field programmable gate arrays (FPGAs) 310a-f. The MAP provides a configurable functional unit and particular algorithms or portions of algorithms can be provided to the FPGAs 310a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 308a-f, allowing it to execute tasks independently of, and asynchronously from, the respective microprocessor 302a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 18, system on chips (SOCs), application specific integrated circuits (ASICs), or other processing and logic elements. For example, the Set Processor and Optimizer can be implemented with hardware acceleration through the use of a hardware accelerator card, such as accelerator card 122 illustrated in FIG. 16.

EXAMPLE 1—DETERMINATION OF STRUCTURAL PARAMETERS IN DIHYDROFOLATE REDUCTASE (DHFR) MUTANTS

Glassware and Sonicated Lipid Preparation:

Clean all glassware with Piranha wash (20 minutes) prior to starting. Use caution—Piranha wash is highly exothermic and prone to explosion, especially when in contact with organics. Prepare a solution in heat-safe glassware such as Pyrex in a fume hood by measuring out $H_2O_2$ first, then adding acetic acid. Rinse vacuum bottles with Chloroform ($CHCl_3$). Determine desired molar ratio of DOPC lipid to DGS NTA-Ni while taking care to avoid exposure to air as much as possible. Place vacuum bottle with lipid mix onto a Rotovap evaporator. Evaporate until dry (about 30 seconds) and then blow $N_2$ gas over the evaporated preparation for 10 min to remove residual $CHCl_3$. Resuspend the lipid mixture in 2 mL of $diH_2O$. Vortex vigorously until a cloudy suspension forms (about 5 minutes). Transfer the suspension to a 4 mL polystyrene test tube. Sonicate the lipid mixture on ice until the solution clears. This should require about 60 to 90 seconds with the sonicator set to 25% power.

Transfer the sonicated lipid solution into microcentrifuge tubes and centrifuge at 17,000×G for 30 minutes at 4° C. Transfer the supernatant into clean microcentrifuge tubes and store the finished lipid preps at 4° C. which are stable for about 1 month.

Slide Preparation and Protein Loading:

Immediately before applying DOPC/DGS NTA (Ni) lipids, clean microscope slides with Piranha wash for 20 minutes. Rinse 3× with $diH_2O$ in a slide staining vessel. Dry slides with compressed Nitrogen. Assemble SHG wells by attaching adhesive gaskets to Piranha-cleaned slides (i.e., 16 wells per slide containing 10-20 µl volume). Use an assembly jig to align gaskets, carefully lay slide into jig and press firmly. Dilute DOPC/DGS NTA (Ni) lipid prep 1:1 with PBS or TBS buffers. 100 mM NaCl is required to reduce hydrostatic charge of the glass slide and enable the supported lipid bilayer (SLB) to form. Pipet 10-20 µL of diluted DOPC/DGS NTA (Ni) lipid into the wells of the slide and incubate for 5 minutes at room temperature. Wash the wells by submersing the slide in buffer bath (PBS or TBS) and agitating with a 200 µL pipettor taking care not to introduce air into the wells at any time. Exchange the entire volume of buffer in the bath with fresh buffer and repeat the washing step 2 more times. Add a 1:1 volume of 100 mM $NiCl_2$ solution to all wells and incubate for 10 minutes at room temperature. Wash the wells by submersing the slide in buffer bath (PBS or TBS) and agitating with a 200 µL pipettor. Exchange the entire volume of buffer in bath with fresh buffer and repeat the washing step 2 more times. If necessary, exchange the buffer in the wells to an appropriate protein loading buffer and load the target protein of interest onto the wells. Incubate for 30 to 90 minutes at room temperature followed by a thorough rinse of the wells with assay buffer before starting experiments.

Small unilamellar vesicles (SUVs) are prepared by sonication as described above and applied over Piranha-washed Fisher slides to make the SLB surface. $NiCl_2$ was added for 10 minutes and wells were washed in labeling buffer.

Labeled protein is loaded onto the SLB surface prepared as describe above at 3 µM (micromolar) for 45 minutes, followed by washing. If imidazole or EDTA is added or the protein is incubated with the SLB surface in the presence of one or both, the SHG signal drops to the baseline level indicating that attachment to the surface occurs specifically via the protein's His-tag.

A mutant of the *Escherichia coli* protein dihydrofolate reductase (DHFR) with either an N-terminal or C-terminal 8× His tag was created using methods known in the art (Rajagopalan, P., et al. (2002), "Interaction of Dihydrofolate Reductase with Methotrexate: Ensemble and Single-Molecule Kinetics", Proc. Nat. Acad. of Sci. (USA) 99(21): 13481-6; Goodey, N. (2008), "Allosteric Regulation and Catalysis Emerge via a Common Route", Nat Chem. Biol. 4(8):474-82; Antikainen, N. (2005), "Conformation Coupled Enzyme Catalysis: A Single-Molecule and Transient Kinetics Investigation of Dihydrofolate Reductase", Biochemistry 44(51):16835-43). In the first case, a cysteine minimized mutant was made in which both native cysteines were removed (C85A and C152A). Then two single, different residues (e.g., M16C, N23C, Q65C, V136C, D142C, A19C, etc.) were mutated to cysteine, i.e. two single-site mutant constructs were created in this cysteine minimized background: mutant 1 and mutant 2. To select the site for the mutation, various residues on the surface of the protein were mutated to cysteine and tested for an ability to be labeled by an SHG probe. In the second case, the wild-type protein was labeled and attachment of the probe to C152 was confirmed by mass spectrometry. Wild type or recombinant protein was purified into 25 mM Tris pH 7.2, 150 mM NaCl. The proteins were labeled using a maleimide dye following the manufacturer's instructions, e.g. protein was incubated in 25 mM Tris pH 7.2, 150 mM NaCl, 1 mM TCEP and 10% glycerol at approximately 50 uM with a 20:1 dye:protein labeling ratio (final DMSO concentration was 5%). The protein was stirred overnight at 4° C., and then gel-purified into 25 mM Tris-HCl pH 7.2, 150 mM NaCl, 1 mM TCEP. Labeled and purified protein was then tethered to the SLB surface via the His-tag.

Polarization-dependent measurements of the SHG signal were used to determine the independent, non-vanishing components of $\chi^{(2)}$ for the two different mutants using methods known to those skilled in the art. For example, in the simplest optical geometry, and assuming azimuthal isotropy and a single dominant component of the hyperpolarizability tensor, one determines two independent non-vanishing components of $\chi^{(2)}$ ($\chi_{zzz}$ and $\chi_{xzx}$ or $\chi_{zxx}$). These in turn were used to best determine the orientational distributions related to the θ's for each of the mutants (i.e., $\theta_1$ and $\theta_2$).

For example, for V136C, Q65C, and N23C labeled at the single-site cysteines tethered to the lipid bilayer via a His-tag at the C-terminus, the mean angle of the dye hyperpolarizability relative to the surface normal (z-axis), assuming a Delta function in orientation (single angle and no width in the orientational distribution), was as follows:

| | |
|---|---|
| V136C | 35.3° |
| Q65C | 47.5° |
| N23C | 38.5° |

Figure 13B:
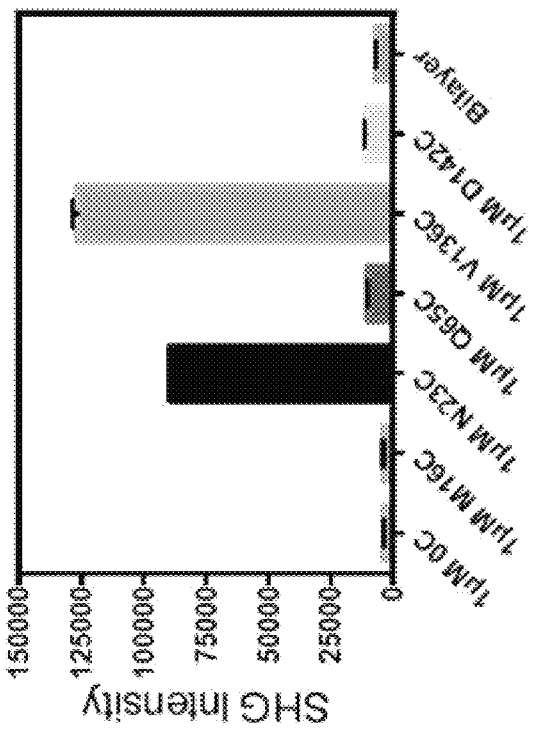
FIGS. 13A-B show examples of data for the SHG signal intensities observed for cysteine-labeled mutants of a protein molecule (dihydrofolate reductase (DHFR)) tethered to an optical interface.
Figure 13A:
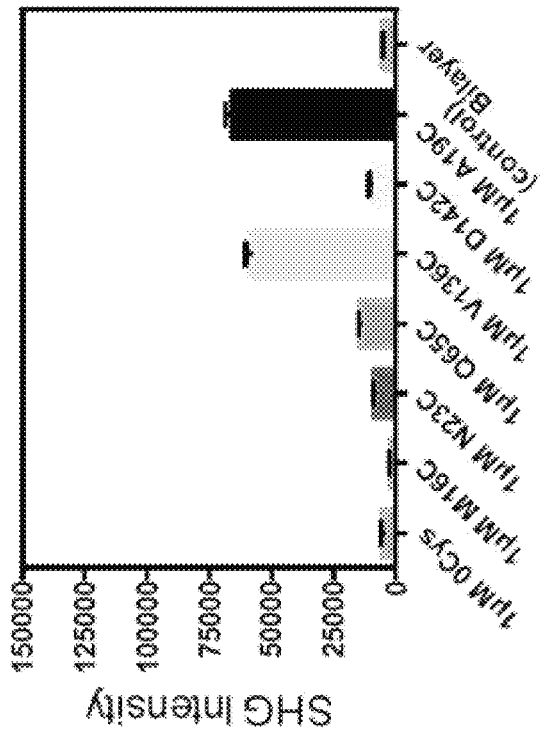

FIGS. 13A-B shows the $I_{zzz}$ measurements for various SHG-labeled single-site cysteine mutants tagged and tethered by the His tag at either the N-terminus or the C-terminus. As was immediately obvious, the absolute signal magnitudes of the labeled proteins (the baseline signals) varied from label site to label site for N-terminal and C-terminal tagged and tethered proteins (FIG. 13A and FIG. 13B, respectively).

Figure 14B:
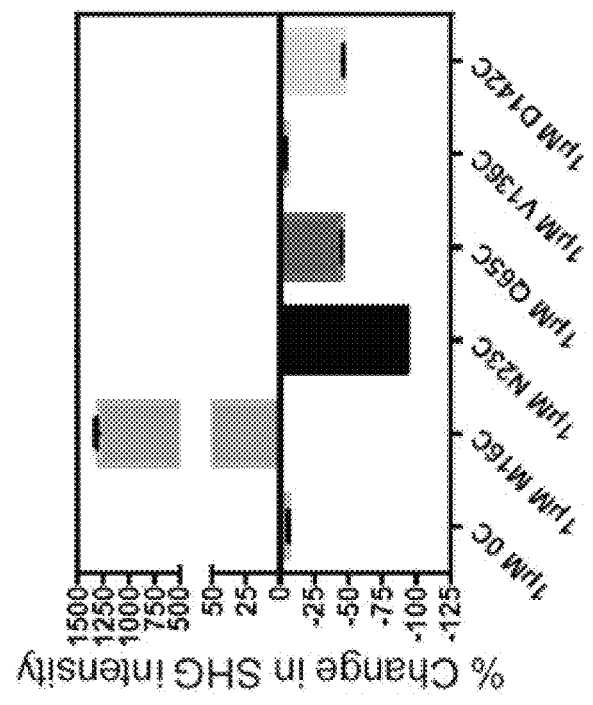
FIGS. 14A-B show examples of data for the percent change in SHG signal intensities observed for cysteine-labeled mutants of a protein molecule (dihydrofolate reductase (DHFR)) tethered to an optical interface following the addition of a known ligand (trimethoprim (TMP)).
Figure 14A:
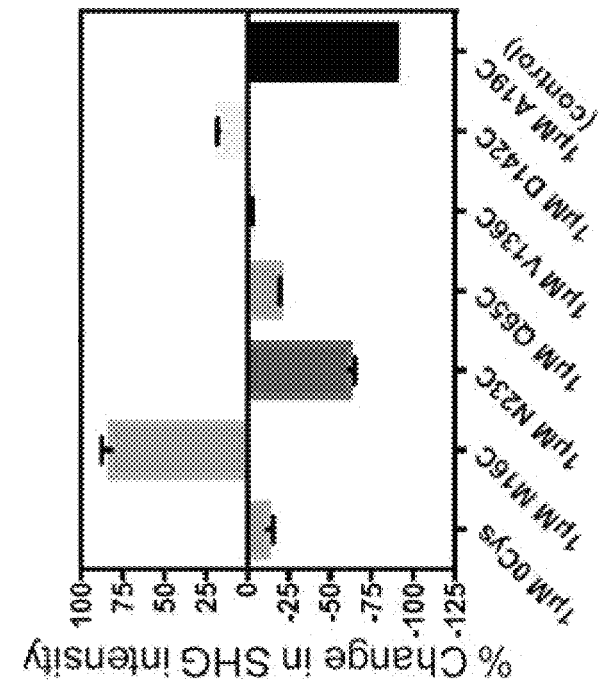

Addition of ligand caused changes in the SHG baseline signal levels (SHG % changes), either positive or negative, which result from reorientation of the labels across the protein ensemble, in other words, from changes in the label orientational distribution as a result of ligand binding. FIGS. 14A and 14B show the results of an experiment in which 1 uM (micromolar) TMP ligand, which is well known to bind DHFR to those skilled in the art, produced differential changes in baseline signal ($I_{zzz}$). As can be seen in FIGS. 14A and 14B, the direction and magnitude of the SHG signal changes varied from site to site both for common tagging and tethering (e.g., N-terminal or C-terminal tagging) and across the results for N- and C-terminal tagged mutants. For example, as seen in FIG. 14A, addition of TMP causes a roughly 70% decrease in baseline signal for the protein mutant that is attached and oriented via it's His tag at the N-terminus, but an approximately 90% decrease for the mutant that is attached and oriented via a His tag at the C-terminus.

Similar measurements can be repeated for $I_{zxx}$, and a ratio of the two polarization-dependent intensities can be used to determine the mean angle of the label at each cysteine site as a function of protein construct (e.g., N- or C-terminus tag) assuming a narrow orientational distribution.

EXAMPLE 2 (PROPHETIC)

The experiment of Example 1 may be extended to include 3 or more different His-tag lengths which result in different orientational distributions to be observed. This increases the number of independent polarization measurements to 48 and increases the accuracy of the angular measurements and the protein structural models.

EXAMPLE 3 (PROPHETIC)

The experiment of Example 2 may be extended to include 4 different buffers of varying salt concentration (e.g. 0, 50 mM, 200 mM and 300 mM NaCl) which produces different orientational distributions. This increases the number of independent polarization measurements to 384 and increases the accuracy of the angular measurements and the protein structural models.

EXAMPLE 4 (PROPHETIC)

The experiment of Example 3 may be extended to include different concentrations of a molecule added to the buffer (i.e. an additive) (e.g. PEG400 (10 uM, 20 uM, 40 uM and 80 uM micromolar PEG400)) which associates with the interfacial region and produces different orientational distributions. This increases the number of independent orientational distributions and polarization measurements and thus increases the accuracy of the angular measurements and the protein structural models.

EXAMPLE 5 (PROPHETIC)

The experiment of Example 4 may be extended to include a transverse E-field applied across the supported lipid bilayer according to methods known to those skilled in the art. Four different electric field strengths (zero, low, medium, and high) are applied. Metallic strips are patterned across a bilayer region in a 384-well glass-bottom plate well (~3 mm diameter), and a voltage ranging from 0.1-100 V is applied to these strips corresponding to field strengths of ~1 V/cm-1E$^4$ V/cm. The applied electric field alters the orientational distribution of the protein population via electrophoretic and electroosmotic mechanisms as is known to those skilled in the art; different magnitudes applied electric field result in different orientational populations of the protein and allow for independent polarization measurements. This increases the accuracy of the angular measurements and the protein structural models.

EXAMPLE 6

The experiment of Example 5 may be extended to include 10 different mutants of DHFR, each labeled at a different single cysteine site. This increases the number of independent polarization measurements and the accuracy of the angular measurements and the protein structural models.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for determining protein structure in solution, the method comprising:
   (a) tethering protein molecules to a surface under three or more different sets of experimental conditions known to produce different orientational distributions of the tethered protein molecules, wherein the protein molecules are labeled at one or more known positions with one or more nonlinear-active labels for each experimental condition, and wherein the three or more different sets of experimental conditions comprise two or more of: (i) tethering the protein molecules using a His-tag attached to the N-terminus, (ii) tethering the protein molecules using a His-tag attached to the C-terminus, and (iii) tethering the protein molecules to at least two surfaces of different composition;
   (b) illuminating the tethered protein molecules of step (a) with excitation light of at least one fundamental frequency and a first polarization, wherein the excitation light is provided by at least one light source;
   (c) detecting a first intensity of light generated by the one or more nonlinear-active labels as a result of the illumination in step (b) for the three or more different sets of experimental conditions;
   (d) illuminating the tethered protein molecules of step (a) with excitation light of the at least one fundamental frequency and a second polarization;
   (e) detecting a second intensity of light generated by the one or more nonlinear-active labels as a result of the illumination in step (d) for the three or more different sets of experimental conditions;
   (f) calculating intensity ratios for the light detected at the first and second polarizations for each set of experimental conditions to determine a relative orientation of the one or more nonlinear-active labels in the tethered protein molecules for each set of experimental conditions; and
   (g) globally fitting data for the relative orientation of the one or more nonlinear-active labels under each set of experimental conditions to a structural model of the protein molecule, wherein the structural model is based on known positions of the one or more nonlinear-active labels within the protein molecule.

2. The method of claim 1, further comprising repeating steps (a) through (f) for at least two different nonlinear-active label-protein conjugates, wherein the nonlinear-active labels are attached to at least two different sites on the protein molecule.

3. The method of claim 2, wherein the at least two different nonlinear-active label-protein conjugates each comprise a single-site cysteine.

4. The method of claim 1, wherein the nonlinear-active labels are nonlinear-active unnatural amino acids.

5. The method of claim 1, wherein the first and the at least second physical properties of light possess the same polarization but are of different magnitudes or intensities.

6. The method of claim 1, wherein the first and at the least second physical properties of light possess different polarizations.

7. The method of claim 4, wherein the nonlinear-active unnatural amino acid is Aladan or a derivative of naphthalene.

8. The method of claim 1, further comprising incorporating x-ray crystallographic data for the protein into the structural model of the protein molecule.

9. The method of claim 1, wherein one of the three or more different sets of experimental conditions comprises applying a first electric field of a first electric field strength to the tethered protein molecules, and another one the three or more different sets of experimental conditions comprises applying a second electric field of a second electric field strength to the tethered protein molecules.

10. The method of claim 9, wherein the first electric field and the second electric field are selected from the group consisting of direct current (DC) fields, alternating current (AC) fields, and any combination thereof.

11. The method of claim 9, wherein the first electric field and the second electric field are applied using an array of electrodes fabricated on the surface.

12. The method of claim 11, wherein the array of electrodes is a circular array as illustrated in FIG. 9.

13. The method of claim 1, wherein one of the three or more different sets of experimental conditions comprises tethering the protein molecules using a first His-tag selected from the group consisting of 2×His, 4×His, 6×His, 8×His, 10×His, 12×His, and 14×His, and another one of the three or more different sets of experimental conditions comprises tethering the protein molecules using a second His-tag that differs in length from the first His-tag.

14. The method of claim 1, wherein one of the three or more different sets of experimental conditions comprises tethering the protein molecules using a first assay buffer, and another one of the three or more different sets of experimental conditions comprises tethering the protein molecules using a second assay buffer that differs from the first assay buffer.

15. The method of claim 14, wherein the difference between the first assay buffer and the second assay buffer is selected from the group consisting of ionic strength, pH, detergent concentration, calcium ion ($Ca^{2+}$) concentration, magnesium ion ($Mg^{2+}$) concentration, polyethylene glycol concentration, and any combination thereof.

16. The method of claim 1, wherein the difference between one of the three or more different sets of experimental conditions and another one of the three or more different sets of experimental conditions comprises contacting the tethered protein molecules with at least a first ligand that is known to bind to and induce conformational change in the protein molecules.

17. The method of claim 1, wherein the one or more nonlinear-active labels located at the one or more known positions are the same.

18. The method of 1, wherein the one or more nonlinear-active labels located at the one or more known positions are different.

19. The method of claim 1, wherein the one or more nonlinear-active labels are selected from the group consisting of second harmonic (SH)-active labels, sum frequency (SF)-active labels, and difference frequency (DF)-active labels.

20. The method of claim 1, wherein the detecting in steps (c) and (e) comprise adjusting the polarization of the light generated by the one or more nonlinear-active labels that reaches a detector.

21. The method of claim 1, wherein the one or more nonlinear-active labels are selected from the group consisting of pyridyloxazole (PyMPO), PyMPO succinimidyl ester, and PyMPO maleimide.

\* \* \* \* \*